US009795665B2

(12) United States Patent
Bergeron et al.

(10) Patent No.: US 9,795,665 B2
(45) Date of Patent: *Oct. 24, 2017

(54) ATTENUATED LIVE VACCINE FOR CRIMEAN-CONGO HEMORRHAGIC FEVER VIRUS AND ERVE VIRUS

(71) Applicants: The United States of America as Represented by the Secretary of the Department of Health and Human Services, Washington, DC (US); COLORADO SEMINARY, WHICH OWNS AND OPERATES THE UNIVERSITY OF DENVER, Denver, CO (US)

(72) Inventors: Eric Bergeron, Atlanta, GA (US); Scott Dusan Pegan, Denver, CO (US); Stuart T. Nichol, Atlanta, GA (US); Michelle Kay Deaton, Denver, CO (US)

(73) Assignee: THE UNITED STATES OF AMERICA, AS REPRESENTED BY THE SECRETARY, DEPARTMENT OF HEALTH AND HUMAN SERVICES, Washington, DC (US)

( * ) Notice: Subject to any disclaimer, the term of this patent is extended or adjusted under 35 U.S.C. 154(b) by 26 days.

This patent is subject to a terminal disclaimer.

(21) Appl. No.: 14/421,120

(22) PCT Filed: Aug. 13, 2013

(86) PCT No.: PCT/US2013/054760
§ 371 (c)(1),
(2) Date: Feb. 11, 2015

(87) PCT Pub. No.: WO2014/028511
PCT Pub. Date: Feb. 20, 2014

(65) Prior Publication Data
US 2015/0306202 A1    Oct. 29, 2015

Related U.S. Application Data

(63) Continuation of application No. 13/829,105, filed on Mar. 14, 2013, now Pat. No. 9,474,796.

(60) Provisional application No. 61/683,132, filed on Aug. 14, 2012.

(51) Int. Cl.
| | |
|---|---|
| *C12N 7/00* | (2006.01) |
| *A61K 39/12* | (2006.01) |
| *C12Q 1/04* | (2006.01) |
| *A61K 39/00* | (2006.01) |

(52) U.S. Cl.
CPC ............ *A61K 39/12* (2013.01); *C12N 7/00* (2013.01); *C12Q 1/04* (2013.01); *A61K 2039/5254* (2013.01); *C12N 2760/12034* (2013.01); *G01N 2333/175* (2013.01)

(58) Field of Classification Search
None
See application file for complete search history.

(56) References Cited

U.S. PATENT DOCUMENTS

| 8,012,489 B2 | 9/2011 | Jones |
|---|---|---|
| 2003/0186431 A1 | 10/2003 | Torres |
| 2006/0057159 A1 | 3/2006 | Huang et al. |
| 2014/0050761 A1* | 2/2014 | Bergeron ............... A61K 39/12 424/205.1 |

FOREIGN PATENT DOCUMENTS

WO    2009/008924 A2    1/2009

OTHER PUBLICATIONS

Akutsu, et al., "Molecular basis for ubiquitin and ISG15 cross-reactivity in viral ovarian tumor domains," PNAS, vol. 108, No. 6, pp. 2228-2233 (2011).
Frias-Staheli, et al., "Ovarian Tumor Domain-Containing Viral Proteases Evade Ubiquitin- and ISG15-Dependent Innate Immune Responses," Cell Host Microbe., vol. 2(6), pp. 404-416 (2007).
Holzer, et al., "Inhibition of Interferon Induction and Action by the Nairovirus Nairobi Sheep Disease Virus/Ganjam Virus," PLoS ONE vol. 6(12), e28594, pp. 1-12 (2011).
Kasteren, et al., "Arterivirus and Nairovirus Ovarian Tumor Domain-Containing Deubiquitinases Target Activated RIG-I to Control Innate Immune Signaling," J Virol., vol. 86(2), pp. 773-785 (2012).
Extended European Search Report for European Application No. 13829120.8 dated Feb. 25, 2016, 9 pages.
International Search Report and Written Opinion for PCT Application No. PCT/US2013/054760 dated Oct. 16, 2013.
Ambrosio et al., "Argentine hemorrhagic fever vaccines," Human Vaccines, vol. 7, No. 6 (Jun. 2011) 7 pages.
Bergeron et al., "Crimean-Congo hemorrhagic fever virus-encoded ovarian tumor protease activity is dispensable for virus RNA polymerase function," Journal of Virology, vol. 84, No. 1 (Jan. 2010) 11 pages.
Capodagli et al., "Diversity of Ubiquitin and ISG15 Specificity among Nairoviruses' Viral Ovarian Tumor Domain Proteases," Journal of Virology 87(7): 3815-3827 (2013).
Capodagli et al., "Structural Analysis of a Viral Ovarian Tumor Domain Protease from the Crimean-Congo Hemorrhagic Fever Virus in Complex with Covalently Bonded Ubiquitin," Journal of Virology, vol. 85, No. 7 (Apr. 2011) 10 pages.
Carter, SD., et al., "Structure, function, and evolution of the Crimean-Congo hemorrhagic fever virus nucleocapsid protein," Journal of Virology, vol. 86, No. 20 (Aug. 2012) 10 pages.

(Continued)

*Primary Examiner* — Michelle S Horning
(74) *Attorney, Agent, or Firm* — Kevin Bastian; Kilpatrick Townsend & Stockton LLP

(57) ABSTRACT

The genetically modified nairoviruses of this invention possesses a viral ovarian tumor protease with decreased ability to remove ubiquitin (Ub) and ISG15 tags that the human organism uses to label proteins for removal. Exemplary are Crimean-Congo hemorrhagic fever virus and Erve virus. Unlike complete knockout strains, the modified virus retains enough activity for replication in a human cell line. This creates an immunogenic and non-pathogenic virus that can be used as an effective live vaccine agent for prophylaxis and treatment.

19 Claims, 11 Drawing Sheets

(56) References Cited

OTHER PUBLICATIONS

Deyde, VM., et al., "Crimean-Congo Hemorrhagic Fever Virus Genomics and Global Diversity," *Journal of Virology*, vol. 80, No. 17 (Sep. 2006).

Dilcher, M. et al., "Genetic characterization of Erve virus, a European Nairovirus distantly related to Crimean-Congo hemorrhagic fever virus," *Virus Genes*, (2012) 7 pages.

Duh et al., "The complete genome sequence of a Crimean-Congo hemorrhagic fever virus isolated from an endemic region in Kosovo," *Virology Journal*, vol. 5, No. 7 (Jan. 2008) 6 pages.

James et al., "Structural Basis for the Removal of Ubiquitin and Interferon-Simulated Gene 15 by a Viral Ovarian Tumor Domain-Containing Protease," *Proceedings of the National Academy of Sciences*, 108(6): 2222-2227 (2011).

Keshtkar-Jahromi et al., "Crimean-Congo hemorrhagic fever: current and future prospects of vaccines and therapies," *Antiviral Res.*, vol. 90, No. 2 (May 2011) 8 pages.

Khan et al., "Viral Hemorrhagic Fevers," *Seminars in Pediatric Infectious Diseases*, vol. 8, No. 1 (Jan. 1997) 10 pages.

Martins, RM., et al., "17DD yellow fever vaccine: A double blind, randomized clinical trial of immunogenicity and safety on a dose-response study," *Human Vaccines & Immunotherapeutics*, vol. 9, No. 4 (Apr. 2013).

Schwedt et al., "Thunderclap Headache," *Lancet Neurology*, vol. 5, No. 7 (Jul. 2006) 10 pages.

Woessner et al., "The Erve Virus: Possible Mode of Transmission and Reservoir," *Infection*, vol. 28 (2000) 2 pages.

Yadav et al, "Genomic analysis reveals Nairobi sheep disease virus to be highly diverse and present in both Africa, and in India in the form of the Ganjam virus variant," *Infection Genetics and Evolution*, vol. 11 Issue 5, (Jul. 2011) 10 pages.

Attood, The Babel of bioinformatics, *Science*, 290 (5491):471-473.

Baker et al., "Protein Structure Prediction and Structural Genomics", *Science*, 294: 93-96 (Oct. 5, 2001).

Horning et al., "Regulation of AMPA Receptor Gating by Ligand Binding Core Dimers", *Neuron*, 41:379-388 (Feb. 5, 2004).

Messaoudi et al., "Immunological features underlying viral hemorrhagic", *Current Opinion in Immunology*, 36: 38-46 (2015).

Holzer, et al., "Inhibition of Interferon Induction and Action by the Nairovirus Nairobi Sheep Disease Virus/Ganjam Virus," *PLoS ONE*, vol. 6(12), e28594, pp. 1-12 (2011).

\* cited by examiner

Crimean-Congo hemorrhagic fever (CCHF)
(-) ssRNA Viral Genome

- Glycoprotein (Gn and Gc)
- M segment
- S segment
- Polymerase (L)
- Genomic RNA
- Nucleoprotein (N)
- Ribonucleocapsid (RNP)
- L segment N — vOTU — Viral RNA Polymerase — C
1    169 ~ 600-760                  3,945

Viral Zone 2010 Swiss Institute of Bioinformatics

ATTENUATED LIVE VACCINE FOR CRIMEAN-CONGO HEMORRHAGIC FEVER VIRUS AND ERVE VIRUS

CROSS-REFERENCES TO RELATED APPLICATIONS

This application is a National Stage of International Application No. PCT/US2013/054760, filed Aug. 13, 2013, and which claims the priority benefit of U.S. utility application Ser. No. 13/829,105, filed Mar. 14, 2013; and U.S. provisional application 61/683,132, filed Aug. 14, 2012. The priority applications are hereby incorporated herein by reference in their entirety for all purposes.

GOVERNMENT SUPPORT

This invention was made in part with government support under NIH 1R03AI092249-01 awarded by the National Institutes of Health. The government has certain rights in the invention.

REFERENCE TO A "SEQUENCE LISTING," A TABLE, OR A COMPUTER PROGRAM LISTING APPENDIX SUBMITTED AS AN ASCII TEXT FILE

The Sequence Listing written in file U.S. Pat. No. 934,365_ST25.TXT, created on Jul. 7, 2014, 108,900 bytes, machine format IBM-PC, MS-Windows operating system, is hereby incorporated by reference in its entirety for all purposes.

FIELD OF THE INVENTION

This application relates generally to the field of viral disease, prophylaxis, and vaccination. More specifically, it provides virus vaccines modeled on the etiologic agent for Crimean-Congo hemorrhagic fever and the putative etiologic agent for thunderclap headaches. The vaccines are produced by reducing the deubiquinating and deISGylating activities from the viral OTU protease.

BACKGROUND

Crimean-Congo hemorrhagic fever (CCHF) is a widespread tick-borne viral disease that can affect humans. It is a member of the Bunyaviridae family of RNA viruses. Clinical disease is rare in infected mammals, but it is commonly severe in infected humans. Outbreaks of illness are usually attributable to handling infected animals or people.

The causative organism is found in Asia, Eastern Europe, the Middle East, a belt across central Africa and South Africa and Madagascar. The main environmental reservoir and vector for the virus is hard ticks. Ticks carry the virus to domestic animal stock. Sheep, goats and cattle can develop viremia, but tend not to fall ill. Tick species that have been identified as infected with this virus include *Argas reflexus, Hyalomma anatolicum, Hyalomma detritum, Hyalomma marginatum* and *Rhipicephalus sanguineus*.

The onset of CCHF is sudden, with initial signs and symptoms including headache, high fever, back pain, joint pain, stomach pain, and vomiting. Red eyes, a flushed face, a red throat, and petechiae (red spots) on the palate are common Symptoms may also include jaundice, and in severe cases, changes in mood and sensory perception. As the illness progresses, large areas of severe bruising, severe nosebleeds, and uncontrolled bleeding at injection sites can be seen, beginning on about the fourth day of illness and lasting for about two weeks.

Animal herders, livestock workers, and slaughterhouses in endemic areas are at risk of CCHF. Healthcare workers in endemic areas are at risk of infection through unprotected contact with infectious blood and body fluids. Individuals and international travelers with contact to livestock in endemic regions may also be exposed. In documented outbreaks of CCHF, fatality rates in hospitalized patients have ranged from 5% to as high as 80%.

Previous attempts to develop preventative treatment are as follows. In a USSR/Bulgarian CCHF vaccine developed in 1974 comprised an inactivated antigen from CCHF virus strain V42/81. It was generated from suckling mouse brain preparations, and so is unsuitable for FDA approval in the U.S. There is also a recombinantly produced construct comprising G1 (Gc), or G2 (Gn) glycoprotein ectodomains or portions thereof. However, no study exists to suggest any efficacy for this approach. Full effectiveness of this construct may be limited to the specific strain where the selected glycoproteins originated. There is no established virus-specific treatment. Ribavirin is thought to be effective in vitro, and has been used in human subjects during outbreaks. There are conflicting reports as to effectiveness, with the more recent ones showing limited to no effectiveness against CCHF virus in vivo.

The Department of Defense views CCHF virus as a potential threat to the U.S. armed forces when operating in countries endemic to the virus. These geographical locations include but are not limited to Afghanistan, Pakistan, and the Middle East. The need for preventative treatment of was underscored by death of a U.S. soldier from CCHF viral infection in 2009.

SUMMARY OF THE INVENTION

This invention provides a genetically modified hemorrhagic fever virus that has a viral ovarian tumor protease with decreased ability to remove ubiquitin (Ub) and ISG15 tags from proteins in the cells it infects. Unlike complete knockout strains, the modified virus retains enough activity for replication in a human cell line. This creates an immunogenic and non-pathogenic virus that can be used as an effective live vaccine agent.

One aspect of this invention is a pharmaceutical composition effective in eliciting a specific immune response, that is capable of replication in human cells, but that has been recombinantly altered to have decreased deubiquinating activity or decreased deISGylating activity while maintaining protease activity. Any hemorrhagic fever virus, nairovirus, or a member of the Bunyaviridae family of RNA viruses can be tested for suitability of this invention. A non-limiting example is Crimean-Congo hemorrhagic fever (CCHF) virus, which is used to illustrate the more general aspects of the invention in this disclosure.

Immunogenic compositions of this type can be recombinantly altered to have decreased deubiquitinating activity and/or decreased deISGylating activity. Typically, a lower level of deubiquitinating activity and a lower level of deISGylating activity remain in the mutant virus so that the virus can replicate in a suitable host cell: for example, less than 10%, 5%, or 2% of the activity of either or both deubiquitinating activity and deISGylating activity.

By way of illustration, the immunogenic composition may be modified at position 13, position 77, or both position 13 and 77 of the L-protein. Position 13 of the L-protein may be changed to arginine; position 77 may be changed to aspartic acid. The immunogenic composition may further comprising an adjuvant. After modification, the vOTU protein may have no ability or a reduced ability to inhibit expression of interferon β.

A related aspect of the invention is a recombinant nairovirus (exemplified by but not limited to CCHF virus) that has been modified to have both decreased deubiquinating activity and decreased deISGylating activity, and that is capable of replication in human cells. The invention includes other viruses that have been recombinantly engineered or mutated to reduce deubiquinating and deISGylating activity. This includes Dugbe virus (DUGV), Hazara (HAZV), Nairobi sheep disease virus (NSDV), Ganjam virus (GANV), or any virus that causes febrile illness of varying severity in humans, pets, and agricultural animals. Also included is the Erve Virus (ERVEV), implicated as a cause or promoting agent for severe (so-called "thunderclap") headaches.

Other aspects of the invention are methods for eliciting a specific immune response, preventing or treating hemorrhagic fever and headaches induced by nairovirus using a recombinant virus or immunogenic composition. Also provided are methods for preparing a commercial product wherein a composition or virus is packaged with information on use.

This invention also provides a method of developing an immunogenic but substantially non-pathogenic hemorrhagic fever virus. A host cell is transfected with the genome of a wild-type hemorrhagic fever virus along with genetic material comprised of a codon optimized L-protein. The genome has one or more genetic alterations introduced before transfection. Viral particles are recovered, and then tested and selected for decreased deubiquitinating activity and/or decreased deISGylating activity. The method may entail transfecting the host cell with the L, M, and S gene sectors in separate vectors.

Another aspect of the invention is a method for preparing a commercial product. A vaccine or pharmaceutical composition of the invention is packaged with information on how to use the product for eliciting an immune response or for preventing or treating hemorrhagic fever.

Other aspects of the invention will be apparent from the description that follows.

DESCRIPTION OF THE DRAWINGS

FIG. 1 depicts structural features of CCHF virus and other nairovirus related diseases.

FIG. 4 shows the reverse genetics method developed to produce recombinant CCHF virus in T7 RNA pol. expressing cells.

FIG. 13 compares the three-dimensional structure of the vOTU protein in CCHF and Dugbe nairoviruses.

FIG. 14 shows that residues P77 and I13 are highly conserved amongst strains of CCHFV (top) (SEQ ID NO: 7-SEQ ID NO: 15) and other nairoviruses (bottom) SEQ ID NO: 16-SEQ ID NO: 25, particularly those known to cause human disease.

DETAILED DESCRIPTION

Context

Figure 2:
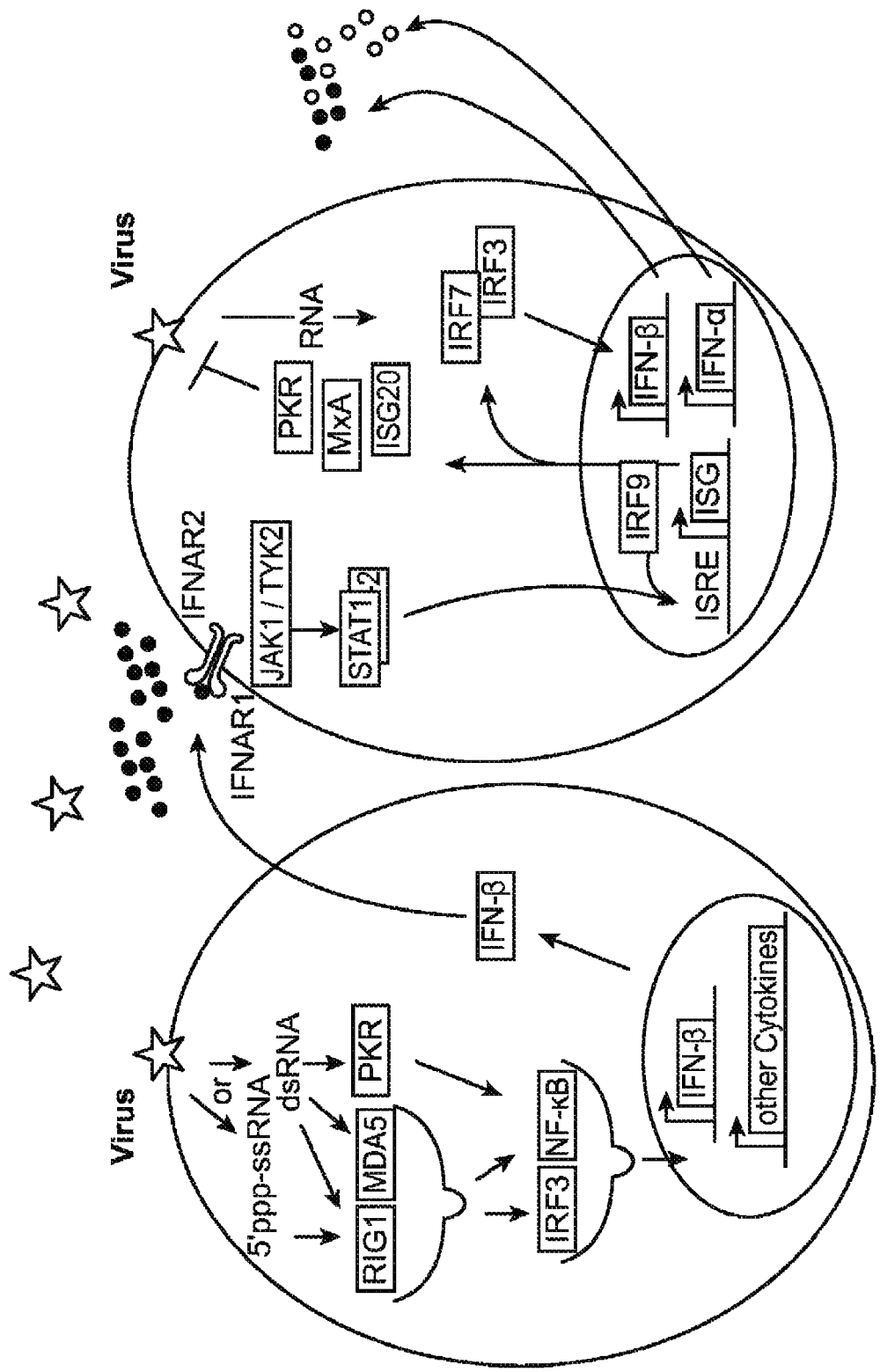
FIG. 2 illustrates the molecular pathway and modulation of the innate interferon (IFN) type 1 mediated immune response.

The Crimean-Congo hemorrhagic fever (CCHF) virus is a member of the genus Nairovirus, family Bunyaviridae. The negative sense RNA genome is composed of three segments—Small (S), Middle (M) and Large (L). The L segment is 11-14.4 kilobases in length while the M and S segments are 4.4-6.3 and 1.7-2.1 kilobases long respectively. The L segment encodes the RNA polymerase; the M segment encodes the envelope proteins (Gc and Gn); and the S segment encodes the nucleocapsid protein. The envelope protein is initially translated as a glycoprotein precursor which is then cleaved into the mature structural glycoprotein products (Gn and Gc) and non-structural glycoproteins.

CCHF virus infection is associated with high case fatality rates in humans. Mertens et al., Antiviral Res. 98(2):248-260, 2013. It is not the only nairovirus that causes human disease. Dugbe virus (DUGV), Hazara (HAZV), Nairobi sheep disease virus (NSDV), and Ganjam virus (GANV) all result in varying severity of febrile illness and are located in a subset of countries within the CCHFV endemic region. Additionally, infection with NSDV and the closely related GANV in sheep negatively impacts local economies through high livestock mortality and limiting of trade with the affected areas. ERVEV (Erve virus, a European nairovirus) has been identified in Germany, France, Netherlands, and the Czech Republic. It is increasingly implicated as the causative agent of severe headaches, known as thunderclap headaches, which result from subarachnoid hemorrhages in humans. M. Dilcher et al., Virus Genes 45:426-432, 2012.

Further information about these viruses is provided by Yadav, P. D. et al., Infect Genet Evol 11, 1111-1120, 2011; Dilcher, M. et al., Virus Genes, 2012/08/07; Schwedt, T. J. et al., Lancet Neurol 5, 621-631, 2006; and Woessner, R. et al., Infection 28, 164-166, 2000. Further information on the CCHF virus as a model for other viruses in this family, including its structure, and biology, can be found in the following publications: Khan A, et al. Viral Hemorrhagic Fevers. Seminars in Pediatric Infectious Diseases. Philadelphia: WB Saunders Co., 1997; 8 (suppl 1):64-73; Peters C J. Viral Hemorrhagic Fevers. Viral Pathogenesis. New York: Lippincott-Raven Publishers, 1997:779-794.

Ubiquitin is a small intracellular protein that becomes conjugated to and marks proteins for destructinon or for transport to particular compartments inside the cell. Ubiquitination is an enzymatic post-translational modification process in which the carboxylic acid of the terminal glycine in activated ubiquitin is catalyzed to form an amide bond to the epsilon amine of the lysine in the modified protein.

Interferon-induced 17 kDa protein ISG15 is a protein that is expressed in resonse to interferon. ISG15 shares several properties with other ubiquitin-like molecules. Its activity is tightly regulated by specific signaling pathways that have a role in innate immunity. It also has cytokine activity. The mechanism of ISGylation is similar to that of ubiquitination.

Wild-type hemorrhagic fever viruses have both deubiquinating and deISGylating activity to reverse labeling by ubiquitin and ISG15 as part of its arsenal of weaponry that it brings to bear upon infection of the host.

Overview of the Invention

It has now been discovered that impairment but not elimination of the ability of the virus to remove ubiquitin (Ub) and ISG15 tags creates an immunogenic and non-pathogenic virus that can be used as an effective live vaccine agent.

Post-translational modification of host proteins by ubiquitin (Ub) and Ub-like interferon simulated gene product 15 (ISG15) known as ubiquitination and ISGylation, respectively, is a way that the human organism tags proteins for removal and degradation. Ubiquitin is a small regulatory protein found in almost all tissues that directs protein recycling by attaching to proteins and labeling them for destruction. The ubiquitin tag directs proteins to the proteasome, which is a large protein complex in the cell that degrades and recycles unneeded proteins. Interferon-induced 17 kDa protein is a protein that in humans is encoded by the ISG15 gene. ISG15 shares several common properties with other ubiquitin-like molecules (UBLs), but its activity is tightly regulated by specific signaling pathways that have a role in innate immunity Upon interferon treatment, ISG15 can be detected in both free and conjugated forms, and is secreted from monocytes and lymphocytes where it can function as a cytokine.

CCHF virus, the Erve virus, and other nairoviruses including Dugbe virus (DUGV), Hazara (HAZV), Nairobi sheep disease virus (NSDV), and Ganjam virus (GANV) possesses a protease (specifically, the viral ovarian tumor domain protease) that performs deubiquitination and deISGylation functions. This enables the virus to evade the human immune response by down-regulating immunological functions such as expression of interferon as well as other antiviral effector and signaling proteins. However, complete loss of function of this protease results in the inability of CCHF virus and likely other nairoviruses to replicate. This prevents viruses that have been genetically modified to eliminate these activities entirely from being useful as a self-propagating vaccine agent.

The genetically modified virus of this invention possesses a viral ovarian tumor protease with significantly less deubiquitination and deISGylation activity, while still retaining enough activity for virus production in a human cell line. The modified virus will not efficiently evade the human immune response, but will generate a level of immunity in the host that protects against future infection by a wild-type virus.

Development of Modified Strains of Virus

The invention described in this disclosure was developed using recombinantly sourced Crimean-Congo hemorrhagic fever virus as a model. The model CCHF virus strain was recovered from hamster cell line (BSR/T7) and propagated in human cell lines. Selective mutations were generated that result in the simultaneous ablation of the greater than 95% deubiquinating and deISGylating in vitro activity of virus's viral ovarian tumor domain protease.

Reverse genetic derived infectious Crimean-Congo hemorrhagic fever virus strain IbAr10200 may be achieved by first cloning the originating virus's cDNA, or by completing gene synthesis, of the complete segments (S, M and L). The S, M, and L segments were cloned in the pT7 vector between a T7 promoter, to drive the transcription of Crimean-Congo hemorrhagic fever virus complementary genome RNA copies, and a hepatitis D ribozyme, to obtain authentic 3' termini. The vectors were transfected into BSR/T7 cells to obtain recombinant RNA genome matching the cloned sequence. Complementation of the with mammalian expression vectors pCAGGS encoding a human codon optimized L-protein (pC-L) and wild-type N protein (pC-N) is used to obtain recombinant virus.

Details were as follows: Wild recombinant CCHF virus was rescued by transfecting a 10 cm$^2$ well of subconfluent BSRT7/5 cells with 2.5 µg pT7-S, 1 µg pT7-M, 1 µg pT7-L, 0.66 µg of pC-N and 0.33 µg of human codon optimized pC-L mixed with 11 µL of Mirus LT1™ transfection reagent (Mirus Bio LLC, Madison, Wis.) in OPTI-MEM™ media. All viruses recovered were harvested from cell supernatants four days post transfection and amplified in SW13 cells.

A CCHF vOTU expression construct was obtained by use of an *Escherichia coli* BL21 codon-optimized synthesis of the first 169 amino acids from the L protein in CCHF virus (GenBank accession no. AAQ98866.2) by Biobasic, Inc. Along with the vOTU portion of the L protein, six histidine codons and a stop codon were added to the gene in order to provide a C terminus histidine tag. The resulting gene was incorporated into a pET11a plasmid using NdeI and BamHI restriction sites. Site directed mutagenasis of the construct was performed using a QuikChange™ kit. Successful mutations were confirmed by sequencing performed by Genscript™. The mutated constructs were then transformed into BL21(DE3) cells, and were grown at 37° C. in 6 L of LB broth containing 100 µg/mL of ampicillin until the optical density at 600 nm reached 0.6. Expression of wild type (WT) or mutant CCHF vOTU was induced by the addition of IPTG to a final concentration of 0.8 mM. The culture was further grown for 4 hrs at 37° C. and then centrifuged at 6,000×g for 10 minutes. Cells were collected and stored at −80° C. until use. vOTUs were purified according to a standard protocol and assayed for activity.

CCHFV L amino acid positions 13 and 77 were mutated to isoleucine and aspartic acid and replaced the wild type pT7-L vector in the transfection plasmid mix. Four days following the transfection, immunoreactive foci can be detected and recovery of infectious recombinant Crimean-Congo hemorrhagic fever virus was confirmed by passing the transfection supernatants to SW13 cells. Three days later, cytopathic effect can be evident and Crimean-Congo hemorrhagic fever virus antigens can be detected throughout a cell monolayer.

Mutation of the 13$^{th}$ and 77$^{th}$ amino acid positions within their L-protein to isoleucine and aspartic acid respectively create a mutant lacking significant Ub and ISG15 activity, while maintaining activity to cleave a peptide. Aberration of complete activity of the viral ovarian tumor domain protease that is located in 1-169 amino acids of the L-protein by a mutation of position 40 from cysteine to alanine results in no recombinant virus.

Mutation of position 77 of the L-protein to aspartic acid results in the viral ovarian tumor protease of Crimean-Congo hemorrhagic fever virus strains is necessary to disrupt a hydrophobic interaction between it and human interferon stimulated gene product 15. This significantly reduces the ability of the viral ovarian tumor protease to recognize stimulated gene product 15.

To remove deubiquitinating activity, mutation of position 13 of the L-protein to arginine interferes through charge repulsion with an arginine at position 42 in ubiquitin and a tryptophan at position 123 in interferon stimulated gene product 15. This double mutation reduces deubiquitinating and deISGylating activities to 2% and 3% that of wild-type viral ovarian tumor protease, respectively, while maintaining catalytic activity greater than 88% that of wild-type viral ovarian tumor protease in vitro.

To construct the recombinant virus, the gene encoding native L-protein is altered at position 77 and position 13 of the amino acid sequence to delete the residue or substitute a residue or plurality of residues that is different from the native sequence. For example, the amino acid substitution at position 13 in the L-protein could be lysine or histidine. The amino acid substitution at position 77 in the L-protein could be other amino acids with a polar or charged side chain.

The I13R/P77D double mutation eliminates CCHF virus's viral ovarian tumor (vOTU) domain protease from performing deubiquitinating and deISGylating activity, but it still allows the virus to replicate. The CCHF virus with the I13R/P77D changes maintains one or more critical innate immunity biomarkers.

Illustrations

FIG. 1 depicts structural features of CCHF virus and the etiologic agent for other nairovirus related diseases. Rift Valley Fever Virus possesses an S-segment encoded NSs virulence factor, which allows for immune system evasion. Removal of NSs results in virus that does not effectively evade immune system. Crimean-Congo hemorrhagic fever (CCHF) virus does not encode a NSs factor, but it does have a vOTU (Viral Ovarian Tumor Domain Protease: see GC Capodagli et al., J Virol. 2011 April; 85(7): 3621-3630).

FIG. 2 illustrates the molecular pathway and modulation of the innate interferon (IFN) type 1 mediated immune response.

Figure 3:
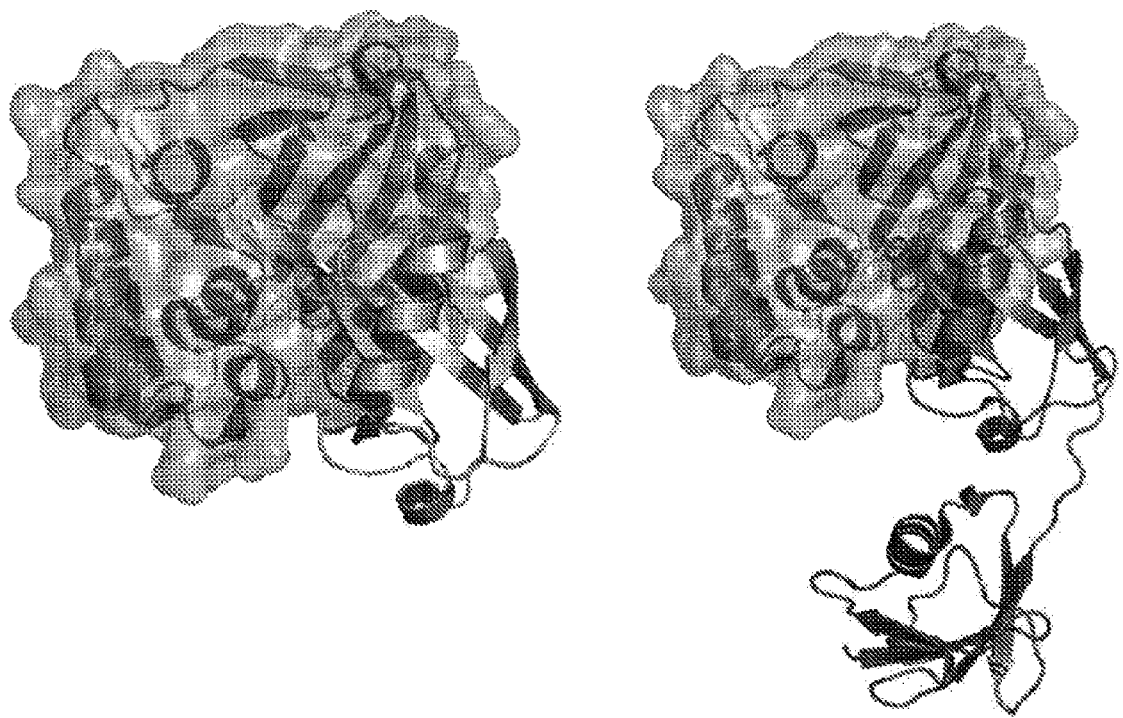
FIG. 3 is a three-dimensional representation of the ubiquitin and ISG15 proteins docking with the Viral Ovarian Tumor Domain Protease (vOTU) of CCHF virus.

FIG. 3 is a three-dimensional representation of the ubiquitin and ISG15 proteins docking with the vOTU protein of CCHF virus, developed from the crystal structure of CCHF virus determined by Capodagli et al. supra.

Figure 4:
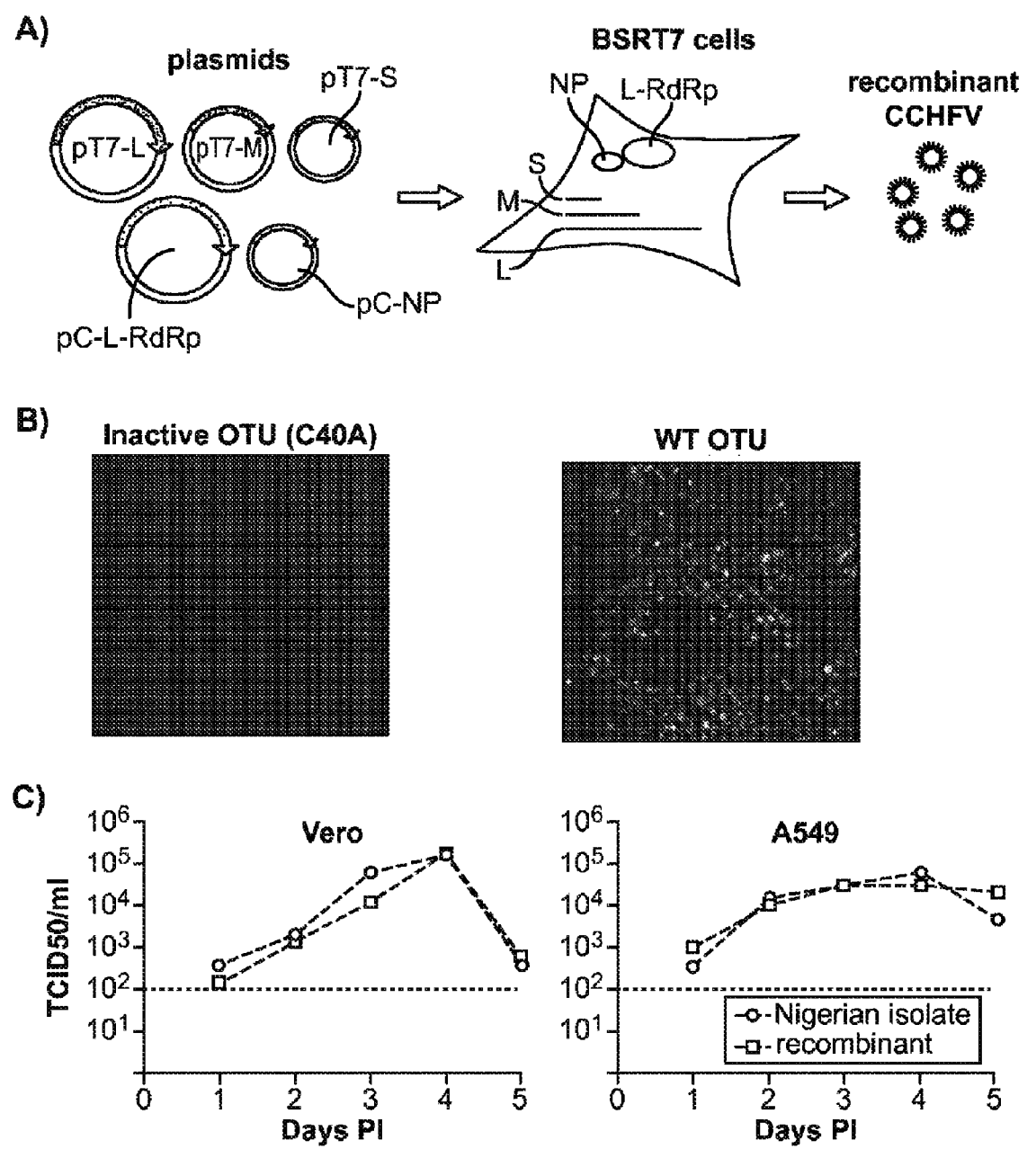
Figure 5:
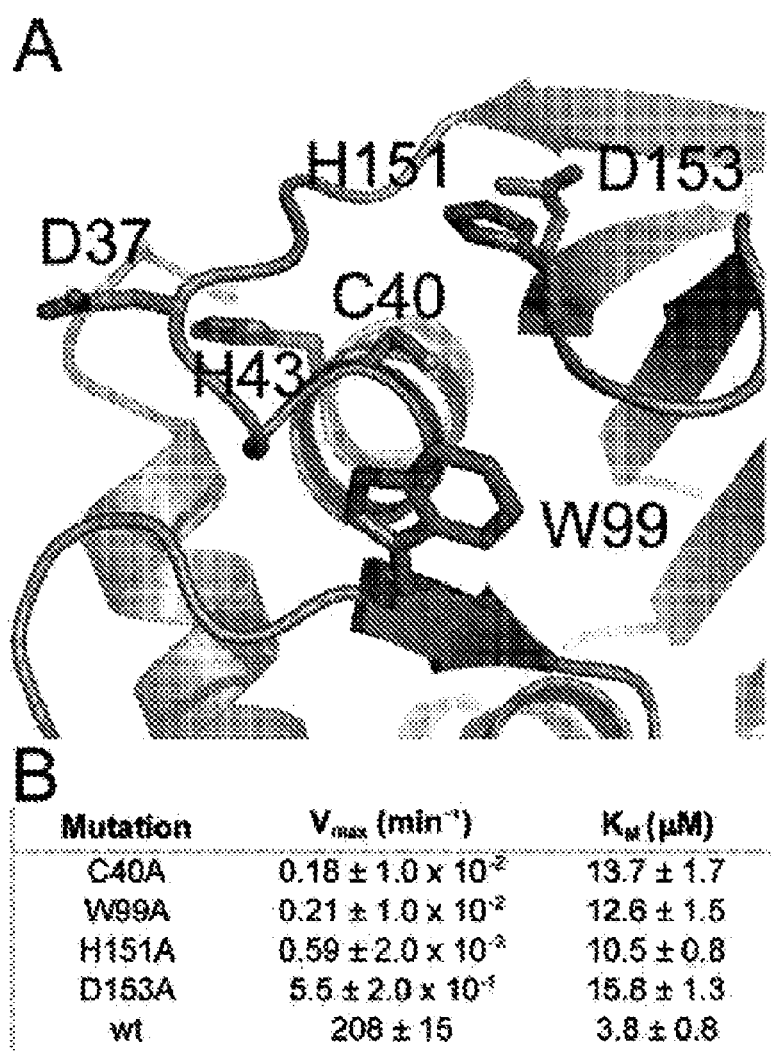
FIG. 5 depicts the active site of vOTU as a three-dimensional rendering.

FIGS. 4 and 5 show the reverse genetics CCHF virus system used for developing the invention. FIG. 4(A) shows the method developed to produce recombinant CCHF virus in T7 RNA pol. expressing cells. The solid arrows depict the genome RNA produce by the T7 ("pT7"), and viral proteins supporting the initial genome replication ("pC"). The panels below show immunofluorescence detection of CCHF virus produced by reverse genetics.

FIG. 5 depicts the active site of vOTU. (A) is a three-dimensional rendering of vOTU's active site, showing secondary structures, helices, and loops. (B) Mono-Ub Km and Vmax constants determined for catalytic triad vOTU mutants.

Figure 6:
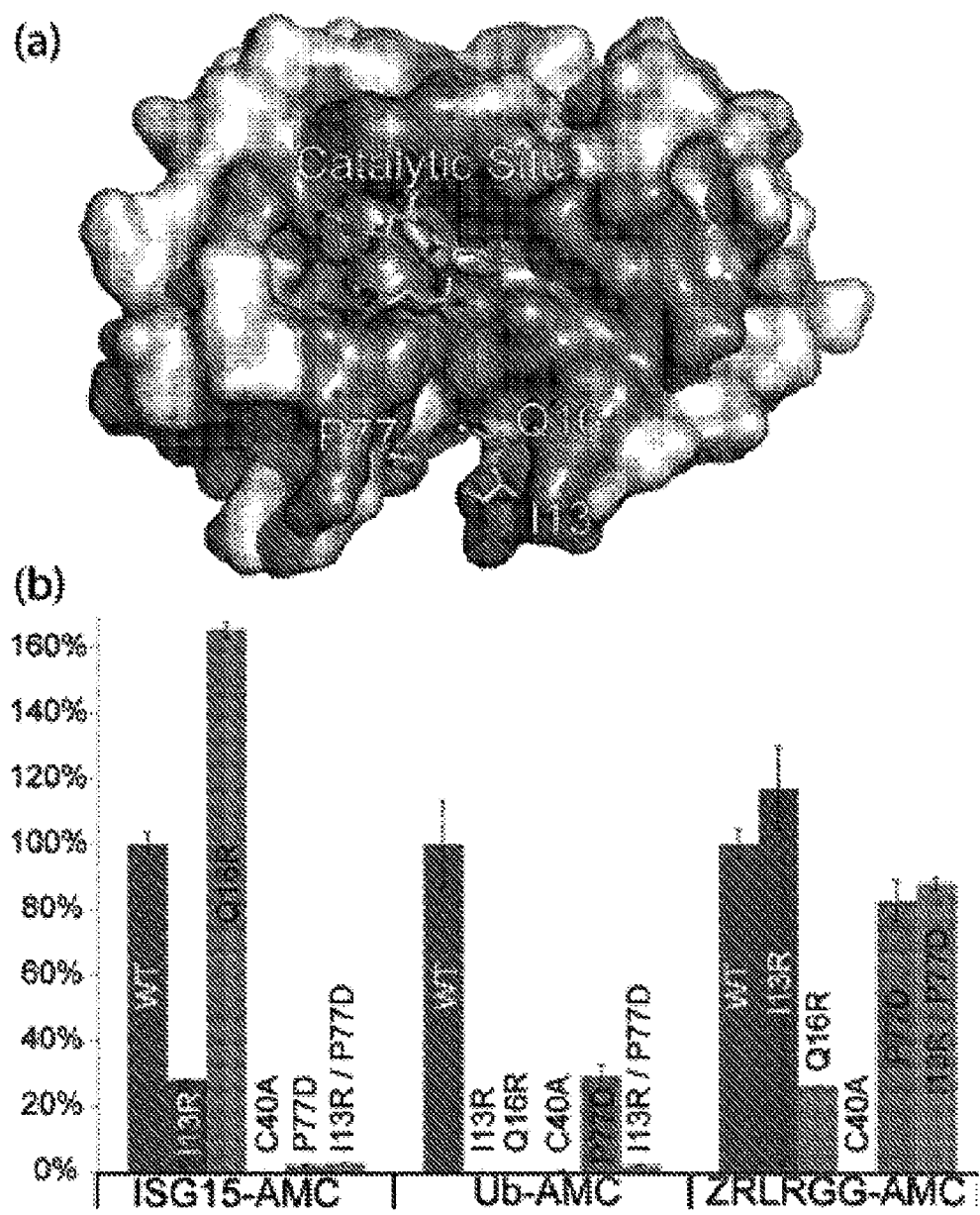
FIG. 6(a) shows the residues selected for mutation as part of the three-dimensional structure of vOTU.
FIG. 6(b) presents data showing disruption of the vOTU deubiquinating and deISGylating activities in vitro

FIG. 6 is taken from the development of CCHF virus vOTU-I13R/P77D. FIG. 6(a) shows data from disruption of the vOTU deubiquitinating and deISGylating activities in vitro. The CCHF virus vOTU is shown with the residues which comprise the complete vOTU/Ub binding interface. Residues Q16 and I13 were selected to disrupt the binding of Ub through site directed mutagenesis. P77 was selected to disrupt binding of ISG15 through mutagenesis. The peptide RLRGG represents the C-terminal tail of Ub and ISG15. FIG. 6(b) shows data from disruption of the vOTU deubiquitinating and deISGylating activities in vitro.

Figure 7:
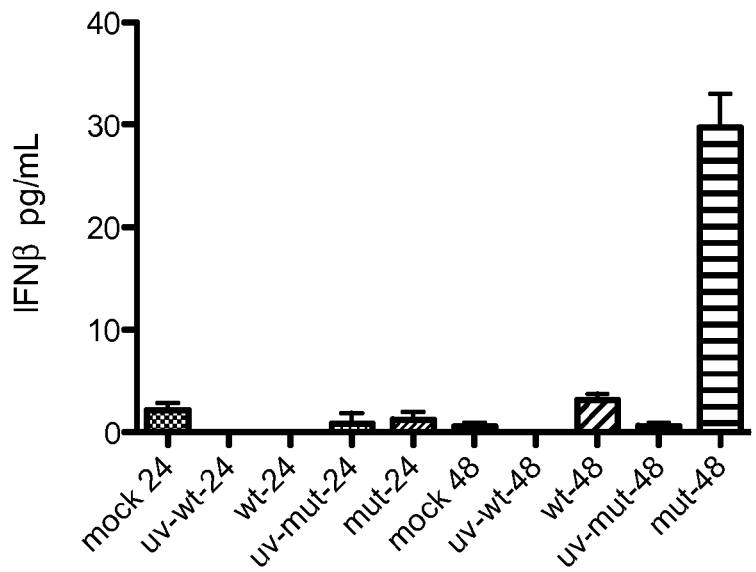
FIG. 7 shows results of monitoring ISGylation of wild type (wt) CCHF virus and reverse genetically produced CCHF virus containing the I13R/P77D mutation.

FIG. 7 shows results of monitoring ISGylation of wild type (wt) CCHF virus and reverse genetically produced CCHF virus containing the I13R/P77D mutation within CCHF virus's vOTU. ISG15 antibodies were used to highlight proteins that have been ISGylated within A549 cells upon mock infection or infection by wt CCHF virus or I13R/P77D CCHF virus. Antiserum specific for CCHF nucleocapsid was used as a control to confirm CCHF virus infection. As mock infection contains no virus, no significant ISGylation occurs. Infection of wt CCHF virus reduces the ISGylation to mock levels where as the CCHF virus containing the I13R/P77D mutation can't reduce intracellular ISGylation levels. The (+) columns denote addition of exogenous interferon to probe to evaluate the extent of CCHF virus vOTU activity.

Figure 8:
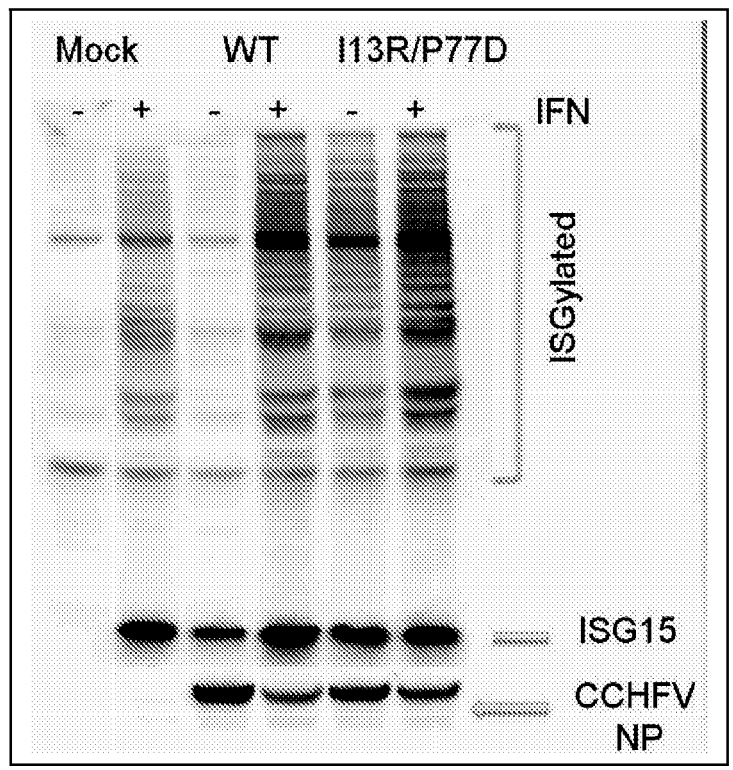
FIG. 8 shows results of an assay for interferon (IFN) beta (β) in cells infected with CCHF virus wild type (WT) and the selected mutant.

In FIG. 8, interferon (IFN) β was monitored from immunocompetent A549 cells that were infected with UV inactivated wt CCHF virus (uv-wt), wt CCHF virus (wt), I13R/P77D CCHF virus (mut). Upon infection, bsrt7 cells are not interferon producing cells, whereas A549 are. 24 and 48 denotes the time points for surveying IFN β production. For uv-wt, the virus is inactivated and incapable of infection, thus no IFN β production. Wild type CCHF virus has a functioning vOTU that suppresses IFN β production. However, I13R/P77D renders CCHF virus's vOTU unable of performing that function resulting in a significantly observable change in IFN β level over 48 hours.

Figure 9:
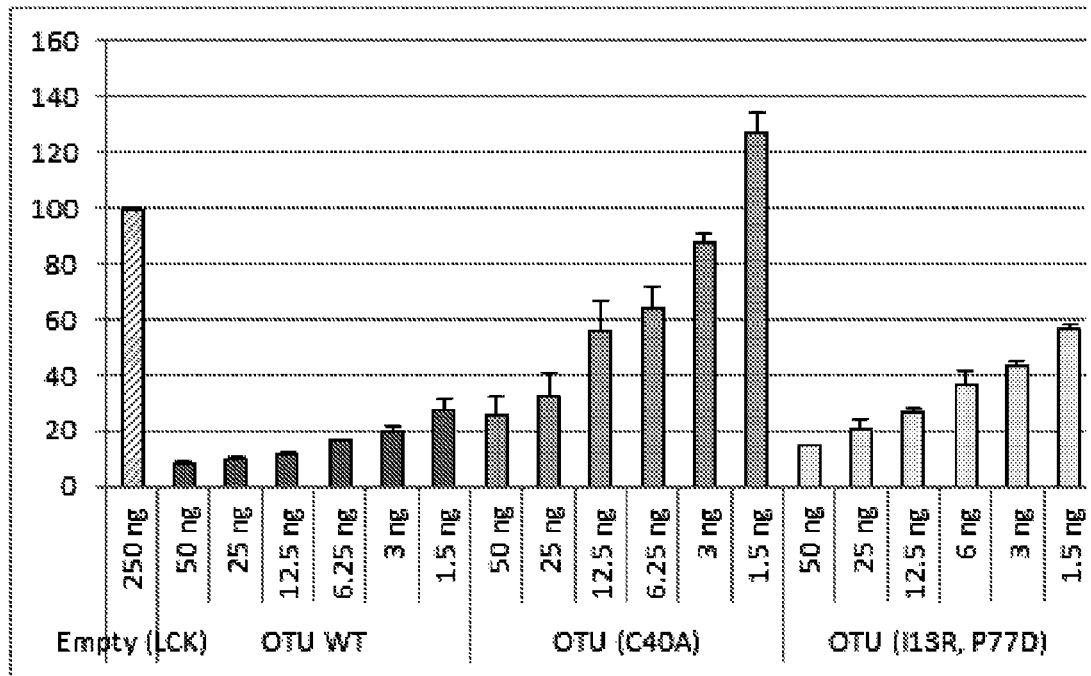
FIG. 9 shows data comparing the ability of the engineered virus with a totally inactive mutant virus (C40A) to inhibit production of interferon beta.
Figure 10:
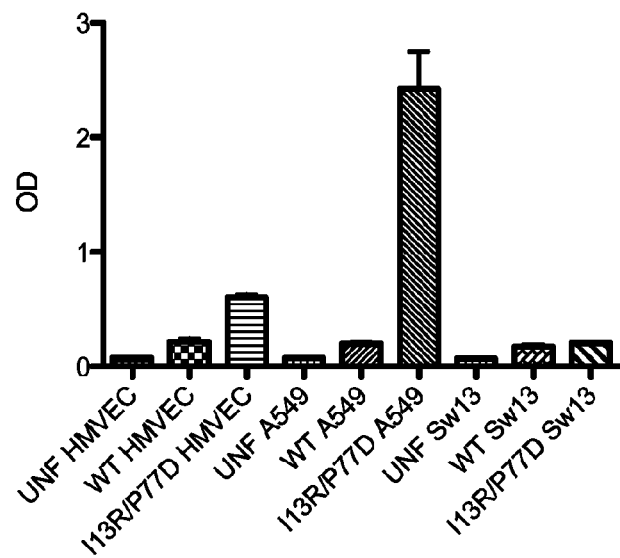
FIG. 10 shows a test for interferon β production in lung carcinoma A549 cells

FIG. 9 shows the reduced ability of transfected I13R/P77D at suppressing the transcription activation of an interferon β promoter relative to a totally inactive mutant (C40A) and wild type (WT) vOTU in human embryonic kidney 293 cells. FIG. 10 shows that I13R/P77D CCHFV lack of ability to suppress human immunity (as measured by interferon β production) is lung carcinoma A549 cells and primary culture of human microvascular endothelial cells (HMVEC).

Figure 11:
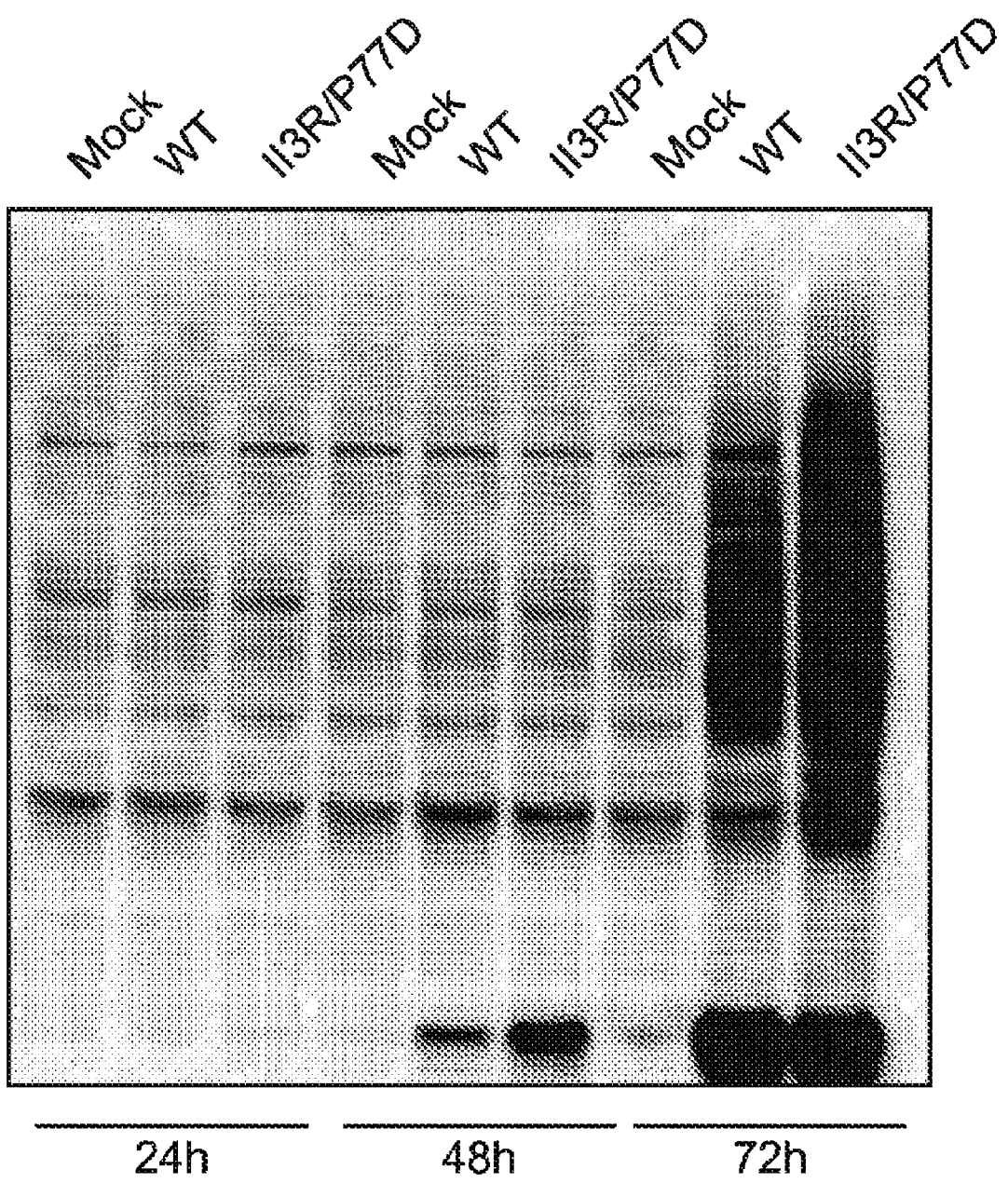
FIG. 11 shows a Western blot testing human ISG15 activity.
Figure 12:
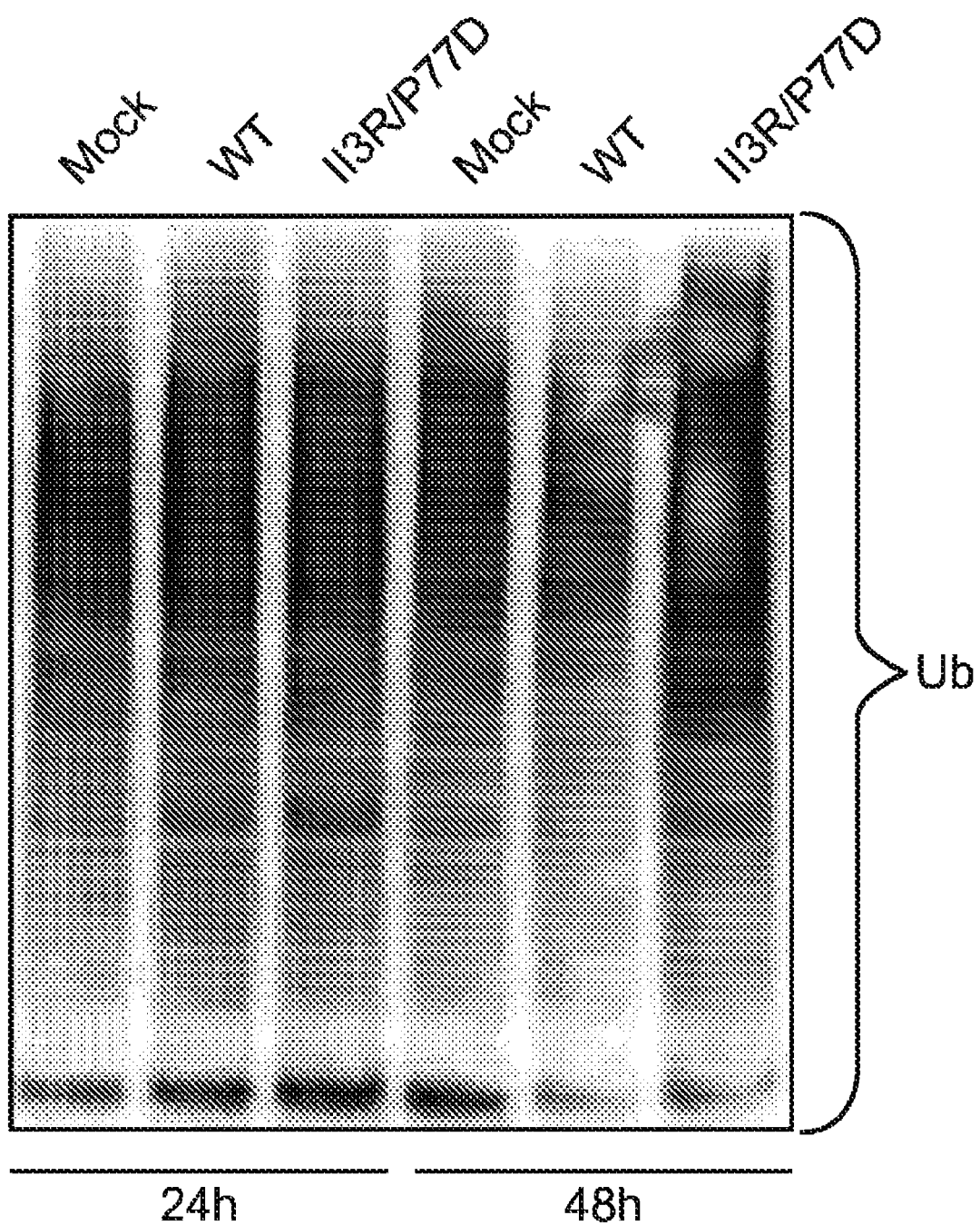
FIG. 12 shows a Western blot of the total levels of cellular protein ubiquitination in cells following infection.

FIG. 11 shows a Western blot for human ISG15 in A549 cells infected with wt CCHFV or I13R/P77D. Mock-infected lanes are also included. Cells infected with I13R/P77D have a significantly higher concentration of ISG15 conjugated proteins (the proteases substrate), then WT (wild type). The mock infected cells have no virus in them, and establish a basal level for ISG15 activity in this assay. FIG. 12 shows a Western blot of the total levels of cellular protein ubiquitination in A549 cells following WT and I13R/P77D infection. This indicates that ubiquitination level is enhanced only by the I13R/P77D infection after 48 h.

Figures 13, 14:
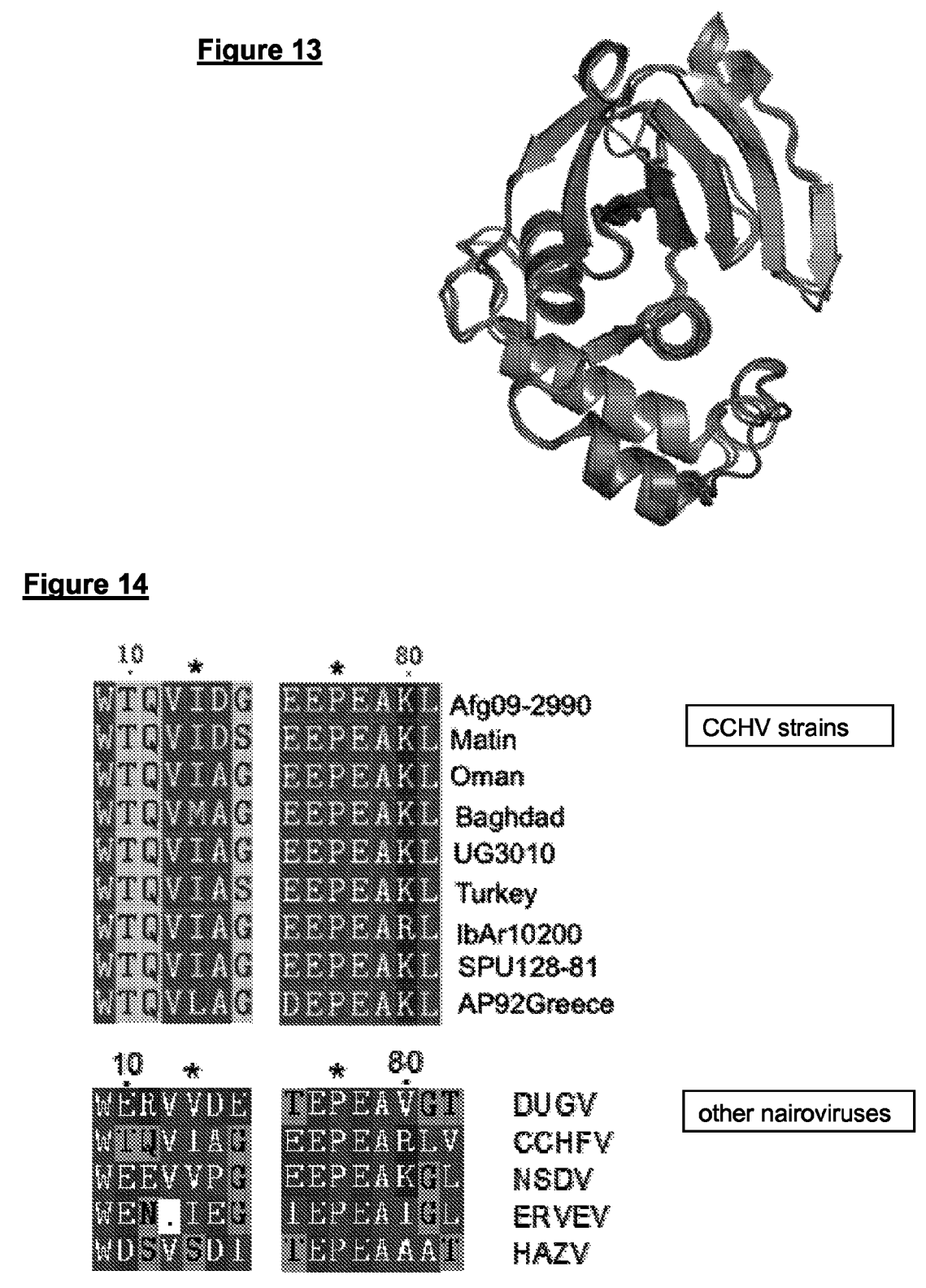

FIG. 13 shows the crystal structure of CCHF vOTU (virus ovarian tumor domain) overlaid with that the recently elucidated vOTU from the Dugbe nairovirus. This illustrates that nairovirus vOTUs have a conserved 3-D structure placing I13R and P77D in the same location throughout nairoviruses vOTUs. Similarly, FIG. 14 shows that P77D and I13R are highly conserved amongst strains of CCHFV (top) and other nairoviruses (bottom), particularly those known to cause human disease, the I13 and P77 amino acid sites are conserved.

This shows the general applicability of this invention to create recombinant forms of any one of these viruses and other homologs to have decreased deubiquitinating and decreased deISGylating activity while maintaining protease activity.

Testing and Commercial Use for Immunization and Treatment

Once a virus according to this invention has been generated and tested in tissue culture, its ability to elicit an immune response and/or prevent viral infection can be tested in a suitable animal model. Suckling mice is a suitable system to test the benefits of the vaccine. For proof of concept, a homologous nairovirus can be used. For NSDV (Nairobi Sheep Disease Virus), sheep are the ideal and easiest test model, since it is often fatal in sheep. For Erve virus, wild-type mouse models can be used. For Dugbe, Hazara, or Erve virus, suckling mice is an accepted model for the safety and efficacy of the vaccine as their immune system is immature.

In any of these models, a suitable end point would be protection, reduced fever, reduced duration of infection, or at least prolonged survival. Blood samples are taken before the testing and periodically after administration to measure antibody response, cellular response, and virus inhibition. An increase in any one or more of these responses is expected to correlate with clinical efficacy. Such experiments can be used not only to test the safety and efficacy of the vaccine in general terms, it can also be used to determine the effective dose.

In general terms, the vaccine is assembled by combining the recombinant virus in a suitable medium or vehicle in accordance with its intended route of administration. The ingredients are compounded into a medicament in accordance with generally accepted procedures for the preparation of pharmaceutical preparations, as described in standard textbooks on the subject. See, for example, Pharmaceutical Preformulation and Formulation A Practical Guide from Candidate Drug Selection to Commercial Dosage Form, M Gibson ed., Informa Health Care 2009, Pharmaceutical Manufacturing Handbook Production and Processes, S C Gad ed., Wiley-Interscience 2008, and the latest edition of Remington's Pharmaceutical Sciences, Maack Publishing Co, Easton Pa.

Steps in the compounding or formulating of the medicament depend in part on the intended use and mode of administration. Typically, the vaccine will be administered intramuscularly, subcutaneously, or orally. It can be prepared for commercial distribution with any of the following procedures in any effective combination: sterilizing, mixing with appropriate non-toxic and non-interfering excipients, buffers and other carriers, lyophilizing or freezing, dividing into dose units, and enclosing in a delivery device The medicament will typically be packaged in a suitable container accompanied by or associated with written information about its intended use, such as prophylaxis or treatment of hemorrhagic fever A suitable agent as the active ingredient is a modified virus according to this invention as a live virus type vaccine. Alternatively, after replicating in culture, the virus can be inactivated with UV irradiation or chemical means, and the viral particles used with a suitable adjuvant. In essence, attenuation of the vOTU could be used as a safeguard to prevent dangerous live wild type CCHFV from escaping physical attenuation methods for making CCHFV vaccines. The physical attenuation would prevent possible reversion of the virus.

The immunogenic compositions of this invention can be used for the purpose of prophylaxis against infection by a nairovirus having the characteristics described, exemplified but not limited to CCHF virus and Erve virus. Once the subject is adequately primed (such as by previous immunization or infection with the target virus), a single administration of the composition may be sufficient to raise a protective immune response. Multiple administrations are more typical in an immunologically naive host. Desirable outcomes include induction or enhancement of a specific antibody response measured by a suitable test, such as enzyme-linked immunosorbant assay (ELISA) using viral antigens, or a virus neutralization assay.

In some circumstances, the immunogenic compositions of this invention can also be used for purposes of treatment or eradication of an ongoing infections disease. In this case, the goal might be to eradicate the virus, or just to manage signs and symptoms of infection: such as fever caused by CCHF virus, or headaches caused by Erve virus. For treatment of an ongoing infection, the immunological objective may be not just to elicit specific antibody, but also to elicit a specific T-lymphocyte response (measured in an ELISPOT™ or proliferation assay), or a cytotoxic T cell response (measurable, for example, in a cytotoxicity assay).

To elicit a therapeutic immunological response in such circumstances, an appropriate treatment regimen may comprise multiple administrations of the antigen-adjuvant composition (at least 2 or 4, for example, on a biweekly schedule). Administration of an immunological composition of this invention could be accompanied by other pharmaceutical agents aimed at inhibition of the causative virus and/or management of symptoms: for example, treatment with antiviral agents and/or small molecule anti-inflammatory agents in the case of CCHF virus; treatment with antiviral agents and/or analgesic for headaches in the case of Erve virus. Clinical benefit would be manifest as a reduction in the titer of virus or infectious particles in blood or in a tissue biopsy, or a limitation in the progression of necrosis, pain, wasting, or other signs of the disease.

Ultimate choice of the treatment protocol, dose, and monitoring is the responsibility of the managing clinician.
Other Genetic Alterations and Other Viruses CCHF virus, Erve virus and the particular mutations I13R/P77D are used throughout the disclosure for purposes of illustration, and not to limit the practice of the invention.

A person practicing the invention may, as an alternative, change I13 and/or P77 to another amino acid, and/or change other residues in the vOTU protein—so long as the resultant virus has decreased deubiquitinating activity and/or decreased deISGylating activity, and is still able to replicate in a suitable host cell.

vOTU variants with reduced enzyme activity can be generated by site-directed mutagenesis to introduce a known change into the primary structure if the wild type virus or another variant. The altered virus is then assayed for activity—namely (and in any combination), deubiquitinating activity, deISGylating activity, vOTU protease activity, ability to replicate, and/or ability to suppress cytokines such as interferon β. Thus, another amino acid can be substituted at positions I13 and/or P77, and/or at positions nearby in the tertiary structure. Possible changes include substitutions of one codon for another, and deletions or additions to the encoded amino acid sequence in any combination. Preferred changes will typically retain the tertiary structure of the wild-type virus. For the influence of vOTU structure on enzyme activity, see Capodagli, Pegan et al., J Virol. 2013; 87(7):3815-27.

vOTU variants with reduced enzyme activity can also be generated by introducing random mutations into the virus, screening colonies with a functional assay, and selecting colonies with the desired level of enzymatic activity. The particular mutation in the selected virus can then be characterized as to what changes have been made to the viral genome.

Because the genomes of nairoviruses are highly conserved, the invention can also be practiced with other strains of CCHF virus and with other nairoviruses. Possible wild-type nairoviruses that can be modified according to this invention are referred to in various places in this disclosure. Included are the following:

Nairobi Sheep Disease (NSDV; Africa) I Ganjam (Indian variant) is a fatal sheep and goat disease that particularly hinders livestock transport in Africa Dugbe virus causes mild flu-like symptoms in humans, goats, and sheep. It is present in various parts of Africa and Asia, such as Hazara, Kupe, Dera Ghazi Khan, Hughes, Qalyub, Sakhalin, and Thiafora.

FIGS. 13 and 14 show that quite a number of CCHF viral strains and other nairoviruses are conserved at amino acid positions 13 and 77. Accordingly, the same genetic alterations should have the same biological effects: reduced deubiquitinating and deISGylating activity, while still allowing the virus to replicate.

Besides site directed and random mutagenesis, vOTU variants with reduced enzyme activity can be obtained by building a hybrid virus in which the wild type glycoprotein (M segment) of a nairovirus is replaced with the M segment of another virus having the desired functionality—such as the CCHF I13R/P77D double mutant.

Directed or random changes to a nairovirus genome, and genetic alterations in nairoviruses other than CCHF virus, can be initially screened and tested for vOTU function using assays for deubiquitinating activity and/or deISGylating activity. By way of illustration, a suitable assay for deubiquitination and deISGylation activity can be run as follows. Typically, assays are performed in duplicate in 100 mM NaCl, 50 mM HEPES pH 7.5, 0.01 mg/mL bovine serum albumin (BSA), and mM DTT. A suitable microtiter plate is Corning Costar™ half-volume black 96-well plate with a reaction volume of 50 µL. The reactions are observed with a matching plate reader, such as an Infinite™ M1000 series reader (Tecan, Inc.). The reaction is followed using ubiquitin or other vOTU substrate conjugated to a fluorescent tag, such as 7-amino-4-methylcourmarin (AMC). AMC becomes fluorescent (excitation λ, 360 nm; emission, 460 nm) upon decoupling from the ubiquitin or ISG15.

Suitable substrate conjugates are Ub-AMC, human ISG15-AMC (hISG15-AMC), (Boston Biochem, Mass.) and ZRLRGG-AMC (SEQ ID NO: 26)(Bachem). ZRLRGG is a hexapeptide homologous the carboxy terminal of ubiquitin. Release of AMC is monitored by combining the substrate with wild type (WT) or mutant CCHF vOTU. The extinction coefficients for all three fluorescent substrates can be determined by adding excess vOTU to various concentrations of each substrate and allowing the reactions to run to completion. The resulting maximum fluorescence values are plotted to determine the slope and consequently each substrate's extinction coefficient. Suitable substrate concentrations to measure turnover rates in this assay are of the order of 1 µM hISG15-AMC with 20 nM vOTU; 1 µM hUb-AMC with 4 nM vOTU, and 50 µM ZRLRGG-AMC with 4 µM vOTU from either wild type or genetically altered virus.

Advantages

In summary, this invention provides a new technology to produce replicating viral particles suitable for use in a vaccine. Advantages include the following:

Nairoviruses with selective mutations can now be produced in human cell lines, avoiding xenogeneic antigen contaminants from animal tissue. Examples include but are not limited to CCHF virus and the Erve virus.

Proven structurally biology-guided mutations of viral ovarian tumor domain proteases ablate deubiquitinating and deISGylating activity.

The recombinant system methodology of this invention can be used to recombinantly generate any nairovirus, or CCHF virus strain. because of the homology.

The method of genetic modification through ablation of deubiquitinating and deISGylating activity can be used in conjunction with physical attenuation methods to ensure a greater level of public safety when administering the vaccine.

```
SEQUENCES
Reverse genetics system generated Crimean-Congo hemorrhagic fever virus's L-Protein
amino acid sequence
                                                                        (SEQ. ID NO: 1)
MDFLRSLDWTQVRAGQYVSNPRFNISDYFEIVRQPGDGNCFYHSIAELTMPNKTDHSYHYIKRLTESAARKYYQEEDEARLVGL SLEDYLKRMLSDNEWGSTLEASMLAKEMGITIIIWTVAASDEVEAGIKFGDGDVFTAVNLLHSGQTHFDALRILPQFETDTREA LSLMDRVIAVDQLTSSSSDELQDYEDLALALTSAEESNRRSSLDEVTLSKKQAEILRQKASQLSKLVNKSQNIPTRVGRVLDCM FNCKLCVEISADTLILRPESKEKIGEIMSLRQLGHKLLTRDKQIKQEFSRMKLYVTKDLLDHLDVGGLLRAAFPGTGIERHMQL LHSEMILDICTVSLGVMLSTFLYGSNNKNKKKFITNCLLSTALSGKKVYKVLGNLGNELLYKAPRKALATVCSALFGKQINKLQ NCFRTISPVSLLALRNLDFDCLSVQDYNGMIENMSKLDNTDVEFNHREIADLNQLTSRLITLRKEKDTDLLKQWFPESDLTRRS IRNAANAEEFVISEFFKKKDIMKFISTSGRAMSAGKIGNVLSYAHNLYLSKSSLNMTSEDISQLLIEIKRLYALQEDSEVEPIA IICDGIESNMKQLFAILPPDCARECEVLFDDIRNSPTHSTAWKHALRLKGTAYEGLFANCYGWQYIPEDIKPSLTMLIQTLFPD KFEDFLDRTQLHPEFRDLTPDFSLTQKVHFKRNQIPSVENVQISIDATLPESVEAVPVTERKMFPLPETPLSEVHSIERIMENF TRLMHGGRLSTKKRDGDPAEQGNQQSITEHESSSISAFKDYGERGIVEENHMKFSGEDQLETRQLLLVEVGFQTDIDGKIRTDH KKWKDILKLLELLGIKCSFIACADCSSTPPDRWWITEDRVRVLKNSVSFLFNKLSRNSPTEVTDIVVGAISTQKVRSYLKAGTA TKTPVSTKDVLETWEKMKEHILNRPTGLTLPTSLEQAMRKGLVEGVVISKEGSESCINMLKENLDRITDEFERTKFKHELTQNI TTSEKMLLSWLSEDIKSSRCGECLSNIKKAVDETANLSEKIELLAYNLQLTNHCSNCHPNGVNISNTSNVCKRCPKIEVVSHCE NKGFEDSNECLTDLDRLVRLTLPGKTEKERRVKRNVEYLIKLMMSMSGIDCIKYPTGQLITHGRVSAKHNDGNLKDRSDDDQRL AEKIDTVRKELSESKLKDYSTYARGVISNSLKNLSRQGKSKCSVPRSWLEKVLFDLKVPTKDEEVLINIRNSLKARSEFVRNND
```

-continued

KLLIRSKEELKKCFDVQSFKLKKNKQPVPFQVDCILFKEVAAECMKRYIGTPYEGIVDTLVSLINVLTRFTWFQEVVLYGKICE
TFLRCCTEFNRSGVKLVKIRHCNINLSVKLPSNKKENMLCCLYSGNMELLQGPFYLNRRQAVLGSSYLYIVITLYIQVLQQYRC
LEVINSVSEKTLQDIENHSMTLLEDSFREITFALEGRFEESYKIRTSRCRASGNFLNRSSRDHFISVVSGLNLVYGFLIKDNLL
ANSQQQNKQLQMLRFGMLAGLSRLVCPNELGKKFSTSCRRIEDNIARLYLQTSIYCSVRDVEDNVKHWKQRDLCPEVTIPCFTV
YGTFVNSDRQLIFDIYNVHIYNKEMDNFDEGCISVLEETAERHMLWELDLMNSLCSDEKKDTRTARLLLGCPNVRKAANREGKK
LLKLNSDTSTDTQSIASEVSDRRSYSSSKSRIRSIFGRYNSQKKPFELRSGLEVFNDPFNDYQQAITDICQFSEYTPNKESILK
DCLQIIRKNPSHTMGSFELIQAISEFGMSKFPPENIDKARRDPKNWVSISEVTETTSIVASPRTHMMLKDCFKIILGTENKKIV
KMLRGKLKKLGAISTNIEIGKRDCLDLLSTVDGLTDQQKENIVNGIFEPSKLSFYHWKELVKKNIDEVLLTEDGNLIFCWLKTI
SSSVKGSLKKRLKFMNIHSPELMPENCLFSSEEFNELIKLKKLLLNEQQDEQELKQDLLISSWIKCITACKDFASINDKIQKFI
YHLSEELYDIRLQHLELSKLKQEHPSVSFTKEEVLIKRLEKNFLKQHNLEIMETVNLVFFAALSAPWCLHYKALESYLVRHPEI
LDCGSKEDCKLTLLDLSVSKLLVCLYQKDDEELINSSSLKLGFLVKYVVTLFTSNGEPFSLSLNDGGLDLDLHKTTDEKLLHQT
KIVFAKIGLSGNSYDFIWTTQMIANSNFNVCKRLTGRSTGERLPRSVRSKVIYEMVKLVGETGMAILQQLAFAQALNYEHRFYA
VLAPKAQLGGARDLLVQETGTKVMHATTEMFSRNLLKTTSDDGLTNPHLKETILNVGLDCLANMRNLDGKPISEGSNLVNFYKV
ICISGDNTKWGPIHCCSFFSGMMQQVLKNVPDWCSFYKLTFIKNLCRQVEIPAGSIKKILNVLRYRLCSKGGVEQHSEEDLRRL
LTDNLDSWDGNDTVKFLVTTYISKGLMALNSYNHMGQGIHHATSSVLTSLAAVLFEELAIFYLKRSLPQTTVHVEHAGSSDDYA
KCIVVTGILSKELYSQYDETFWKHACRLKNFTAAVQRCCQMKDSAKTLVSDCFLEFYSEFMMGYRVTPAVIKFMFTGLINSSVT
SPQSLMQACQVSSQQAMYNSVPLVTNTAFTLLRQQIFFNHVEDFIRRYGILTLGTLSPFGRLFVPTYSGLASSTVALEDAEVIA
RAAQTLQMNSVSIQSSSLTTLDSLGRSRTSSTAEDSSSVSDTTAASHDSGSSSSSFSFELNRPLSETELQFIKALSSLKSTQAC
EVIQNRITCLYCNSNECPLDRHNVIYSSRMADSCDWLKDGKRRGNLELANRIQSVLCILIAGYYRSFCGEGTEKQVKASLNRDD
NKIIEDPMIQLIPEKLRRELERLGVSRMEVDELMPSISPDDTLAQLVAKKLISLNVSTEEYSAEVSRLKQTLTARNVLHGLAGG
IKELSLPIYTIFMKSYFFKDNVFLSLTDRWSTKHSTNYRDSCGKQLKGRIITKYTHWLDTFLGCSVSINRHTTVKEPSLFNPNI
RCVNLITFEDGLRELSVIQSHLKVFENEFTNLNLQFSDPNRQKLRIVESRPAESELEANRAVIVKTKLFSATEQVRLSNNPAVV
MGYLLDESAISEVKPTKVDFSNLLKDRFKIMQFFPSVFTLIKMLTDESSDSEKSGLSPDLQQVARYSNHLTLLSRMIQQAKPTV
TVFYMLKGNLMNTEPTVAELVSYGIKEGRFFRLSDTGVDASTYSVKYWKILHCISAIGCLPLSQADKSSLLMSFLNWRVNMDIR
TSDCPLSSHEASILSEFDGQVIANILASELSSVKRDSEREGLTDLLDYLNSPTELLKKKPYLGTTCKFNTWCDSNRSCKFTYSS
RSGESICIFIAGKLHIHLSSESVALLCETERQVLSWMSKRRTEVITKEQHQLFLSLLPQSHECLQKHKDGSALSVIPDSSNPRL
LKFVPLKKGLAVVKIKKQILTVKKQVVFDAESEPRLQWGHGCLSIVYDETDTQTTYHENLLKVKHLVDCSTDRKKLLPQSVFSD
SKVVLSRIKFKTELLLNSLTLLHCFLKHAPSDAIMEVESKSSLLHKYLKSGGVRQRNTEVLFREKLNKVVIKDNLBQGVEEEIE
FCNNLTKTVSENPLPLSCWSEVQNYTEDIGFNNVLVNIDRNTVKSELLWKFTLDTNVSTTSTIKDVRTLVSYVSTETIPKFLLA
FLLYEEVLMNLINQCKAVKELINSTGLSDLELESLLTLCAFYFQSECSKRDGPRCSFAALLSLIHEDWQRIGKNILVRANNELG
DVSLKVNIVLVPLKDMSKPKSERVVMARRSLNHALSLMFLDEMSLPELKSLSVNCKMGNFEGQECFEFTILKDNSARLDYNKLI
DHCVDMEKKREAVRAVEDLILMLTGRAVKPSAVTQFVHGDEQCQEQISLDDLMANDTVTDFPDREAEALKTGNLGFNWDSD

Reverse genetics system generated Crimean-Congo hemorrhagic fever virus's M-Protein
amino acid sequence
(SEQ. ID NO: 2)
MHISLMYAILCLQLCGLGETHGSHNETRHNKTDTMTTPGDNPSSEPPVSTALSITLDPSTVTPTTPASGLEGSGEVYTSPPITT
GSLPLSETTPELPVTTGTDTLSAGDVDPSTQTAGGTSAPTVRTSLPNSPSTPSTPQDTHHPVRNLLSVTSPGPDETSTPSGTGK
ESSATSSPHPVSNRPPTPPATAQGPTENDSHNATEHPESLTQSATPGLMTSPTQIVHPQSATPITVQOTHPSPTNRSKRNLKME
IILTLSQCLKKYYGKILRLLQLTLEEDTECLLEWCKRNLGLDCDDTFFQKRIEEFFITCECHFNEVLQFRTPGTLSTTESTPAG
LPTAEPFKSYFAKGFLSIDSGYYSAKCYSGTSNSGLQLINITRHSTRIVDTPGPKITNLKTINCINLKASIFKEHREVEINVLL
PQVAVNLSNCHVVIKSHVCDYSLDIDGAVRLPHIYHEGVFIPGTYKIVIDKKNKLNDRCTLFTDCVIKGREVRKGQSVLRQYKT
EIRIGKASTGSRRLLSEEPSDDCISRTQLLRTETAEIHCDNYGGPGDKITICNGSTIVDQRLCSELGCYTINRVRSFKLCENSA

```
-continued
TGKNCEIDSVPVKCRQGYCLRITQEGRGHVKLSRGSEVVLDACDTSCEIMIPKGTGDILVDCSGGQQHFLKDNLIDLGCPKIPL LGKMAIYICRMSNHPKTTMAFLFWFSFGYVITCILCKAIFYLLIIVGTLGKRLKQYRELKPQTCTICETTPVNAIDAEMHDLNC SYNICPYCASRLTSDGLARHVICKPKRKEKVEETELYLNLERIPWVVRKLLQVSESTGVALKRSSWLIVLLVLFTVSLSPVQSA PIGQGKTIEAYRAREGYTSICLFVLGSILFIVSCLMKGLVDSVGNSFFPGLSICKTCSISSINGFEIESHKCYCSLFCCPYCRH CSTDKEIHKLHLSICKKRKKGSNVMLAVCKLMCFRATMEVSNRALFIRSIINTTFVLCILILAVCVVSTSAVEMENLPAGTWER EEDLTNFCHQECQVTETECLCPYEALVLRKPLFLDSTAKGMKNLLNSTSLETSLSIEAPWGAINVQSTYKPTVSTANIALSWSS VEHRGNKILVSGRSESIMKLEERTGISWDLGVEDASESKLLTVSVMDLSQMYSPVFEYLSGDRQVGEWPKATCTGDCPERCGCT SSTCLHKEWPHSRNWRCNPTVCWGVGTGCTCCGLDVKDLFTDYMFVKWKVEYIKTEAIVCVELTSQERQCSLIEAGTRFNLGPV TITLSEPRNIQQKLPPEIITLHPRIEEGFFDLMHVQKVLSASTVCKLQSCTHGVPCDLQVYHIGNLLKGDKVNGHLIHKIEPHF NTSWMSWDGCDLDYYCNMGDWPSCTYTGVTQHNHASFVNNLNIETDYTKNFHFHSKRVTAHGDTPQLDLKARPTYGAGEITVLV EVADMELHTKKIEISGLKFASLACTGCYACSSGISCKVRIHVDEPDELTVHVKSDDPDVVAASSSLMARKLEFGTDSTFKAFSA MPKTSLCFYIVEREHCKSCSEEDTKKCVNTKLEQPQSILIEHKGTIIGKQNSTCTAKASCWLESVKSFFYGLKNMLSGIFGNVF MGIFLFLAPFILLILFFMFGWRILFCFKCCRRTRGLFKYRHLKDDEETGYRRIIEKLNNKKGKNKLLDGERLADRRIAELFSTK

THIG

Reverse genetics system generated Crimean-Congo hemorrhagic fever virus's S-Protein
amino acid sequence
                                                               (SEQ. ID NO: 3)
MENKIEVNNKDEMNRWFEEFKKGNGLVDTFTNSYSFCESVPNLDRFVFQMASATDDAQKDSIYASALVEATKFCAPIYECAWVS STGIVKKGLEWFEKNAGTIKSWDESYTELKVDVPKIEQLTGYQQAALKWRKDIGFRVNANTAALSNKVLAEYKVPGEIVMSVKE MLSDMIRRRNLILNRGGDENPRGPVSHEHVDWCREFVKGKYIMAFNPPWGDINKSGRSGIALVATGLAKLAETEGKGIFDEAKK TVEALNGYLDKHKDEVDRASADSMITNLLKHIAKAQELYKNSSALRAQSAQIDTAFSSYYWLYKAGVTPETFPTVSQFLFELGK QPRGTKKMKKALLSTPMKWGKKLYELFADDSFQQNRIYMHPAVLTAGRISEMGVCFGTIPVANPDDAAQGSGHTKSILNLRTNT

ETNNPCAKTIVKLFEVQKTGFNIQDMDIVASEHLLHQSLVGKQSPFQNAYNVKGNATSANII

Erve virus segment L, complete sequence-GenBank Accession JF911697.1
                                                               (SEQ. ID NO: 4)
MDAVNRLDAIVWENIEGNLSRAFLTLDLHAFFNVNKEVGDGNCFYRALSRLHSESRTSNEHLYYRLLIPDAVDKYFDIEPEAIG LGLNKQEYVSKAILDGEWAGSLEASMLSKFLDITIIIWIVDDSGTIISANRYGEGRPSQAYNLCMVGNAHFDSLYIRVFERPET ANLSLIGRLESIEELASLEEIPCLSSREESHQNSSGGRRRELSKLEVRAIENSQGIPLRIGRIVELLFSCRLGFSIDHKSLKIT ILDDSKYDVLDIRKLGHYLLTNDRKLKREYSKCGLEIDNSVWPHLDESYLLRFAFPGYGLHRFIPMLLPIFVEDVLKVCLSILL SSFLYKSKVKYKREFIINCCRSTVTSGKRVFKSIRKATTSNLYSAPQLVLRSCCEHLYKRLIVKITSSIKAMSGESHLLLRNLD FSSLSLADYLKLLTALAKEDLQDQSFINKELISLNRLNKTLKEIKDNGLWETKEKEEVISKFFEEKNMLKFIGKSGKASGSFQI GNVLAYAHNLYLNKDSLGLSNDDMEQISIEIRKLQLLQEGETFDPVAIICNKLEGHFNKAFSKLPKICQSECHVLFDDIRNSSN HAAAWKHALRLKGTMYEGFFSQHNNWTYIPEDLKPSLMMAIQTLFPEKFVRFLEKTQLHPEFRDLVPDFLITQRLLMEGDNPKV NISHQLKVIEGLQESVESIPMGDQKIFPLPEVAVSEVRSIEGILNRIETQARQSNSKNNRFHTETNNVVLDQERSYSTHQLLFI EVGYQTDVEGKVLTDTVKWKEVLKLLAILDIKATLLVCADNSKTHVNDWWIDEELVRLLKGSISHLFSKLSKNTPMEVTDIVVG SISTQKIRSFLKSGTSTKTPLSTKDVQETWHAMKDHILNRETGVQLGEKYANPMYIGLVEGVTMTDEGVQLIMNLLKDNIKTLT DEFEKTRYKHEINKSIETGSKMVLAWLKEDLEGCRCIKCISEVLTSVDDVVAVGSKLSILARACSLSSHPVCCHSETINVVNSS NFQKRTPDLSSINHLSIKSLDDDEGSITDLDKLIRLTLPGKTEKEKKIKRSVDCLIKLMMFKSSINCIKLPSGQIVMLDKNTRS NITKSRDPSLDGKAGKFTASREETVLKNLSSQKLSNYSDYVKQVISSSIKNVANQQASNCKLNDLWVEKLVNDLDVPLQNEEVI EKVKRSVEQRKKYIRNNDKLIIRSTHEMISYLTNFRGSLCAEPSNRLFSVDCVLFKEVISEAMLRYQSTAYQGCVDHMLKLLEL LLEFTWFQEVLVYSKVCETFLRICTEFNRAGLKLLKVRHLNINIAVKLPANKKQNMQCRIYDHNMQHLTDVFFLNRRQAIIGAA YPYILLVLYIQILQQQRCIEELDNRSSHVQGIRNKSDKLLTCFMNEAASVLNGHFEEAYKERFQICKLSGNFSTKPPHENFINV FAGLNLVYGVIMRDSFLANSQPQNKQLQMLRYGMLNGLSRLSCPLELGKKFSSSCRRIEDNLSRVYLQSTIYCSMRDVEKNVPA
```

-continued

WKEVDLCPSVTIPCFSIYGLFVNSDRQLIFDIYNVHIYNKEMDNFDEGCISVLEETADRHMNWELDLEKNWRDDHDQRGTRLLL
GIPNVHKSKCQDPRQIEDSKSDASSLKDSCLTRRSSSSNRLSTSSLINRYTTIIKPIEIDSGIFLESDILRQGRASATGGPKYY
AYTPNKASILKDCLTIIKKNPNYTFGSFEVIQAVTEFARSKYPQENICKAKRDPKNWVSISEVTETTSIVATPKTEFYVKDCFK
TNISNQNKKLSKMIKNKFKKLGSLFSDNDISKKDCTVLLSTVDGLTAKQKQDITNAVFEPSKLSLYNWSYILTKGVFDVLLTHD
GNIIYCWIKSLSLMAKSRLRKHLSFMSVGNDTVPEEGFFSSNEIESLITIRRLLICEEHEEISTICASNLVSAWIKCIFVKPID
DVYNDKLLSDMLSAAEELYTLRLKHMILIRDKKENSYTSFIKEELILKGEERVFLKNYDKLIVKSVNFLLFAAVSAPWCMHYKA
LESYIVKHPEILDIGDTETYSNSILSLTLSNVVYELYKIYCGKKKEVVDKRKMISLRFFVRYLTTMFASNSEPFSTSLNEDEID
VGKTNDIEEKLLSQTKLVFAKLGLGDKNYDFIWTVQMIANSNFNVCKKLTGRSEGERLPRSIRSKVVYEMVKLVGESGMAILQQ
LAFAKSLNYNHRFFSVLAPKAQLGGSRDLLVQETGTKIIHAATESFSRSLLRTTNDDGLTNQNLKETVLNHALDTLTTMRSVDG
ELLKGSSNLIQFYKVICISGDNTKWGPIHCCSFFSGMMQQLLKDHPDWSAFYRLTFIKNLCRQIEIPAASIKKIINVAKLKMEH
NQDIDCLSEEQAQDLLKESADDWSALPYVKFLIKTYLRKGKLAMNSYNHMGQGIHHATSSILTSIMAETFEELCTHYFKSIFPN
LTVDINHAGSSDDYAKTIIVTGVLDREQYELYDSIFWNHACRFKNYIAAVNRCCQMKDSAKTLVGDCFLEFYSEFMMGYRVTPA
VIKFIFTGLMNSSVTSPSSLTQACHVSSQQAMYNSVPMLTNITFTLCRQQMFFNHVEGFIRKFGPLTLGSVSQFGRLYCPRYSN
LVNTSVTIEDCESIVNACNSILKWNDLFETLAKSEIEEEFEKDRSKRSLSSSETSSFKSGESSTEFSFIHRRLLTDDELKFIDI
SSECARYTNAQAVEERLGLYYWDTRDQNPKNKDFILNSTLCNSCEWIKKGKDKCALEAIVRIQMLLRLLCFGHYRSFSGQGLER
QVKSSLNRDENQIIEDPMIQLIPEKLRRELERLGLSKMSVEELLPKSLSCSSICQVVAHRLISLNVSTESYVAEVSRLKQTLTA
RNVLFGLAGGIKELSIPIYTIFMKSYFFKDNVFMDLTDRWLTQHSANYRDSSGKKLDGKIVTKYPHWLSVFMNCLVSMDSTSEL
TDKSLFNDSLKCIGVTRNLNNQRMLTIIKSHLESVSSELKYFILQFSNLNRRKMRIVESRPAECEMEANKVVITKSSLFTAGDG
VKLNNNPAVVIGFLLDESSISEVKPSRVDFANLMKDRFKLSQYFPSVDLVLKSLKRESDQHLQVCSTPDYSVSTKYVNYLTLLC
RMMIQTNSSLTVFYMIKSNKLRNEPTVSDLISYGIKEGRYLKLPEAEIDTSTYSVKYWKIIQCISCIGLLPMSDSSRRDILFGF
MNWKVTCCGDSGCPIFKEEASVLSEFNNQTILHVLASEVHLIKDKHERESIINLVDYVTSPSELIKKKPYLGTTASFKTWGGGG
REGRFTYSSRSGESTGIFVGGKLHIYLSNDTISLLDEVERNVLGWLSQRRTEIFTIEQHESFVNLLPSIAEFGSKSSDGKVVGV
AVDKSNPRFLRYTDPKGSAKNHILRIKKQILTVKKINTVEFESDPKLVWSKSGVSIVFDEISTEVTYHERIGLIKGLLANVIEN
KTLPSLYQDTQICLSKLKFSNTILMNSIALLHAYLVHAPLDAFNSVGSKRTVLKTFLENRLLVQSEGQTVKQTFGAADLHFHKQ
TPHNSEAMTLLTISKTLTENMLPFDSWPEVQAQLETCGLSNFLLTFKSEPAKGYLMWDLQTSLVPDRLKILDIKDVVSSVNSGV
LVPAFLPFLFEPALLKELTNTSLAALHTLSSLSITNEQVDRIVISTIYCFQTETKERSSLKFRPSSLLGLCQRQTFRIGNRLEV
SAVADFDEVSLMITIRCTDPQDQSMPRDKKQLRIIKNFNSSVRCLMIDQSVDVKKIKESFNDLTMESDHKGTKIKFTAKPNDNN
QFDYLALMYEGKERLAEYTSIANFVLFLLGCKHNSFEEPNTIKGEEDISIDSIIDVVETINEQVFQDEPVRLSDKVYFSDDEY

Erve virus segment M, complete sequence-GenBank Accession: JF911698.1
(SEQ. ID NO: 5)
MVTKWVVAAVLVIKWCLLMKVTLSSTISTTPTTSTTNSTQSTNNTNATSSAPNSTQPNTTSSPGSTNQTLNASSSSNQTQQEIA
RSVVNYTSGEWAPTLEALYTSGSPCDKLNKSWCKLEVGKTHGLSPYVKHLYNLSYDGYNALCETKKGNYGFVWKWKFTFTVTTG
PERVLLRDVQCSNVVYDGITKDGYLIHFLFGGRRVHFTDCKYAVITKNCKIESSKDGPVPLAGYGNWTTATYSLFLQNKYANEA
CKIKFPCLNKGKALGNGGFELKGYFTTGLTRPETSGRRLLSTGDSEPEDDCGTHSHMKQITNHHLITDFKDGPGDVVSICNGTH
FFHGRMPNNLGCYSIRSIKVSHHCGHHKTKCTIEPELKQCSHGKCISIRMSNKGIVRLSRGSSTETIKCGTECLIPPLDGEGDI
IVDCPGGTQHFLQRNIVDLDCPTYPYFQEFMLYICRASHRPKTTIGFFLWMSVGYIILSACCSFTLLLLRLLCKGVELCKTRFT
STQEVCEVCKQQISGNLSKQLHEANCKNGLCPYCSNRLPESSLYKHAEVCPRKKPTVEAIREHENYNSTPWLFVFIFGVSEYSG
TLIKRSVWIIVLLSLLLVALSPVYGEQDFLFEGIGEEQLEKGLWEDEVELVEGCHQECFVVEAECLCPSFQAGRQLLFYHLMNK
QIRTSNKLKLLSSVSLETPWGVVKIEKGFKPTSSMANLQLSWSSEEEVGGKVILSGRSTSIIKLKERTGMVWELSSSRASEKKK
LVVSIMDFSQEYKTQFQYLTGDRLVSEWPRATCTGPCPDRCACHTSTCTWKTWPNSRKWTCNPTWCWGVGTGCTCCGMDVEKPF
QNYLVAKWSTEYIKTDVIVCVEVSEEERHCDLIQAGSRFHLGPITVLVSDPQSVAKKLPSEVITLHKVQGGEVDLMHVNKILTA -continued

```
NSLCKPQSCTHGSPGDIQIFKPDYLVKYSISKRINAIEDHSWANDTWMSWQGSDLDYYCTTGSWPTCTFSGVVKQNSDAFKNLE

TLEFNLMEEFFFHSSRVEVKGSTLGFPVKSRPKEGGGELSVLVEVNGLELHSKLIDPLGLSLKITSCKGCYSCSSGFYCDVVLN

IEEPSEMTVHVECNNPNIVLTESSLIAKSGALSASKVKGFSALRETRLCLILQESKVTKKEVKDCIDIKLEEPKDVIIERGSTL

LSHQNDTCTSGFGCWLGNAKSFSLGLGMMFQNYFGSIIIGLIIFVLPVIALLVFFCLGKRILICRRLKHCFRSNLEDKQKFKQL

LTELKHSNLLKIMKEDAKSSWRGLANKALGKTPKMD

Erve virus segment S, complete sequence-Genbank Accession: JF911699.1
                                                                  (SEQ. ID NO: 6)
MENLIDFSGRDGLDRWLRATFPDVILSVGLTNYGSLMTSVPDLSHFEQMARQAKSEQEKDAVYSKALTEATRKAAPIAACALTS SKEMVKKGLQWFEDQIISEDGNFLVWHQNYEQLKKAPPSFEQLMGYQMSALNWRQSVGYGQLEETAVLVSQVIAQFSVPGTLVV TVQEMIKDMIARRGGGPKRGVSEEHVRCCVDIMNGNLSALINPAWGDIDKKNKNGLMLLTTGIAKLRELYGPAAMVKVQQAADK FGEWGKAQDVLDQSRVQEIHQVLLKSIAESTSLGGGAAVFKNQIAQIDSVFSSYYWMWRAGITPESFPLLSDFLFELGQNARGS AKIIKTLDRIGLKWSKPLVNLFADSTFKMGRIHMHPAILTTGRLNEMGLCFGIIPASHPESAVNGSGFAKNILNVRTDGMNPSA QLIVQLFDIQRQSRTLSDLDVVSSEHLFHQILVGKRTAYQNAFQVKGNATDTKIVGFDPPKIDKNKAIRDAVDQHLMASGYAVA PERSVMDLRREMEEREHKQRLEALAARAREAEAWEASRRAEMIQKRSGVRGGPTVQTQTLTVQEQYTIPKPMQSPQVQLMGAQG

SVQYLGAGAQQPSDPWFQSQASATSIPQQLPTEDYTTINLFK
```

* * *

Each and every publication and patent document cited herein is incorporated herein by reference as if each such publication or document was specifically and individually indicated to be incorporated herein by reference.

While the invention has been described with reference to the specific embodiments, changes can be made and equivalents can be substituted to adapt to a particular context or intended use, thereby achieving benefits of the invention without departing from the scope of what is claimed.

The invention claimed is:

1. An immunogenic composition effective in eliciting a specific immune response, comprising recombinantly altered nairovirus comprising an L protein that has been recombinantly altered to have decreased deubiquinating activity or decreased deISGylating activity while maintaining protease activity, such that the nairovirus replicates in human cells, wherein the recombinantly altered L protein is altered at least at one amino acid position corresponding to a ubiquitin or ISG15 substrate binding interface of vOTU domain protease, wherein the amino acid position corresponds to position 13 or position 77 of the L-protein of Crimean Congo hemorrhagic fever (CCHF) virus.

2. The immunogenic composition of claim 1, wherein the nairovirus has been recombinantly altered to have both decreased deubiquinating activity and decreased deISGylating activity.

3. The immunogenic composition of claim 1, wherein the nairovirus is a hemorrhagic fever virus.

4. The immunogenic composition of claim 1, wherein the nairovirus is an Erve virus.

5. The immunogenic composition of claim 4, wherein the Erve virus has been modified at position(s) corresponding to position 13, or positions 13 and 77 of the L-protein of Crimean Congo hemorrhagic fever (CCHF) virus.

6. The immunogenic composition of claim 5, wherein the position corresponding to position 13 of the L-protein of Crimean Congo hemorrhagic fever (CCHF) virus is changed to arginine.

7. The immunogenic composition of claim 5, wherein the position corresponding to position 77 of the L-protein of Crimean Congo hemorrhagic fever (CCHF) virus is changed to aspartic acid.

8. The immunogenic composition of claim 1, further comprising an adjuvant.

9. A recombinantly altered nairovirus comprising an L protein that has been recombinantly altered to have decreased deubiquinating activity or decreased deISGylating activity while maintaining protease activity, such that the nairovirus replicates in human cells, wherein the recombinantly altered L protein is altered at least at one amino acid position corresponding to a ubiquitin or ISG15 substrate binding interface of vOTU domain protease, wherein the amino acid position corresponds to position 13 or position 77 of the L-protein of Crimean Congo hemorrhagic fever (CCHF) virus.

10. The recombinantly altered nairovirus of claim 9, which is an Erve virus.

11. The recombinantly altered Erve virus of claim 10, which has been modified at position(s) corresponding to position 13, or positions 13 and 77 of the L protein of Crimean Congo hemorrhagic fever (CCHF) virus.

12. The recombinantly altered nairovirus of claim 11, wherein the position corresponding to position 13 of the L-protein of Crimean Congo hemorrhagic fever (CCHF) virus is changed to arginine.

13. The recombinantly altered nairovirus of claim 11, wherein the position corresponding to position 77 of the L-protein of Crimean Congo hemorrhagic fever (CCHF) virus is changed to aspartic acid.

14. The recombinantly altered nairovirus of claim 9, wherein the vOTU domain protease has no ability or a reduced ability to inhibit expression of interferon $\beta$.

15. A host human cell line transfected with a recombinantly altered nairovirus of claim 9.

16. A method of eliciting a specific immune response to a nairovirus in a subject, comprising administering to a subject in need thereof a composition of claim 1.

17. A method of developing an immunogenic but substantially non-pathogenic nairovirus, comprising:
 (a) transfecting a host cell with the genome of a wild-type nairovirus;
 (b) introducing one or more genetic alterations into the genome such that the genome encodes an L protein that is recombinantly altered to have decreased deubiquinating activity or decreased deISGylating activity while maintaining protease activity, such that the nairovirus replicates in human cells, wherein the recombinantly altered L protein is altered at least at one amino acid position corresponding to a ubiquitin or ISG15 substrate binding interface of vOTU domain protease, wherein the amino acid position corresponds to position 13 or position 77 of the L-protein of Crimean Congo hemorrhagic fever (CCHF) virus;
 (c) obtaining replicated virus particles comprising the genetic alterations from the host cell;
 (d) testing the replicated virus particles for decreased deubiquitinating activity and/or decreased deISGylating activity; and
 (e) selecting one or more virus particles with decreased deubiquitinating activity and/or decreased deISGylating activity.

18. The method of claim 17, wherein step (a) comprises transfecting the host cell with the L, M, and S gene sectors in separate vectors.

19. A method for producing an immunogenic composition for eliciting an immune response against a nairovirus, comprising replicating a recombinant virus developed according to the method of claim 17, and combining the replicated virus with a pharmaceutically compatible excipient.

* * * * *

```
                          SEQUENCE LISTING

<160> NUMBER OF SEQ ID NOS: 26

<210> SEQ ID NO 1
    <211> LENGTH: 3945
    <212> TYPE: PRT
    <213> ORGANISM: Artificial sequence
    <220> FEATURE:
    <223> OTHER INFORMATION: Synthetic construct

<400> SEQUENCE: 1

Met Asp Phe Leu Arg Ser Leu Asp Trp Thr Gln Val Arg Ala Gly Gln
    1               5                   10                  15

Tyr Val Ser Asn Pro Arg Phe Asn Ile Ser Asp Tyr Phe Glu Ile Val
                    20                  25                  30

Arg Gln Pro Gly Asp Gly Asn Cys Phe Tyr His Ser Ile Ala Glu Leu
                35                  40                  45

Thr Met Pro Asn Lys Thr Asp His Ser Tyr His Tyr Ile Lys Arg Leu
        50                  55                  60

Thr Glu Ser Ala Ala Arg Lys Tyr Tyr Gln Glu Glu Asp Glu Ala Arg
    65                  70                  75                  80

Leu Val Gly Leu Ser Leu Glu Asp Tyr Leu Lys Arg Met Leu Ser Asp
                    85                  90                  95

Asn Glu Trp Gly Ser Thr Leu Glu Ala Ser Met Leu Ala Lys Glu Met
                    100                 105                 110

Gly Ile Thr Ile Ile Ile Trp Thr Val Ala Ala Ser Asp Glu Val Glu
                115                 120                 125

Ala Gly Ile Lys Phe Gly Asp Gly Asp Val Phe Thr Ala Val Asn Leu
        130                 135                 140
```

```
Leu His Ser Gly Gln Thr His Phe Asp Ala Leu Arg Ile Leu Pro Gln
145                 150                 155                 160

Phe Glu Thr Asp Thr Arg Glu Ala Leu Ser Leu Met Asp Arg Val Ile
            165                 170                 175

Ala Val Asp Gln Leu Thr Ser Ser Ser Asp Glu Leu Gln Asp Tyr
        180                 185                 190

Glu Asp Leu Ala Leu Ala Leu Thr Ser Ala Glu Glu Ser Asn Arg Arg
        195                 200                 205

Ser Ser Leu Asp Glu Val Thr Leu Ser Lys Lys Gln Ala Glu Ile Leu
    210                 215                 220

Arg Gln Lys Ala Ser Gln Leu Ser Lys Leu Val Asn Lys Ser Gln Asn
225                 230                 235                 240

Ile Pro Thr Arg Val Gly Arg Val Leu Asp Cys Met Phe Asn Cys Lys
            245                 250                 255

Leu Cys Val Glu Ile Ser Ala Asp Thr Leu Ile Leu Arg Pro Glu Ser
            260                 265                 270

Lys Glu Lys Ile Gly Glu Ile Met Ser Leu Arg Gln Leu Gly His Lys
        275                 280                 285

Leu Leu Thr Arg Asp Lys Gln Ile Lys Gln Glu Phe Ser Arg Met Lys
    290                 295                 300

Leu Tyr Val Thr Lys Asp Leu Leu Asp His Leu Asp Val Gly Leu
305                 310                 315                 320

Leu Arg Ala Ala Phe Pro Gly Thr Gly Ile Glu Arg His Met Gln Leu
            325                 330                 335

Leu His Ser Glu Met Ile Leu Asp Ile Cys Thr Val Ser Leu Gly Val
            340                 345                 350

Met Leu Ser Thr Phe Leu Tyr Gly Ser Asn Asn Lys Asn Lys Lys Lys
        355                 360                 365

Phe Ile Thr Asn Cys Leu Leu Ser Thr Ala Leu Ser Gly Lys Lys Val
    370                 375                 380

Tyr Lys Val Leu Gly Asn Leu Gly Asn Glu Leu Leu Tyr Lys Ala Pro
385                 390                 395                 400

Arg Lys Ala Leu Ala Thr Val Cys Ser Ala Leu Phe Gly Lys Gln Ile
            405                 410                 415

Asn Lys Leu Gln Asn Cys Phe Arg Thr Ile Ser Pro Val Ser Leu Leu
            420                 425                 430

Ala Leu Arg Asn Leu Asp Phe Asp Cys Leu Ser Val Gln Asp Tyr Asn
        435                 440                 445

Gly Met Ile Glu Asn Met Ser Lys Leu Asp Asn Thr Asp Val Glu Phe
        450                 455                 460

Asn His Arg Glu Ile Ala Asp Leu Asn Gln Leu Thr Ser Arg Leu Ile
465                 470                 475                 480

Thr Leu Arg Lys Glu Lys Asp Thr Asp Leu Leu Lys Gln Trp Phe Pro
            485                 490                 495

Glu Ser Asp Leu Thr Arg Arg Ser Ile Arg Asn Ala Ala Asn Ala Glu
            500                 505                 510

Glu Phe Val Ile Ser Glu Phe Phe Lys Lys Asp Ile Met Lys Phe
        515                 520                 525

Ile Ser Thr Ser Gly Arg Ala Met Ser Ala Gly Lys Ile Gly Asn Val
    530                 535                 540

Leu Ser Tyr Ala His Asn Leu Tyr Leu Ser Lys Ser Ser Leu Asn Met
545                 550                 555                 560
```

```
Thr Ser Glu Asp Ile Ser Gln Leu Leu Ile Glu Ile Lys Arg Leu Tyr
            565                 570                 575

Ala Leu Gln Glu Asp Ser Glu Val Glu Pro Ile Ala Ile Ile Cys Asp
        580                 585                 590

Gly Ile Glu Ser Asn Met Lys Gln Leu Phe Ala Ile Leu Pro Pro Asp
        595                 600                 605

Cys Ala Arg Glu Cys Glu Val Leu Phe Asp Asp Ile Arg Asn Ser Pro
610                 615                 620

Thr His Ser Thr Ala Trp Lys His Ala Leu Arg Leu Lys Gly Thr Ala
625                 630                 635                 640

Tyr Glu Gly Leu Phe Ala Asn Cys Tyr Gly Trp Gln Tyr Ile Pro Glu
                645                 650                 655

Asp Ile Lys Pro Ser Leu Thr Met Leu Ile Gln Thr Leu Phe Pro Asp
            660                 665                 670

Lys Phe Glu Asp Phe Leu Asp Arg Thr Gln Leu His Pro Glu Phe Arg
        675                 680                 685

Asp Leu Thr Pro Asp Phe Ser Leu Thr Gln Lys Val His Phe Lys Arg
    690                 695                 700

Asn Gln Ile Pro Ser Val Glu Asn Val Gln Ile Ser Ile Asp Ala Thr
705                 710                 715                 720

Leu Pro Glu Ser Val Glu Ala Val Pro Val Thr Glu Arg Lys Met Phe
                725                 730                 735

Pro Leu Pro Glu Thr Pro Leu Ser Glu Val His Ser Ile Glu Arg Ile
            740                 745                 750

Met Glu Asn Phe Thr Arg Leu Met His Gly Gly Arg Leu Ser Thr Lys
        755                 760                 765

Lys Arg Asp Gly Asp Pro Ala Glu Gln Gly Asn Gln Gln Ser Ile Thr
    770                 775                 780

Glu His Glu Ser Ser Ser Ile Ser Ala Phe Lys Asp Tyr Gly Glu Arg
785                 790                 795                 800

Gly Ile Val Glu Glu Asn His Met Lys Phe Ser Gly Glu Asp Gln Leu
                805                 810                 815

Glu Thr Arg Gln Leu Leu Leu Val Glu Val Gly Phe Gln Thr Asp Ile
            820                 825                 830

Asp Gly Lys Ile Arg Thr Asp His Lys Lys Trp Lys Asp Ile Leu Lys
        835                 840                 845

Leu Leu Glu Leu Leu Gly Ile Lys Cys Ser Phe Ile Ala Cys Ala Asp
    850                 855                 860

Cys Ser Ser Thr Pro Pro Asp Arg Trp Trp Ile Thr Glu Asp Arg Val
865                 870                 875                 880

Arg Val Leu Lys Asn Ser Val Ser Phe Leu Phe Asn Lys Leu Ser Arg
                885                 890                 895

Asn Ser Pro Thr Glu Val Thr Asp Ile Val Val Gly Ala Ile Ser Thr
            900                 905                 910

Gln Lys Val Arg Ser Tyr Leu Lys Ala Gly Thr Ala Thr Lys Thr Pro
        915                 920                 925

Val Ser Thr Lys Asp Val Leu Glu Thr Trp Glu Lys Met Lys Glu His
    930                 935                 940

Ile Leu Asn Arg Pro Thr Gly Leu Thr Leu Pro Thr Ser Leu Glu Gln
945                 950                 955                 960

Ala Met Arg Lys Gly Leu Val Glu Gly Val Val Ile Ser Lys Glu Gly
                965                 970                 975

Ser Glu Ser Cys Ile Asn Met Leu Lys Glu Asn Leu Asp Arg Ile Thr
```

-continued

```
                980             985             990
Asp Glu Phe Glu Arg Thr Lys Phe Lys His Glu Leu Thr Gln Asn Ile
            995             1000            1005

Thr Thr Ser Glu Lys Met Leu Leu Ser Trp Leu Ser Glu Asp Ile
    1010            1015            1020

Lys Ser Ser Arg Cys Gly Glu Cys Leu Ser Asn Ile Lys Lys Ala
    1025            1030            1035

Val Asp Glu Thr Ala Asn Leu Ser Glu Lys Ile Glu Leu Leu Ala
    1040            1045            1050

Tyr Asn Leu Gln Leu Thr Asn His Cys Ser Asn Cys His Pro Asn
    1055            1060            1065

Gly Val Asn Ile Ser Asn Thr Ser Asn Val Cys Lys Arg Cys Pro
    1070            1075            1080

Lys Ile Glu Val Val Ser His Cys Glu Asn Lys Gly Phe Glu Asp
    1085            1090            1095

Ser Asn Glu Cys Leu Thr Asp Leu Asp Arg Leu Val Arg Leu Thr
    1100            1105            1110

Leu Pro Gly Lys Thr Glu Lys Glu Arg Arg Val Lys Arg Asn Val
    1115            1120            1125

Glu Tyr Leu Ile Lys Leu Met Met Ser Met Ser Gly Ile Asp Cys
    1130            1135            1140

Ile Lys Tyr Pro Thr Gly Gln Leu Ile Thr His Gly Arg Val Ser
    1145            1150            1155

Ala Lys His Asn Asp Gly Asn Leu Lys Asp Arg Ser Asp Asp Asp
    1160            1165            1170

Gln Arg Leu Ala Glu Lys Ile Asp Thr Val Arg Lys Glu Leu Ser
    1175            1180            1185

Glu Ser Lys Leu Lys Asp Tyr Ser Thr Tyr Ala Arg Gly Val Ile
    1190            1195            1200

Ser Asn Ser Leu Lys Asn Leu Ser Arg Gln Gly Lys Ser Lys Cys
    1205            1210            1215

Ser Val Pro Arg Ser Trp Leu Glu Lys Val Leu Phe Asp Leu Lys
    1220            1225            1230

Val Pro Thr Lys Asp Glu Glu Val Leu Ile Asn Ile Arg Asn Ser
    1235            1240            1245

Leu Lys Ala Arg Ser Glu Phe Val Arg Asn Asn Asp Lys Leu Leu
    1250            1255            1260

Ile Arg Ser Lys Glu Glu Leu Lys Lys Cys Phe Asp Val Gln Ser
    1265            1270            1275

Phe Lys Leu Lys Lys Asn Lys Gln Pro Val Pro Phe Gln Val Asp
    1280            1285            1290

Cys Ile Leu Phe Lys Glu Val Ala Ala Glu Cys Met Lys Arg Tyr
    1295            1300            1305

Ile Gly Thr Pro Tyr Glu Gly Ile Val Asp Thr Leu Val Ser Leu
    1310            1315            1320

Ile Asn Val Leu Thr Arg Phe Thr Trp Phe Gln Glu Val Val Leu
    1325            1330            1335

Tyr Gly Lys Ile Cys Glu Thr Phe Leu Arg Cys Cys Thr Glu Phe
    1340            1345            1350

Asn Arg Ser Gly Val Lys Leu Val Lys Ile Arg His Cys Asn Ile
    1355            1360            1365

Asn Leu Ser Val Lys Leu Pro Ser Asn Lys Lys Glu Asn Met Leu
    1370            1375            1380
```

-continued

```
Cys Cys Leu Tyr Ser Gly Asn Met Glu Leu Leu Gln Gly Pro Phe
1385                1390                1395

Tyr Leu Asn Arg Arg Gln Ala Val Leu Gly Ser Ser Tyr Leu Tyr
1400                1405                1410

Ile Val Ile Thr Leu Tyr Ile Gln Val Leu Gln Gln Tyr Arg Cys
1415                1420                1425

Leu Glu Val Ile Asn Ser Val Ser Glu Lys Thr Leu Gln Asp Ile
1430                1435                1440

Glu Asn His Ser Met Thr Leu Leu Glu Asp Ser Phe Arg Glu Ile
1445                1450                1455

Thr Phe Ala Leu Glu Gly Arg Phe Glu Glu Ser Tyr Lys Ile Arg
1460                1465                1470

Thr Ser Arg Cys Arg Ala Ser Gly Asn Phe Leu Asn Arg Ser Ser
1475                1480                1485

Arg Asp His Phe Ile Ser Val Ser Gly Leu Asn Leu Val Tyr
1490                1495                1500

Gly Phe Leu Ile Lys Asp Asn Leu Leu Ala Asn Ser Gln Gln Gln
1505                1510                1515

Asn Lys Gln Leu Gln Met Leu Arg Phe Gly Met Leu Ala Gly Leu
1520                1525                1530

Ser Arg Leu Val Cys Pro Asn Glu Leu Gly Lys Lys Phe Ser Thr
1535                1540                1545

Ser Cys Arg Arg Ile Glu Asp Asn Ile Ala Arg Leu Tyr Leu Gln
1550                1555                1560

Thr Ser Ile Tyr Cys Ser Val Arg Asp Val Glu Asp Asn Val Lys
1565                1570                1575

His Trp Lys Gln Arg Asp Leu Cys Pro Glu Val Thr Ile Pro Cys
1580                1585                1590

Phe Thr Val Tyr Gly Thr Phe Val Asn Ser Asp Arg Gln Leu Ile
1595                1600                1605

Phe Asp Ile Tyr Asn Val His Ile Tyr Asn Lys Glu Met Asp Asn
1610                1615                1620

Phe Asp Glu Gly Cys Ile Ser Val Leu Glu Glu Thr Ala Glu Arg
1625                1630                1635

His Met Leu Trp Glu Leu Asp Leu Met Asn Ser Leu Cys Ser Asp
1640                1645                1650

Glu Lys Lys Asp Thr Arg Thr Ala Arg Leu Leu Leu Gly Cys Pro
1655                1660                1665

Asn Val Arg Lys Ala Ala Asn Arg Glu Gly Lys Lys Leu Leu Lys
1670                1675                1680

Leu Asn Ser Asp Thr Ser Thr Asp Thr Gln Ser Ile Ala Ser Glu
1685                1690                1695

Val Ser Asp Arg Arg Ser Tyr Ser Ser Ser Lys Ser Arg Ile Arg
1700                1705                1710

Ser Ile Phe Gly Arg Tyr Asn Ser Gln Lys Lys Pro Phe Glu Leu
1715                1720                1725

Arg Ser Gly Leu Glu Val Phe Asn Asp Pro Phe Asn Asp Tyr Gln
1730                1735                1740

Gln Ala Ile Thr Asp Ile Cys Gln Phe Ser Glu Tyr Thr Pro Asn
1745                1750                1755

Lys Glu Ser Ile Leu Lys Asp Cys Leu Gln Ile Ile Arg Lys Asn
1760                1765                1770
```

```
Pro Ser His Thr Met Gly Ser  Phe Glu Leu Ile Gln  Ala Ile Ser
    1775              1780                 1785

Glu Phe Gly Met Ser Lys Phe  Pro Pro Glu Asn Ile  Asp Lys Ala
    1790              1795                 1800

Arg Arg Asp Pro Lys Asn Trp  Val Ser Ile Ser Glu  Val Thr Glu
    1805              1810                 1815

Thr Thr Ser Ile Val Ala Ser  Pro Arg Thr His Met  Met Leu Lys
    1820              1825                 1830

Asp Cys Phe Lys Ile Ile Leu  Gly Thr Glu Asn Lys  Lys Ile Val
    1835              1840                 1845

Lys Met Leu Arg Gly Lys Leu  Lys Lys Leu Gly Ala  Ile Ser Thr
    1850              1855                 1860

Asn Ile Glu Ile Gly Lys Arg  Asp Cys Leu Asp Leu  Leu Ser Thr
    1865              1870                 1875

Val Asp Gly Leu Thr Asp Gln  Gln Lys Glu Asn Ile  Val Asn Gly
    1880              1885                 1890

Ile Phe Glu Pro Ser Lys Leu  Ser Phe Tyr His Trp  Lys Glu Leu
    1895              1900                 1905

Val Lys Lys Asn Ile Asp Glu  Val Leu Leu Thr Glu  Asp Gly Asn
    1910              1915                 1920

Leu Ile Phe Cys Trp Leu Lys  Thr Ile Ser Ser Val  Val Lys Gly
    1925              1930                 1935

Ser Leu Lys Lys Arg Leu Lys  Phe Met Asn Ile His  Ser Pro Glu
    1940              1945                 1950

Leu Met Pro Glu Asn Cys Leu  Phe Ser Ser Glu Glu  Phe Asn Glu
    1955              1960                 1965

Leu Ile Lys Leu Lys Lys Leu  Leu Leu Asn Glu Gln  Gln Asp Glu
    1970              1975                 1980

Gln Glu Leu Lys Gln Asp Leu  Leu Ile Ser Ser Trp  Ile Lys Cys
    1985              1990                 1995

Ile Thr Ala Cys Lys Asp Phe  Ala Ser Ile Asn Asp  Lys Ile Gln
    2000              2005                 2010

Lys Phe Ile Tyr His Leu Ser  Glu Glu Leu Tyr Asp  Ile Arg Leu
    2015              2020                 2025

Gln His Leu Glu Leu Ser Lys  Leu Lys Gln Glu His  Pro Ser Val
    2030              2035                 2040

Ser Phe Thr Lys Glu Glu Val  Leu Ile Lys Arg Leu  Glu Lys Asn
    2045              2050                 2055

Phe Leu Lys Gln His Asn Leu  Glu Ile Met Glu Thr  Val Asn Leu
    2060              2065                 2070

Val Phe Phe Ala Ala Leu Ser  Ala Pro Trp Cys Leu  His Tyr Lys
    2075              2080                 2085

Ala Leu Glu Ser Tyr Leu Val  Arg His Pro Glu Ile  Leu Asp Cys
    2090              2095                 2100

Gly Ser Lys Glu Asp Cys Lys  Leu Thr Leu Leu Asp  Leu Ser Val
    2105              2110                 2115

Ser Lys Leu Leu Val Cys Leu  Tyr Gln Lys Asp Asp  Glu Glu Leu
    2120              2125                 2130

Ile Asn Ser Ser Ser Leu Lys  Leu Gly Phe Leu Val  Lys Tyr Val
    2135              2140                 2145

Val Thr Leu Phe Thr Ser Asn  Gly Glu Pro Phe Ser  Leu Ser Leu
    2150              2155                 2160

Asn Asp Gly Gly Leu Asp Leu  Asp Leu His Lys Thr  Thr Asp Glu
```

-continued

```
            2165                2170                2175
Lys Leu Leu His Gln Thr Lys Ile Val Phe Ala Lys Ile Gly Leu
        2180                2185                2190
Ser Gly Asn Ser Tyr Asp Phe Ile Trp Thr Thr Gln Met Ile Ala
        2195                2200                2205
Asn Ser Asn Phe Asn Val Cys Lys Arg Leu Thr Gly Arg Ser Thr
        2210                2215                2220
Gly Glu Arg Leu Pro Arg Ser Val Arg Ser Lys Val Ile Tyr Glu
        2225                2230                2235
Met Val Lys Leu Val Gly Glu Thr Gly Met Ala Ile Leu Gln Gln
        2240                2245                2250
Leu Ala Phe Ala Gln Ala Leu Asn Tyr Glu His Arg Phe Tyr Ala
        2255                2260                2265
Val Leu Ala Pro Lys Ala Gln Leu Gly Gly Ala Arg Asp Leu Leu
        2270                2275                2280
Val Gln Glu Thr Gly Thr Lys Val Met His Ala Thr Thr Glu Met
        2285                2290                2295
Phe Ser Arg Asn Leu Leu Lys Thr Thr Ser Asp Asp Gly Leu Thr
        2300                2305                2310
Asn Pro His Leu Lys Glu Thr Ile Leu Asn Val Gly Leu Asp Cys
        2315                2320                2325
Leu Ala Asn Met Arg Asn Leu Asp Gly Lys Pro Ile Ser Glu Gly
        2330                2335                2340
Ser Asn Leu Val Asn Phe Tyr Lys Val Ile Cys Ile Ser Gly Asp
        2345                2350                2355
Asn Thr Lys Trp Gly Pro Ile His Cys Cys Ser Phe Phe Ser Gly
        2360                2365                2370
Met Met Gln Gln Val Leu Lys Asn Val Pro Asp Trp Cys Ser Phe
        2375                2380                2385
Tyr Lys Leu Thr Phe Ile Lys Asn Leu Cys Arg Gln Val Glu Ile
        2390                2395                2400
Pro Ala Gly Ser Ile Lys Lys Ile Leu Asn Val Leu Arg Tyr Arg
        2405                2410                2415
Leu Cys Ser Lys Gly Gly Val Glu Gln His Ser Glu Glu Asp Leu
        2420                2425                2430
Arg Arg Leu Leu Thr Asp Asn Leu Asp Ser Trp Asp Gly Asn Asp
        2435                2440                2445
Thr Val Lys Phe Leu Val Thr Thr Tyr Ile Ser Lys Gly Leu Met
        2450                2455                2460
Ala Leu Asn Ser Tyr Asn His Met Gly Gln Gly Ile His His Ala
        2465                2470                2475
Thr Ser Ser Val Leu Thr Ser Leu Ala Ala Val Leu Phe Glu Glu
        2480                2485                2490
Leu Ala Ile Phe Tyr Leu Lys Arg Ser Leu Pro Gln Thr Thr Val
        2495                2500                2505
His Val Glu His Ala Gly Ser Ser Asp Asp Tyr Ala Lys Cys Ile
        2510                2515                2520
Val Val Thr Gly Ile Leu Ser Lys Glu Leu Tyr Ser Gln Tyr Asp
        2525                2530                2535
Glu Thr Phe Trp Lys His Ala Cys Arg Leu Lys Asn Phe Thr Ala
        2540                2545                2550
Ala Val Gln Arg Cys Cys Gln Met Lys Asp Ser Ala Lys Thr Leu
        2555                2560                2565
```

```
Val Ser Asp Cys Phe Leu Glu Phe Tyr Ser Glu Phe Met Met Gly
    2570                2575            2580

Tyr Arg Val Thr Pro Ala Val Ile Lys Phe Met Phe Thr Gly Leu
    2585                2590            2595

Ile Asn Ser Ser Val Thr Ser Pro Gln Ser Leu Met Gln Ala Cys
    2600                2605            2610

Gln Val Ser Ser Gln Gln Ala Met Tyr Asn Ser Val Pro Leu Val
    2615                2620            2625

Thr Asn Thr Ala Phe Thr Leu Leu Arg Gln Gln Ile Phe Phe Asn
    2630                2635            2640

His Val Glu Asp Phe Ile Arg Arg Tyr Gly Ile Leu Thr Leu Gly
    2645                2650            2655

Thr Leu Ser Pro Phe Gly Arg Leu Phe Val Pro Thr Tyr Ser Gly
    2660                2665            2670

Leu Ala Ser Ser Thr Val Ala Leu Glu Asp Ala Glu Val Ile Ala
    2675                2680            2685

Arg Ala Ala Gln Thr Leu Gln Met Asn Ser Val Ser Ile Gln Ser
    2690                2695            2700

Ser Ser Leu Thr Thr Leu Asp Ser Leu Gly Arg Ser Arg Thr Ser
    2705                2710            2715

Ser Thr Ala Glu Asp Ser Ser Val Ser Asp Thr Thr Ala Ala
    2720                2725            2730

Ser His Asp Ser Gly Ser Ser Ser Ser Phe Ser Phe Glu Leu
    2735                2740            2745

Asn Arg Pro Leu Ser Glu Thr Glu Leu Gln Phe Ile Lys Ala Leu
    2750                2755            2760

Ser Ser Leu Lys Ser Thr Gln Ala Cys Glu Val Ile Gln Asn Arg
    2765                2770            2775

Ile Thr Gly Leu Tyr Cys Asn Ser Asn Glu Gly Pro Leu Asp Arg
    2780                2785            2790

His Asn Val Ile Tyr Ser Ser Arg Met Ala Asp Ser Cys Asp Trp
    2795                2800            2805

Leu Lys Asp Gly Lys Arg Arg Gly Asn Leu Glu Leu Ala Asn Arg
    2810                2815            2820

Ile Gln Ser Val Leu Cys Ile Leu Ile Ala Gly Tyr Tyr Arg Ser
    2825                2830            2835

Phe Gly Gly Glu Gly Thr Glu Lys Gln Val Lys Ala Ser Leu Asn
    2840                2845            2850

Arg Asp Asp Asn Lys Ile Ile Glu Asp Pro Met Ile Gln Leu Ile
    2855                2860            2865

Pro Glu Lys Leu Arg Arg Glu Leu Glu Arg Leu Gly Val Ser Arg
    2870                2875            2880

Met Glu Val Asp Glu Leu Met Pro Ser Ile Ser Pro Asp Asp Thr
    2885                2890            2895

Leu Ala Gln Leu Val Ala Lys Lys Leu Ile Ser Leu Asn Val Ser
    2900                2905            2910

Thr Glu Glu Tyr Ser Ala Glu Val Ser Arg Leu Lys Gln Thr Leu
    2915                2920            2925

Thr Ala Arg Asn Val Leu His Gly Leu Ala Gly Gly Ile Lys Glu
    2930                2935            2940

Leu Ser Leu Pro Ile Tyr Thr Ile Phe Met Lys Ser Tyr Phe Phe
    2945                2950            2955
```

-continued

```
Lys Asp Asn Val Phe Leu Ser Leu Thr Asp Arg Trp Ser Thr Lys
    2960                2965                2970
His Ser Thr Asn Tyr Arg Asp Ser Cys Gly Lys Gln Leu Lys Gly
    2975                2980                2985
Arg Ile Ile Thr Lys Tyr Thr His Trp Leu Asp Thr Phe Leu Gly
    2990                2995                3000
Cys Ser Val Ser Ile Asn Arg His Thr Thr Val Lys Glu Pro Ser
    3005                3010                3015
Leu Phe Asn Pro Asn Ile Arg Cys Val Asn Leu Ile Thr Phe Glu
    3020                3025                3030
Asp Gly Leu Arg Glu Leu Ser Val Ile Gln Ser His Leu Lys Val
    3035                3040                3045
Phe Glu Asn Glu Phe Thr Asn Leu Asn Leu Gln Phe Ser Asp Pro
    3050                3055                3060
Asn Arg Gln Lys Leu Arg Ile Val Glu Ser Arg Pro Ala Glu Ser
    3065                3070                3075
Glu Leu Glu Ala Asn Arg Ala Val Ile Val Lys Thr Lys Leu Phe
    3080                3085                3090
Ser Ala Thr Glu Gln Val Arg Leu Ser Asn Asn Pro Ala Val Val
    3095                3100                3105
Met Gly Tyr Leu Leu Asp Glu Ser Ala Ile Ser Glu Val Lys Pro
    3110                3115                3120
Thr Lys Val Asp Phe Ser Asn Leu Leu Lys Asp Arg Phe Lys Ile
    3125                3130                3135
Met Gln Phe Phe Pro Ser Val Phe Thr Leu Ile Lys Met Leu Thr
    3140                3145                3150
Asp Glu Ser Ser Asp Ser Glu Lys Ser Gly Leu Ser Pro Asp Leu
    3155                3160                3165
Gln Gln Val Ala Arg Tyr Ser Asn His Leu Thr Leu Leu Ser Arg
    3170                3175                3180
Met Ile Gln Gln Ala Lys Pro Thr Val Thr Val Phe Tyr Met Leu
    3185                3190                3195
Lys Gly Asn Leu Met Asn Thr Glu Pro Thr Val Ala Glu Leu Val
    3200                3205                3210
Ser Tyr Gly Ile Lys Glu Gly Arg Phe Phe Arg Leu Ser Asp Thr
    3215                3220                3225
Gly Val Asp Ala Ser Thr Tyr Ser Val Lys Tyr Trp Lys Ile Leu
    3230                3235                3240
His Cys Ile Ser Ala Ile Gly Cys Leu Pro Leu Ser Gln Ala Asp
    3245                3250                3255
Lys Ser Ser Leu Leu Met Ser Phe Leu Asn Trp Arg Val Asn Met
    3260                3265                3270
Asp Ile Arg Thr Ser Asp Cys Pro Leu Ser Ser His Glu Ala Ser
    3275                3280                3285
Ile Leu Ser Glu Phe Asp Gly Gln Val Ile Ala Asn Ile Leu Ala
    3290                3295                3300
Ser Glu Leu Ser Ser Val Lys Arg Asp Ser Glu Arg Glu Gly Leu
    3305                3310                3315
Thr Asp Leu Leu Asp Tyr Leu Asn Ser Pro Thr Glu Leu Leu Lys
    3320                3325                3330
Lys Lys Pro Tyr Leu Gly Thr Thr Cys Lys Phe Asn Thr Trp Gly
    3335                3340                3345
Asp Ser Asn Arg Ser Gly Lys Phe Thr Tyr Ser Ser Arg Ser Gly
```

```
            3350                3355                3360
Glu Ser Ile Gly Ile Phe Ile Ala Gly Lys Leu His Ile His Leu
            3365                3370                3375
Ser Ser Glu Ser Val Ala Leu Leu Cys Glu Thr Glu Arg Gln Val
            3380                3385                3390
Leu Ser Trp Met Ser Lys Arg Arg Thr Glu Val Ile Thr Lys Glu
            3395                3400                3405
Gln His Gln Leu Phe Leu Ser Leu Leu Pro Gln Ser His Glu Cys
            3410                3415                3420
Leu Gln Lys His Lys Asp Gly Ser Ala Leu Ser Val Ile Pro Asp
            3425                3430                3435
Ser Ser Asn Pro Arg Leu Leu Lys Phe Val Pro Leu Lys Lys Gly
            3440                3445                3450
Leu Ala Val Val Lys Ile Lys Lys Gln Ile Leu Thr Val Lys Lys
            3455                3460                3465
Gln Val Val Phe Asp Ala Glu Ser Glu Pro Arg Leu Gln Trp Gly
            3470                3475                3480
His Gly Cys Leu Ser Ile Val Tyr Asp Glu Thr Asp Thr Gln Thr
            3485                3490                3495
Thr Tyr His Glu Asn Leu Leu Lys Val Lys His Leu Val Asp Cys
            3500                3505                3510
Ser Thr Asp Arg Lys Lys Leu Leu Pro Gln Ser Val Phe Ser Asp
            3515                3520                3525
Ser Lys Val Val Leu Ser Arg Ile Lys Phe Lys Thr Glu Leu Leu
            3530                3535                3540
Leu Asn Ser Leu Thr Leu Leu His Cys Phe Leu Lys His Ala Pro
            3545                3550                3555
Ser Asp Ala Ile Met Glu Val Glu Ser Lys Ser Ser Leu Leu His
            3560                3565                3570
Lys Tyr Leu Lys Ser Gly Gly Val Arg Gln Arg Asn Thr Glu Val
            3575                3580                3585
Leu Phe Arg Glu Lys Leu Asn Lys Val Val Ile Lys Asp Asn Leu
            3590                3595                3600
Glu Gln Gly Val Glu Glu Glu Ile Glu Phe Cys Asn Asn Leu Thr
            3605                3610                3615
Lys Thr Val Ser Glu Asn Pro Leu Pro Leu Ser Cys Trp Ser Glu
            3620                3625                3630
Val Gln Asn Tyr Ile Glu Asp Ile Gly Phe Asn Asn Val Leu Val
            3635                3640                3645
Asn Ile Asp Arg Asn Thr Val Lys Ser Glu Leu Leu Trp Lys Phe
            3650                3655                3660
Thr Leu Asp Thr Asn Val Ser Thr Thr Ser Thr Ile Lys Asp Val
            3665                3670                3675
Arg Thr Leu Val Ser Tyr Val Ser Thr Glu Thr Ile Pro Lys Phe
            3680                3685                3690
Leu Leu Ala Phe Leu Leu Tyr Glu Glu Val Leu Met Asn Leu Ile
            3695                3700                3705
Asn Gln Cys Lys Ala Val Lys Glu Leu Ile Asn Ser Thr Gly Leu
            3710                3715                3720
Ser Asp Leu Glu Leu Glu Ser Leu Leu Thr Leu Cys Ala Phe Tyr
            3725                3730                3735
Phe Gln Ser Glu Cys Ser Lys Arg Asp Gly Pro Arg Cys Ser Phe
            3740                3745                3750
```

```
Ala Ala Leu Leu Ser Leu Ile His Glu Asp Trp Gln Arg Ile Gly
    3755                3760                3765

Lys Asn Ile Leu Val Arg Ala Asn Asn Glu Leu Gly Asp Val Ser
3770                3775                3780

Leu Lys Val Asn Ile Val Leu Val Pro Leu Lys Asp Met Ser Lys
    3785                3790                3795

Pro Lys Ser Glu Arg Val Val Met Ala Arg Arg Ser Leu Asn His
3800                3805                3810

Ala Leu Ser Leu Met Phe Leu Asp Glu Met Ser Leu Pro Glu Leu
    3815                3820                3825

Lys Ser Leu Ser Val Asn Cys Lys Met Gly Asn Phe Glu Gly Gln
3830                3835                3840

Glu Cys Phe Glu Phe Thr Ile Leu Lys Asp Asn Ser Ala Arg Leu
    3845                3850                3855

Asp Tyr Asn Lys Leu Ile Asp His Cys Val Asp Met Glu Lys Lys
3860                3865                3870

Arg Glu Ala Val Arg Ala Val Glu Asp Leu Ile Leu Met Leu Thr
    3875                3880                3885

Gly Arg Ala Val Lys Pro Ser Ala Val Thr Gln Phe Val His Gly
3890                3895                3900

Asp Glu Gln Cys Gln Glu Gln Ile Ser Leu Asp Leu Met Ala
    3905                3910                3915

Asn Asp Thr Val Thr Asp Phe Pro Asp Arg Glu Ala Glu Ala Leu
3920                3925                3930

Lys Thr Gly Asn Leu Gly Phe Asn Trp Asp Ser Asp
    3935                3940                3945

<210> SEQ ID NO 2
<211> LENGTH: 1684
<212> TYPE: PRT
<213> ORGANISM: Artificial sequence
<220> FEATURE:
<223> OTHER INFORMATION: Synthetic construct

<400> SEQUENCE: 2

Met His Ile Ser Leu Met Tyr Ala Ile Leu Cys Leu Gln Leu Cys Gly
1               5                   10                  15

Leu Gly Glu Thr His Gly Ser His Asn Glu Thr Arg His Asn Lys Thr
            20                  25                  30

Asp Thr Met Thr Thr Pro Gly Asp Asn Pro Ser Ser Glu Pro Pro Val
        35                  40                  45

Ser Thr Ala Leu Ser Ile Thr Leu Asp Pro Ser Val Thr Pro Thr
    50                  55                  60

Thr Pro Ala Ser Gly Leu Glu Gly Ser Gly Val Tyr Thr Ser Pro
65                  70                  75                  80

Pro Ile Thr Thr Gly Ser Leu Pro Leu Ser Glu Thr Thr Pro Glu Leu
                85                  90                  95

Pro Val Thr Thr Gly Thr Asp Thr Leu Ser Ala Gly Asp Val Asp Pro
            100                 105                 110

Ser Thr Gln Thr Ala Gly Gly Thr Ser Ala Pro Thr Val Arg Thr Ser
        115                 120                 125

Leu Pro Asn Ser Pro Ser Thr Pro Ser Thr Gln Asp Thr His His
    130                 135                 140

Pro Val Arg Asn Leu Leu Ser Val Thr Ser Pro Gly Pro Asp Glu Thr
145                 150                 155                 160
```

```
Ser Thr Pro Ser Gly Thr Gly Lys Glu Ser Ala Thr Ser Ser Pro
            165                 170                 175

His Pro Val Ser Asn Arg Pro Pro Thr Pro Ala Thr Ala Gln Gly
            180                 185                 190

Pro Thr Glu Asn Asp Ser His Asn Ala Thr Glu His Pro Glu Ser Leu
            195                 200                 205

Thr Gln Ser Ala Thr Pro Gly Leu Met Thr Ser Pro Thr Gln Ile Val
            210                 215                 220

His Pro Gln Ser Ala Thr Pro Ile Thr Val Gln Asp Thr His Pro Ser
225                 230                 235                 240

Pro Thr Asn Arg Ser Lys Arg Asn Leu Lys Met Glu Ile Ile Leu Thr
            245                 250                 255

Leu Ser Gln Gly Leu Lys Lys Tyr Tyr Gly Lys Ile Leu Arg Leu Leu
            260                 265                 270

Gln Leu Thr Leu Glu Glu Asp Thr Glu Gly Leu Leu Glu Trp Cys Lys
            275                 280                 285

Arg Asn Leu Gly Leu Asp Cys Asp Asp Thr Phe Phe Gln Lys Arg Ile
            290                 295                 300

Glu Glu Phe Phe Ile Thr Gly Glu Gly His Phe Asn Glu Val Leu Gln
305                 310                 315                 320

Phe Arg Thr Pro Gly Thr Leu Ser Thr Thr Glu Ser Thr Pro Ala Gly
            325                 330                 335

Leu Pro Thr Ala Glu Pro Phe Lys Ser Tyr Phe Ala Lys Gly Phe Leu
            340                 345                 350

Ser Ile Asp Ser Gly Tyr Tyr Ser Ala Lys Cys Tyr Ser Gly Thr Ser
            355                 360                 365

Asn Ser Gly Leu Gln Leu Ile Asn Ile Thr Arg His Ser Thr Arg Ile
            370                 375                 380

Val Asp Thr Pro Gly Pro Lys Ile Thr Asn Leu Lys Thr Ile Asn Cys
385                 390                 395                 400

Ile Asn Leu Lys Ala Ser Ile Phe Lys Glu His Arg Glu Val Glu Ile
            405                 410                 415

Asn Val Leu Leu Pro Gln Val Ala Val Asn Leu Ser Asn Cys His Val
            420                 425                 430

Val Ile Lys Ser His Val Cys Asp Tyr Ser Leu Asp Ile Asp Gly Ala
            435                 440                 445

Val Arg Leu Pro His Ile Tyr His Glu Gly Val Phe Ile Pro Gly Thr
            450                 455                 460

Tyr Lys Ile Val Ile Asp Lys Lys Asn Lys Leu Asn Asp Arg Cys Thr
465                 470                 475                 480

Leu Phe Thr Asp Cys Val Ile Lys Gly Arg Glu Val Arg Lys Gly Gln
            485                 490                 495

Ser Val Leu Arg Gln Tyr Lys Thr Glu Ile Arg Ile Gly Lys Ala Ser
            500                 505                 510

Thr Gly Ser Arg Arg Leu Leu Ser Glu Glu Pro Ser Asp Asp Cys Ile
            515                 520                 525

Ser Arg Thr Gln Leu Leu Arg Thr Glu Thr Ala Glu Ile His Gly Asp
            530                 535                 540

Asn Tyr Gly Gly Pro Gly Asp Lys Ile Thr Ile Cys Asn Gly Ser Thr
545                 550                 555                 560

Ile Val Asp Gln Arg Leu Gly Ser Glu Leu Gly Cys Tyr Thr Ile Asn
            565                 570                 575
```

-continued

```
Arg Val Arg Ser Phe Lys Leu Cys Glu Asn Ser Ala Thr Gly Lys Asn
            580                 585                 590

Cys Glu Ile Asp Ser Val Pro Val Lys Cys Arg Gln Gly Tyr Cys Leu
        595                 600                 605

Arg Ile Thr Gln Glu Gly Arg Gly His Val Lys Leu Ser Arg Gly Ser
    610                 615                 620

Glu Val Val Leu Asp Ala Cys Asp Thr Ser Cys Glu Ile Met Ile Pro
625                 630                 635                 640

Lys Gly Thr Gly Asp Ile Leu Val Asp Cys Ser Gly Gly Gln Gln His
                645                 650                 655

Phe Leu Lys Asp Asn Leu Ile Asp Leu Gly Cys Pro Lys Ile Pro Leu
            660                 665                 670

Leu Gly Lys Met Ala Ile Tyr Ile Cys Arg Met Ser Asn His Pro Lys
        675                 680                 685

Thr Thr Met Ala Phe Leu Phe Trp Phe Ser Phe Gly Tyr Val Ile Thr
    690                 695                 700

Cys Ile Leu Cys Lys Ala Ile Phe Tyr Leu Leu Ile Ile Val Gly Thr
705                 710                 715                 720

Leu Gly Lys Arg Leu Lys Gln Tyr Arg Glu Leu Lys Pro Gln Thr Cys
                725                 730                 735

Thr Ile Cys Glu Thr Thr Pro Val Asn Ala Ile Asp Ala Glu Met His
            740                 745                 750

Asp Leu Asn Cys Ser Tyr Asn Ile Cys Pro Tyr Cys Ala Ser Arg Leu
        755                 760                 765

Thr Ser Asp Gly Leu Ala Arg His Val Ile Gln Cys Pro Lys Arg Lys
    770                 775                 780

Glu Lys Val Glu Glu Thr Glu Leu Tyr Leu Asn Leu Glu Arg Ile Pro
785                 790                 795                 800

Trp Val Val Arg Lys Leu Leu Gln Val Ser Glu Ser Thr Gly Val Ala
                805                 810                 815

Leu Lys Arg Ser Ser Trp Leu Ile Val Leu Val Leu Phe Thr Val
            820                 825                 830

Ser Leu Ser Pro Val Gln Ser Ala Pro Ile Gly Gln Gly Lys Thr Ile
        835                 840                 845

Glu Ala Tyr Arg Ala Arg Glu Gly Tyr Thr Ser Ile Cys Leu Phe Val
    850                 855                 860

Leu Gly Ser Ile Leu Phe Ile Val Ser Cys Leu Met Lys Gly Leu Val
865                 870                 875                 880

Asp Ser Val Gly Asn Ser Phe Phe Pro Gly Leu Ser Ile Cys Lys Thr
                885                 890                 895

Cys Ser Ile Ser Ser Ile Asn Gly Phe Glu Ile Glu Ser His Lys Cys
            900                 905                 910

Tyr Cys Ser Leu Phe Cys Cys Pro Tyr Cys Arg His Cys Ser Thr Asp
        915                 920                 925

Lys Glu Ile His Lys Leu His Leu Ser Ile Cys Lys Lys Arg Lys Lys
    930                 935                 940

Gly Ser Asn Val Met Leu Ala Val Cys Lys Leu Met Cys Phe Arg Ala
945                 950                 955                 960

Thr Met Glu Val Ser Asn Arg Ala Leu Phe Ile Arg Ser Ile Ile Asn
                965                 970                 975

Thr Thr Phe Val Leu Cys Ile Leu Ile Leu Ala Val Cys Val Val Ser
            980                 985                 990

Thr Ser Ala Val Glu Met Glu Asn  Leu Pro Ala Gly Thr  Trp Glu Arg
```

```
              995                 1000              1005
    Glu  Glu  Asp  Leu  Thr  Asn  Phe  Cys  His  Gln  Glu  Cys  Gln  Val  Thr
         1010                1015               1020

Glu  Thr  Glu  Cys  Leu  Cys  Pro  Tyr  Glu  Ala  Leu  Val  Leu  Arg  Lys
         1025                1030               1035

Pro  Leu  Phe  Leu  Asp  Ser  Thr  Ala  Lys  Gly  Met  Lys  Asn  Leu  Leu
         1040                1045               1050

Asn  Ser  Thr  Ser  Leu  Glu  Thr  Ser  Leu  Ser  Ile  Glu  Ala  Pro  Trp
         1055                1060               1065

Gly  Ala  Ile  Asn  Val  Gln  Ser  Thr  Tyr  Lys  Pro  Thr  Val  Ser  Thr
         1070                1075               1080

Ala  Asn  Ile  Ala  Leu  Ser  Trp  Ser  Ser  Val  Glu  His  Arg  Gly  Asn
         1085                1090               1095

Lys  Ile  Leu  Val  Ser  Gly  Arg  Ser  Glu  Ser  Ile  Met  Lys  Leu  Glu
         1100                1105               1110

Glu  Arg  Thr  Gly  Ile  Ser  Trp  Asp  Leu  Gly  Val  Glu  Asp  Ala  Ser
         1115                1120               1125

Glu  Ser  Lys  Leu  Leu  Thr  Val  Ser  Val  Met  Asp  Leu  Ser  Gln  Met
         1130                1135               1140

Tyr  Ser  Pro  Val  Phe  Glu  Tyr  Leu  Ser  Gly  Asp  Arg  Gln  Val  Gly
         1145                1150               1155

Glu  Trp  Pro  Lys  Ala  Thr  Cys  Thr  Gly  Asp  Cys  Pro  Glu  Arg  Cys
         1160                1165               1170

Gly  Cys  Thr  Ser  Ser  Thr  Cys  Leu  His  Lys  Glu  Trp  Pro  His  Ser
         1175                1180               1185

Arg  Asn  Trp  Arg  Cys  Asn  Pro  Thr  Trp  Cys  Trp  Gly  Val  Gly  Thr
         1190                1195               1200

Gly  Cys  Thr  Cys  Cys  Gly  Leu  Asp  Val  Lys  Asp  Leu  Phe  Thr  Asp
         1205                1210               1215

Tyr  Met  Phe  Val  Lys  Trp  Lys  Val  Glu  Tyr  Ile  Lys  Thr  Glu  Ala
         1220                1225               1230

Ile  Val  Cys  Val  Glu  Leu  Thr  Ser  Gln  Glu  Arg  Gln  Cys  Ser  Leu
         1235                1240               1245

Ile  Glu  Ala  Gly  Thr  Arg  Phe  Asn  Leu  Gly  Pro  Val  Thr  Ile  Thr
         1250                1255               1260

Leu  Ser  Glu  Pro  Arg  Asn  Ile  Gln  Gln  Lys  Leu  Pro  Pro  Glu  Ile
         1265                1270               1275

Ile  Thr  Leu  His  Pro  Arg  Ile  Glu  Glu  Gly  Phe  Phe  Asp  Leu  Met
         1280                1285               1290

His  Val  Gln  Lys  Val  Leu  Ser  Ala  Ser  Thr  Val  Cys  Lys  Leu  Gln
         1295                1300               1305

Ser  Cys  Thr  His  Gly  Val  Pro  Gly  Asp  Leu  Gln  Val  Tyr  His  Ile
         1310                1315               1320

Gly  Asn  Leu  Leu  Lys  Gly  Asp  Lys  Val  Asn  Gly  His  Leu  Ile  His
         1325                1330               1335

Lys  Ile  Glu  Pro  His  Phe  Asn  Thr  Ser  Trp  Met  Ser  Trp  Asp  Gly
         1340                1345               1350

Cys  Asp  Leu  Asp  Tyr  Tyr  Cys  Asn  Met  Gly  Asp  Trp  Pro  Ser  Cys
         1355                1360               1365

Thr  Tyr  Thr  Gly  Val  Thr  Gln  His  Asn  His  Ala  Ser  Phe  Val  Asn
         1370                1375               1380

Leu  Leu  Asn  Ile  Glu  Thr  Asp  Tyr  Thr  Lys  Asn  Phe  His  Phe  His
         1385                1390               1395
```

```
Ser Lys Arg Val Thr Ala His Gly Asp Thr Pro Gln Leu Asp Leu
    1400                1405                1410

Lys Ala Arg Pro Thr Tyr Gly Ala Gly Glu Ile Thr Val Leu Val
    1415                1420                1425

Glu Val Ala Asp Met Glu Leu His Thr Lys Lys Ile Glu Ile Ser
    1430                1435                1440

Gly Leu Lys Phe Ala Ser Leu Ala Cys Thr Gly Cys Tyr Ala Cys
    1445                1450                1455

Ser Ser Gly Ile Ser Cys Lys Val Arg Ile His Val Asp Glu Pro
    1460                1465                1470

Asp Glu Leu Thr Val His Val Lys Ser Asp Pro Asp Val Val
    1475                1480                1485

Ala Ala Ser Ser Ser Leu Met Ala Arg Lys Leu Glu Phe Gly Thr
    1490                1495                1500

Asp Ser Thr Phe Lys Ala Phe Ser Ala Met Pro Lys Thr Ser Leu
    1505                1510                1515

Cys Phe Tyr Ile Val Glu Arg Glu His Cys Lys Ser Cys Ser Glu
    1520                1525                1530

Glu Asp Thr Lys Lys Cys Val Asn Thr Lys Leu Glu Gln Pro Gln
    1535                1540                1545

Ser Ile Leu Ile Glu His Lys Gly Thr Ile Ile Gly Lys Gln Asn
    1550                1555                1560

Ser Thr Cys Thr Ala Lys Ala Ser Cys Trp Leu Glu Ser Val Lys
    1565                1570                1575

Ser Phe Phe Tyr Gly Leu Lys Asn Met Leu Ser Gly Ile Phe Gly
    1580                1585                1590

Asn Val Phe Met Gly Ile Phe Leu Phe Leu Ala Pro Phe Ile Leu
    1595                1600                1605

Leu Ile Leu Phe Phe Met Phe Gly Trp Arg Ile Leu Phe Cys Phe
    1610                1615                1620

Lys Cys Cys Arg Arg Thr Arg Gly Leu Phe Lys Tyr Arg His Leu
    1625                1630                1635

Lys Asp Asp Glu Glu Thr Gly Tyr Arg Arg Ile Ile Glu Lys Leu
    1640                1645                1650

Asn Asn Lys Lys Gly Lys Asn Lys Leu Leu Asp Gly Glu Arg Leu
    1655                1660                1665

Ala Asp Arg Arg Ile Ala Glu Leu Phe Ser Thr Lys Thr His Ile
    1670                1675                1680

Gly

<210> SEQ ID NO 3
<211> LENGTH: 482
<212> TYPE: PRT
<213> ORGANISM: Artificial sequence
<220> FEATURE:
<223> OTHER INFORMATION: Synthetic construct

<400> SEQUENCE: 3

Met Glu Asn Lys Ile Glu Val Asn Asn Lys Asp Glu Met Asn Arg Trp
1               5                   10                  15

Phe Glu Glu Phe Lys Lys Gly Asn Gly Leu Val Asp Thr Phe Thr Asn
                20                  25                  30

Ser Tyr Ser Phe Cys Glu Ser Val Pro Asn Leu Asp Arg Phe Val Phe
            35                  40                  45
```

```
Gln Met Ala Ser Ala Thr Asp Asp Ala Gln Lys Asp Ser Ile Tyr Ala
    50                  55                  60
Ser Ala Leu Val Glu Ala Thr Lys Phe Cys Ala Pro Ile Tyr Glu Cys
65                  70                  75                  80
Ala Trp Val Ser Thr Gly Ile Val Lys Lys Gly Leu Glu Trp Phe
                85                  90                  95
Glu Lys Asn Ala Gly Thr Ile Lys Ser Trp Asp Glu Ser Tyr Thr Glu
            100                 105                 110
Leu Lys Val Asp Val Pro Lys Ile Glu Gln Leu Thr Gly Tyr Gln Gln
                115                 120                 125
Ala Ala Leu Lys Trp Arg Lys Asp Ile Gly Phe Arg Val Asn Ala Asn
130                 135                 140
Thr Ala Leu Ser Asn Lys Val Leu Ala Glu Tyr Lys Val Pro Gly
145                 150                 155                 160
Glu Ile Val Met Ser Val Lys Glu Met Leu Ser Asp Met Ile Arg Arg
                165                 170                 175
Arg Asn Leu Ile Leu Asn Arg Gly Gly Asp Glu Asn Pro Arg Gly Pro
                180                 185                 190
Val Ser His Glu His Val Asp Trp Cys Arg Glu Phe Val Lys Gly Lys
                195                 200                 205
Tyr Ile Met Ala Phe Asn Pro Pro Trp Gly Asp Ile Asn Lys Ser Gly
                210                 215                 220
Arg Ser Gly Ile Ala Leu Val Ala Thr Gly Leu Ala Lys Leu Ala Glu
225                 230                 235                 240
Thr Glu Gly Lys Gly Ile Phe Asp Glu Ala Lys Lys Thr Val Glu Ala
                245                 250                 255
Leu Asn Gly Tyr Leu Asp Lys His Lys Asp Glu Val Asp Arg Ala Ser
                260                 265                 270
Ala Asp Ser Met Ile Thr Asn Leu Leu Lys His Ile Ala Lys Ala Gln
                275                 280                 285
Glu Leu Tyr Lys Asn Ser Ser Ala Leu Arg Ala Gln Ser Ala Gln Ile
                290                 295                 300
Asp Thr Ala Phe Ser Ser Tyr Tyr Trp Leu Tyr Lys Ala Gly Val Thr
305                 310                 315                 320
Pro Glu Thr Phe Pro Thr Val Ser Gln Phe Leu Phe Glu Leu Gly Lys
                325                 330                 335
Gln Pro Arg Gly Thr Lys Lys Met Lys Lys Ala Leu Leu Ser Thr Pro
                340                 345                 350
Met Lys Trp Gly Lys Lys Leu Tyr Glu Leu Phe Ala Asp Asp Ser Phe
                355                 360                 365
Gln Gln Asn Arg Ile Tyr Met His Pro Ala Val Leu Thr Ala Gly Arg
                370                 375                 380
Ile Ser Glu Met Gly Val Cys Phe Gly Thr Ile Pro Val Ala Asn Pro
385                 390                 395                 400
Asp Asp Ala Ala Gln Gly Ser Gly His Thr Lys Ser Ile Leu Asn Leu
                405                 410                 415
Arg Thr Asn Thr Glu Thr Asn Asn Pro Cys Ala Lys Thr Ile Val Lys
                420                 425                 430
Leu Phe Glu Val Gln Lys Thr Gly Phe Asn Ile Gln Asp Met Asp Ile
                435                 440                 445
Val Ala Ser Glu His Leu Leu His Gln Ser Leu Val Gly Lys Gln Ser
                450                 455                 460
Pro Phe Gln Asn Ala Tyr Asn Val Lys Gly Asn Ala Thr Ser Ala Asn
```

```
                465                 470                 475                 480

Ile Ile

<210> SEQ ID NO 4
<211> LENGTH: 3863
<212> TYPE: PRT
<213> ORGANISM: Artificial sequence
<220> FEATURE:
<223> OTHER INFORMATION: Synthetic construct

<400> SEQUENCE: 4

Met Asp Ala Val Asn Arg Leu Asp Ala Ile Val Trp Glu Asn Ile Glu
1               5                   10                  15

Gly Asn Leu Ser Arg Ala Phe Leu Thr Leu Asp Leu His Ala Phe Phe
            20                  25                  30

Asn Val Asn Lys Glu Val Gly Asp Gly Asn Cys Phe Tyr Arg Ala Leu
        35                  40                  45

Ser Arg Leu His Ser Glu Ser Arg Thr Ser Asn Glu His Leu Tyr Tyr
    50                  55                  60

Arg Leu Leu Ile Pro Asp Ala Val Asp Lys Tyr Phe Asp Ile Glu Pro
65                  70                  75                  80

Glu Ala Ile Gly Leu Gly Leu Asn Lys Gln Glu Tyr Val Ser Lys Ala
                85                  90                  95

Ile Leu Asp Gly Glu Trp Ala Gly Ser Leu Glu Ala Ser Met Leu Ser
            100                 105                 110

Lys Phe Leu Asp Ile Thr Ile Ile Trp Ile Val Asp Asp Ser Gly
        115                 120                 125

Thr Ile Ile Ser Ala Asn Arg Tyr Gly Glu Gly Arg Pro Ser Gln Ala
130                 135                 140

Tyr Asn Leu Cys Met Val Gly Asn Ala His Phe Asp Ser Leu Tyr Ile
145                 150                 155                 160

Arg Val Phe Glu Arg Pro Glu Thr Ala Asn Leu Ser Leu Ile Gly Arg
                165                 170                 175

Leu Glu Ser Ile Glu Glu Leu Ala Ser Leu Glu Glu Ile Pro Cys Leu
            180                 185                 190

Ser Ser Arg Glu Glu Ser His Gln Asn Ser Ser Gly Gly Arg Arg Arg
        195                 200                 205

Glu Leu Ser Lys Leu Glu Val Arg Ala Ile Glu Asn Ser Gln Gly Ile
    210                 215                 220

Pro Leu Arg Ile Gly Arg Ile Val Glu Leu Leu Phe Ser Cys Arg Leu
225                 230                 235                 240

Gly Phe Ser Ile Asp His Lys Ser Leu Lys Ile Thr Ile Leu Asp Asp
                245                 250                 255

Ser Lys Tyr Asp Val Leu Asp Ile Arg Lys Leu Gly His Tyr Leu Leu
            260                 265                 270

Thr Asn Asp Arg Lys Leu Lys Arg Glu Tyr Ser Lys Cys Gly Leu Glu
        275                 280                 285

Ile Asp Asn Ser Val Trp Pro His Leu Asp Glu Ser Tyr Leu Leu Arg
    290                 295                 300

Phe Ala Phe Pro Gly Tyr Gly Leu His Arg Phe Ile Pro Met Leu Leu
305                 310                 315                 320

Pro Ile Phe Val Glu Asp Val Leu Lys Val Cys Leu Ser Ile Leu Leu
                325                 330                 335

Ser Ser Phe Leu Tyr Lys Ser Lys Val Lys Tyr Lys Arg Glu Phe Ile
            340                 345                 350
```

```
Ile Asn Cys Cys Arg Ser Thr Val Thr Ser Gly Lys Arg Val Phe Lys
            355                 360                 365

Ser Ile Arg Lys Ala Thr Thr Ser Asn Leu Tyr Ser Ala Pro Gln Leu
            370                 375                 380

Val Leu Arg Ser Cys Cys Glu His Leu Tyr Lys Arg Leu Ile Val Lys
385                 390                 395                 400

Ile Thr Ser Ser Ile Lys Ala Met Ser Gly Glu Ser His Leu Leu Leu
                405                 410                 415

Arg Asn Leu Asp Phe Ser Ser Leu Ser Leu Ala Asp Tyr Leu Lys Leu
            420                 425                 430

Leu Thr Ala Leu Ala Lys Glu Asp Leu Gln Asp Gln Ser Phe Ile Asn
            435                 440                 445

Lys Glu Leu Ile Ser Leu Asn Arg Leu Asn Lys Thr Leu Lys Glu Ile
            450                 455                 460

Lys Asp Asn Gly Leu Trp Glu Thr Lys Glu Lys Glu Val Ile Ser
465                 470                 475                 480

Lys Phe Phe Glu Glu Lys Asn Met Leu Lys Phe Ile Gly Lys Ser Gly
                485                 490                 495

Lys Ala Ser Gly Ser Phe Gln Ile Gly Asn Val Leu Ala Tyr Ala His
            500                 505                 510

Asn Leu Tyr Leu Asn Lys Asp Ser Leu Gly Leu Ser Asn Asp Asp Met
            515                 520                 525

Glu Gln Ile Ser Ile Glu Ile Arg Lys Leu Gln Leu Leu Gln Glu Gly
            530                 535                 540

Glu Thr Phe Asp Pro Val Ala Ile Ile Cys Asn Lys Leu Glu Gly His
545                 550                 555                 560

Phe Asn Lys Ala Phe Ser Lys Leu Pro Lys Ile Cys Gln Ser Glu Cys
                565                 570                 575

His Val Leu Phe Asp Asp Ile Arg Asn Ser Ser Asn His Ala Ala Ala
            580                 585                 590

Trp Lys His Ala Leu Arg Leu Lys Gly Thr Met Tyr Glu Gly Phe Phe
            595                 600                 605

Ser Gln His Asn Asn Trp Thr Tyr Ile Pro Glu Asp Leu Lys Pro Ser
            610                 615                 620

Leu Met Met Ala Ile Gln Thr Leu Phe Pro Glu Lys Phe Val Arg Phe
625                 630                 635                 640

Leu Glu Lys Thr Gln Leu His Pro Glu Phe Arg Asp Leu Val Pro Asp
                645                 650                 655

Phe Leu Ile Thr Gln Arg Leu Leu Met Glu Gly Asp Asn Pro Lys Val
            660                 665                 670

Asn Ile Ser His Gln Leu Lys Val Ile Glu Gly Leu Gln Glu Ser Val
            675                 680                 685

Glu Ser Ile Pro Met Gly Asp Gln Lys Ile Phe Pro Leu Pro Glu Val
            690                 695                 700

Ala Val Ser Glu Val Arg Ser Ile Glu Gly Ile Leu Asn Arg Ile Glu
705                 710                 715                 720

Thr Gln Ala Arg Gln Ser Asn Ser Lys Asn Asn Arg Phe His Thr Glu
                725                 730                 735

Thr Asn Asn Val Val Leu Asp Gln Glu Arg Ser Tyr Ser Thr His Gln
            740                 745                 750

Leu Leu Phe Ile Glu Val Gly Tyr Gln Thr Asp Val Glu Gly Lys Val
            755                 760                 765
```

```
Leu Thr Asp Thr Val Lys Trp Lys Glu Val Leu Lys Leu Leu Ala Ile
770                 775                 780

Leu Asp Ile Lys Ala Thr Leu Leu Val Cys Ala Asp Asn Ser Lys Thr
785                 790                 795                 800

His Val Asn Asp Trp Trp Ile Asp Glu Glu Leu Val Arg Leu Leu Lys
                    805                 810                 815

Gly Ser Ile Ser His Leu Phe Ser Lys Leu Ser Lys Asn Thr Pro Met
                820                 825                 830

Glu Val Thr Asp Ile Val Val Gly Ser Ile Ser Thr Gln Lys Ile Arg
                835                 840                 845

Ser Phe Leu Lys Ser Gly Thr Ser Thr Lys Thr Pro Leu Ser Thr Lys
850                 855                 860

Asp Val Gln Glu Thr Trp His Ala Met Lys Asp His Ile Leu Asn Arg
865                 870                 875                 880

Glu Thr Gly Val Gln Leu Gly Glu Lys Tyr Ala Asn Pro Met Tyr Ile
                885                 890                 895

Gly Leu Val Glu Gly Val Thr Met Thr Asp Glu Gly Val Gln Leu Ile
                900                 905                 910

Met Asn Leu Leu Lys Asp Asn Ile Lys Thr Leu Thr Asp Glu Phe Glu
                915                 920                 925

Lys Thr Arg Tyr Lys His Glu Ile Asn Lys Ser Ile Glu Thr Gly Ser
930                 935                 940

Lys Met Val Leu Ala Trp Leu Lys Glu Asp Leu Glu Gly Cys Arg Cys
945                 950                 955                 960

Ile Lys Cys Ile Ser Glu Val Leu Thr Ser Val Asp Asp Val Val Ala
                965                 970                 975

Val Gly Ser Lys Leu Ser Ile Leu Ala Arg Ala Cys Ser Leu Ser Ser
                980                 985                 990

His Pro Val Cys Cys His Ser Glu Thr Ile Asn Val Val Asn Ser Ser
            995                 1000                1005

Asn Phe Gln Lys Arg Thr Pro Asp Leu Ser Ser Ile Asn His Leu
    1010                1015                1020

Ser Ile Lys Ser Leu Asp Asp Glu Gly Ser Ile Thr Asp Leu
    1025                1030                1035

Asp Lys Leu Ile Arg Leu Thr Leu Pro Gly Lys Thr Glu Lys Glu
    1040                1045                1050

Lys Lys Ile Lys Arg Ser Val Asp Cys Leu Ile Lys Leu Met Met
    1055                1060                1065

Phe Lys Ser Ser Ile Asn Cys Ile Lys Leu Pro Ser Gly Gln Ile
    1070                1075                1080

Val Met Leu Asp Lys Asn Thr Arg Ser Asn Ile Thr Lys Ser Arg
    1085                1090                1095

Asp Pro Ser Leu Asp Gly Lys Ala Gly Lys Phe Thr Ala Ser Arg
    1100                1105                1110

Glu Glu Thr Val Leu Lys Asn Leu Ser Ser Gln Lys Leu Ser Asn
    1115                1120                1125

Tyr Ser Asp Tyr Val Lys Gln Val Ile Ser Ser Ile Lys Asn
    1130                1135                1140

Val Ala Asn Gln Gln Ala Ser Asn Cys Lys Leu Asn Asp Leu Trp
    1145                1150                1155

Val Glu Lys Leu Val Asn Asp Leu Asp Val Pro Leu Gln Asn Glu
    1160                1165                1170

Glu Val Ile Glu Lys Val Lys Arg Ser Val Glu Gln Arg Lys Lys
```

-continued

```
           1175                1180                1185
Tyr Ile Arg Asn Asn Asp Lys Leu Ile Ile Arg Ser Thr His Glu
       1190                1195                1200
Met Ile Ser Tyr Leu Thr Asn Phe Arg Gly Ser Leu Cys Ala Glu
       1205                1210                1215
Pro Ser Asn Arg Leu Phe Ser Val Asp Cys Val Leu Phe Lys Glu
       1220                1225                1230
Val Ile Ser Glu Ala Met Leu Arg Tyr Gln Ser Thr Ala Tyr Gln
       1235                1240                1245
Gly Cys Val Asp His Met Leu Lys Leu Leu Glu Leu Leu Leu Glu
       1250                1255                1260
Phe Thr Trp Phe Gln Glu Val Leu Val Tyr Ser Lys Val Cys Glu
       1265                1270                1275
Thr Phe Leu Arg Ile Cys Thr Glu Phe Asn Arg Ala Gly Leu Lys
       1280                1285                1290
Leu Leu Lys Val Arg His Leu Asn Ile Asn Ile Ala Val Lys Leu
       1295                1300                1305
Pro Ala Asn Lys Lys Gln Asn Met Gln Cys Arg Ile Tyr Asp His
       1310                1315                1320
Asn Met Gln His Leu Thr Asp Val Phe Phe Leu Asn Arg Arg Gln
       1325                1330                1335
Ala Ile Ile Gly Ala Ala Tyr Pro Tyr Ile Leu Leu Val Leu Tyr
       1340                1345                1350
Ile Gln Ile Leu Gln Gln Gln Arg Cys Ile Glu Glu Leu Asp Asn
       1355                1360                1365
Arg Ser Ser His Val Gln Gly Ile Arg Asn Lys Ser Asp Lys Leu
       1370                1375                1380
Leu Thr Cys Phe Met Asn Glu Ala Ala Ser Val Leu Asn Gly His
       1385                1390                1395
Phe Glu Glu Ala Tyr Lys Glu Arg Phe Gln Ile Cys Lys Leu Ser
       1400                1405                1410
Gly Asn Phe Ser Thr Lys Pro Pro His Glu Asn Phe Ile Asn Val
       1415                1420                1425
Phe Ala Gly Leu Asn Leu Val Tyr Gly Val Ile Met Arg Asp Ser
       1430                1435                1440
Phe Leu Ala Asn Ser Gln Pro Gln Asn Lys Gln Leu Gln Met Leu
       1445                1450                1455
Arg Tyr Gly Met Leu Asn Gly Leu Ser Arg Leu Ser Cys Pro Leu
       1460                1465                1470
Glu Leu Gly Lys Lys Phe Ser Ser Ser Cys Arg Arg Ile Glu Asp
       1475                1480                1485
Asn Leu Ser Arg Val Tyr Leu Gln Ser Thr Ile Tyr Cys Ser Met
       1490                1495                1500
Arg Asp Val Glu Lys Asn Val Pro Ala Trp Lys Glu Val Asp Leu
       1505                1510                1515
Cys Pro Ser Val Thr Ile Pro Cys Phe Ser Ile Tyr Gly Leu Phe
       1520                1525                1530
Val Asn Ser Asp Arg Gln Leu Ile Phe Asp Ile Tyr Asn Val His
       1535                1540                1545
Ile Tyr Asn Lys Glu Met Asp Asn Phe Asp Glu Gly Cys Ile Ser
       1550                1555                1560
Val Leu Glu Glu Thr Ala Asp Arg His Met Asn Trp Glu Leu Asp
       1565                1570                1575
```

```
Leu Glu Lys Asn Trp Arg Asp Asp His Asp Gln Arg Gly Thr Arg
    1580            1585                1590

Leu Leu Leu Gly Ile Pro Asn Val His Lys Ser Lys Cys Gln Asp
    1595            1600                1605

Pro Arg Gln Ile Glu Asp Ser Lys Ser Asp Ala Ser Ser Leu Lys
    1610            1615                1620

Asp Ser Cys Leu Thr Arg Arg Ser Ser Ser Asn Arg Leu Ser
    1625            1630                1635

Thr Ser Ser Leu Ile Asn Arg Tyr Thr Thr Ile Ile Lys Pro Ile
    1640            1645                1650

Glu Ile Asp Ser Gly Ile Phe Leu Glu Ser Asp Ile Leu Arg Gln
    1655            1660                1665

Gly Arg Ala Ser Ala Thr Gly Gly Pro Lys Tyr Tyr Ala Tyr Thr
    1670            1675                1680

Pro Asn Lys Ala Ser Ile Leu Lys Asp Cys Leu Thr Ile Ile Lys
    1685            1690                1695

Lys Asn Pro Asn Tyr Thr Phe Gly Ser Phe Glu Val Ile Gln Ala
    1700            1705                1710

Val Thr Glu Phe Ala Arg Ser Lys Tyr Pro Gln Glu Asn Ile Cys
    1715            1720                1725

Lys Ala Lys Arg Asp Pro Lys Asn Trp Val Ser Ile Ser Glu Val
    1730            1735                1740

Thr Glu Thr Thr Ser Ile Val Ala Thr Pro Lys Thr Glu Phe Tyr
    1745            1750                1755

Val Lys Asp Cys Phe Lys Thr Asn Ile Ser Asn Gln Asn Lys Lys
    1760            1765                1770

Leu Ser Lys Met Ile Lys Asn Lys Phe Lys Lys Leu Gly Ser Leu
    1775            1780                1785

Phe Ser Asp Asn Asp Ile Ser Lys Lys Asp Cys Thr Val Leu Leu
    1790            1795                1800

Ser Thr Val Asp Gly Leu Thr Ala Lys Gln Lys Gln Asp Ile Thr
    1805            1810                1815

Asn Ala Val Phe Glu Pro Ser Lys Leu Ser Leu Tyr Asn Trp Ser
    1820            1825                1830

Tyr Ile Leu Thr Lys Gly Val Phe Asp Val Leu Leu Thr His Asp
    1835            1840                1845

Gly Asn Ile Ile Tyr Cys Trp Ile Lys Ser Leu Ser Leu Met Ala
    1850            1855                1860

Lys Ser Arg Leu Arg Lys His Leu Ser Phe Met Ser Val Gly Asn
    1865            1870                1875

Asp Thr Val Pro Glu Glu Gly Phe Phe Ser Ser Asn Glu Ile Glu
    1880            1885                1890

Ser Leu Ile Thr Ile Arg Arg Leu Leu Ile Cys Glu Glu His Glu
    1895            1900                1905

Glu Ile Ser Thr Ile Cys Ala Ser Asn Leu Val Ser Ala Trp Ile
    1910            1915                1920

Lys Cys Ile Phe Val Lys Pro Ile Asp Asp Val Tyr Asn Asp Lys
    1925            1930                1935

Leu Leu Ser Asp Met Leu Ser Ala Ala Glu Glu Leu Tyr Thr Leu
    1940            1945                1950

Arg Leu Lys His Met Ile Leu Ile Arg Asp Lys Lys Glu Asn Ser
    1955            1960                1965
```

-continued

```
Tyr Thr Ser Phe Ile Lys Glu Glu Leu Ile Leu Lys Gly Glu Glu
    1970            1975                1980

Arg Val Phe Leu Lys Asn Tyr Asp Lys Leu Ile Val Lys Ser Val
    1985            1990                1995

Asn Phe Leu Leu Phe Ala Ala Val Ser Ala Pro Trp Cys Met His
    2000            2005                2010

Tyr Lys Ala Leu Glu Ser Tyr Ile Val Lys His Pro Glu Ile Leu
    2015            2020                2025

Asp Ile Gly Asp Thr Glu Thr Tyr Ser Asn Ser Ile Leu Ser Leu
    2030            2035                2040

Thr Leu Ser Asn Val Val Tyr Glu Leu Tyr Lys Ile Tyr Cys Gly
    2045            2050                2055

Lys Lys Lys Glu Val Val Asp Lys Arg Lys Met Ile Ser Leu Arg
    2060            2065                2070

Phe Phe Val Arg Tyr Leu Thr Thr Met Phe Ala Ser Asn Ser Glu
    2075            2080                2085

Pro Phe Ser Thr Ser Leu Asn Glu Asp Glu Ile Asp Val Gly Lys
    2090            2095                2100

Thr Asn Asp Ile Glu Glu Lys Leu Leu Ser Gln Thr Lys Leu Val
    2105            2110                2115

Phe Ala Lys Leu Gly Leu Gly Asp Lys Asn Tyr Asp Phe Ile Trp
    2120            2125                2130

Thr Val Gln Met Ile Ala Asn Ser Asn Phe Asn Val Cys Lys Lys
    2135            2140                2145

Leu Thr Gly Arg Ser Glu Gly Glu Arg Leu Pro Arg Ser Ile Arg
    2150            2155                2160

Ser Lys Val Val Tyr Glu Met Val Lys Leu Val Gly Glu Ser Gly
    2165            2170                2175

Met Ala Ile Leu Gln Gln Leu Ala Phe Ala Lys Ser Leu Asn Tyr
    2180            2185                2190

Asn His Arg Phe Phe Ser Val Leu Ala Pro Lys Ala Gln Leu Gly
    2195            2200                2205

Gly Ser Arg Asp Leu Leu Val Gln Glu Thr Gly Thr Lys Ile Ile
    2210            2215                2220

His Ala Ala Thr Glu Ser Phe Ser Arg Ser Leu Leu Arg Thr Thr
    2225            2230                2235

Asn Asp Asp Gly Leu Thr Asn Gln Asn Leu Lys Glu Thr Val Leu
    2240            2245                2250

Asn His Ala Leu Asp Thr Leu Thr Thr Met Arg Ser Val Asp Gly
    2255            2260                2265

Glu Leu Leu Lys Gly Ser Ser Asn Leu Ile Gln Phe Tyr Lys Val
    2270            2275                2280

Ile Cys Ile Ser Gly Asp Asn Thr Lys Trp Gly Pro Ile His Cys
    2285            2290                2295

Cys Ser Phe Phe Ser Gly Met Met Gln Gln Leu Leu Lys Asp His
    2300            2305                2310

Pro Asp Trp Ser Ala Phe Tyr Arg Leu Thr Phe Ile Lys Asn Leu
    2315            2320                2325

Cys Arg Gln Ile Glu Ile Pro Ala Ala Ser Ile Lys Lys Ile Ile
    2330            2335                2340

Asn Val Ala Lys Leu Lys Met Glu His Asn Gln Asp Ile Asp Cys
    2345            2350                2355

Leu Ser Glu Glu Gln Ala Gln Asp Leu Leu Lys Glu Ser Ala Asp
```

```
            2360                2365                2370

Asp Trp Ser Ala Leu Pro Tyr Val Lys Phe Leu Ile Lys Thr Tyr
    2375                2380                2385

Leu Arg Lys Gly Lys Leu Ala Met Asn Ser Tyr Asn His Met Gly
    2390                2395                2400

Gln Gly Ile His His Ala Thr Ser Ser Ile Leu Thr Ser Ile Met
    2405                2410                2415

Ala Glu Thr Phe Glu Glu Leu Cys Thr His Tyr Phe Lys Ser Ile
    2420                2425                2430

Phe Pro Asn Leu Thr Val Asp Ile Asn His Ala Gly Ser Ser Asp
    2435                2440                2445

Asp Tyr Ala Lys Thr Ile Ile Val Thr Gly Val Leu Asp Arg Glu
    2450                2455                2460

Gln Tyr Glu Leu Tyr Asp Ser Ile Phe Trp Asn His Ala Cys Arg
    2465                2470                2475

Phe Lys Asn Tyr Ile Ala Ala Val Asn Arg Cys Cys Gln Met Lys
    2480                2485                2490

Asp Ser Ala Lys Thr Leu Val Gly Asp Cys Phe Leu Glu Phe Tyr
    2495                2500                2505

Ser Glu Phe Met Met Gly Tyr Arg Val Thr Pro Ala Val Ile Lys
    2510                2515                2520

Phe Ile Phe Thr Gly Leu Met Asn Ser Ser Val Thr Ser Pro Ser
    2525                2530                2535

Ser Leu Thr Gln Ala Cys His Val Ser Ser Gln Gln Ala Met Tyr
    2540                2545                2550

Asn Ser Val Pro Met Leu Thr Asn Ile Thr Phe Thr Leu Cys Arg
    2555                2560                2565

Gln Gln Met Phe Phe Asn His Val Glu Gly Phe Ile Arg Lys Phe
    2570                2575                2580

Gly Pro Leu Thr Leu Gly Ser Val Ser Gln Phe Gly Arg Leu Tyr
    2585                2590                2595

Cys Pro Arg Tyr Ser Asn Leu Val Asn Thr Ser Val Thr Ile Glu
    2600                2605                2610

Asp Cys Glu Ser Ile Val Asn Ala Cys Asn Ser Ile Leu Lys Trp
    2615                2620                2625

Asn Asp Leu Phe Glu Thr Leu Ala Lys Ser Glu Ile Glu Glu Glu
    2630                2635                2640

Phe Glu Lys Asp Arg Ser Lys Arg Ser Leu Ser Ser Ser Glu Thr
    2645                2650                2655

Ser Ser Phe Lys Ser Gly Glu Ser Ser Thr Glu Phe Ser Phe Ile
    2660                2665                2670

His Arg Arg Leu Leu Thr Asp Asp Glu Leu Lys Phe Ile Asp Ile
    2675                2680                2685

Ser Ser Glu Cys Ala Arg Tyr Thr Asn Ala Gln Ala Val Glu Glu
    2690                2695                2700

Arg Leu Gly Leu Tyr Tyr Trp Asp Thr Arg Asp Gln Asn Pro Lys
    2705                2710                2715

Asn Lys Asp Phe Ile Leu Asn Ser Thr Leu Cys Asn Ser Cys Glu
    2720                2725                2730

Trp Ile Lys Lys Gly Lys Asp Lys Cys Ala Leu Glu Ala Ile Val
    2735                2740                2745

Arg Ile Gln Met Leu Leu Arg Leu Leu Cys Phe Gly His Tyr Arg
    2750                2755                2760
```

```
Ser Phe Ser Gly Gln Gly Leu Glu Arg Gln Val Lys Ser Ser Leu
2765                2770                2775

Asn Arg Asp Glu Asn Gln Ile Ile Glu Asp Pro Met Ile Gln Leu
2780                2785                2790

Ile Pro Glu Lys Leu Arg Arg Glu Leu Glu Arg Leu Gly Leu Ser
2795                2800                2805

Lys Met Ser Val Glu Glu Leu Leu Pro Lys Ser Leu Ser Cys Ser
2810                2815                2820

Ser Ile Cys Gln Val Val Ala His Arg Leu Ile Ser Leu Asn Val
2825                2830                2835

Ser Thr Glu Ser Tyr Val Ala Glu Val Ser Arg Leu Lys Gln Thr
2840                2845                2850

Leu Thr Ala Arg Asn Val Leu Phe Gly Leu Ala Gly Gly Ile Lys
2855                2860                2865

Glu Leu Ser Ile Pro Ile Tyr Thr Ile Phe Met Lys Ser Tyr Phe
2870                2875                2880

Phe Lys Asp Asn Val Phe Met Asp Leu Thr Asp Arg Trp Leu Thr
2885                2890                2895

Gln His Ser Ala Asn Tyr Arg Asp Ser Ser Gly Lys Lys Leu Asp
2900                2905                2910

Gly Lys Ile Val Thr Lys Tyr Pro His Trp Leu Ser Val Phe Met
2915                2920                2925

Asn Cys Leu Val Ser Met Asp Ser Thr Ser Glu Leu Thr Asp Lys
2930                2935                2940

Ser Leu Phe Asn Asp Ser Leu Lys Cys Ile Gly Val Thr Arg Asn
2945                2950                2955

Leu Asn Asn Gln Arg Met Leu Thr Ile Ile Lys Ser His Leu Glu
2960                2965                2970

Ser Val Ser Ser Glu Leu Lys Tyr Phe Ile Leu Gln Phe Ser Asn
2975                2980                2985

Leu Asn Arg Arg Lys Met Arg Ile Val Glu Ser Arg Pro Ala Glu
2990                2995                3000

Cys Glu Met Glu Ala Asn Lys Val Val Ile Thr Lys Ser Ser Leu
3005                3010                3015

Phe Thr Ala Gly Asp Gly Val Lys Leu Asn Asn Asn Pro Ala Val
3020                3025                3030

Val Ile Gly Phe Leu Leu Asp Glu Ser Ser Ile Ser Glu Val Lys
3035                3040                3045

Pro Ser Arg Val Asp Phe Ala Asn Leu Met Lys Asp Arg Phe Lys
3050                3055                3060

Leu Ser Gln Tyr Phe Pro Ser Val Asp Leu Val Leu Lys Ser Leu
3065                3070                3075

Lys Arg Glu Ser Asp Gln His Leu Gln Val Cys Ser Thr Pro Asp
3080                3085                3090

Tyr Ser Val Ser Thr Lys Tyr Val Asn Tyr Leu Thr Leu Leu Cys
3095                3100                3105

Arg Met Met Ile Gln Thr Asn Ser Ser Leu Thr Val Phe Tyr Met
3110                3115                3120

Ile Lys Ser Asn Lys Leu Arg Asn Glu Pro Thr Val Ser Asp Leu
3125                3130                3135

Ile Ser Tyr Gly Ile Lys Glu Gly Arg Tyr Leu Lys Leu Pro Glu
3140                3145                3150
```

```
Ala Glu Ile Asp Thr Ser Thr Tyr Ser Val Lys Tyr Trp Lys Ile
3155                3160                3165

Ile Gln Cys Ile Ser Cys Ile Gly Leu Leu Pro Met Ser Asp Ser
3170                3175                3180

Ser Arg Arg Asp Ile Leu Phe Gly Phe Met Asn Trp Lys Val Thr
3185                3190                3195

Cys Cys Gly Asp Ser Gly Cys Pro Ile Phe Lys Glu Glu Ala Ser
3200                3205                3210

Val Leu Ser Glu Phe Asn Asn Gln Thr Ile Leu His Val Leu Ala
3215                3220                3225

Ser Glu Val His Leu Ile Lys Asp Lys His Glu Arg Glu Ser Ile
3230                3235                3240

Ile Asn Leu Val Asp Tyr Val Thr Ser Pro Ser Glu Leu Ile Lys
3245                3250                3255

Lys Lys Pro Tyr Leu Gly Thr Thr Ala Ser Phe Lys Thr Trp Gly
3260                3265                3270

Gly Gly Gly Arg Glu Gly Arg Phe Thr Tyr Ser Ser Arg Ser Gly
3275                3280                3285

Glu Ser Thr Gly Ile Phe Val Gly Gly Lys Leu His Ile Tyr Leu
3290                3295                3300

Ser Asn Asp Thr Ile Ser Leu Leu Asp Glu Val Glu Arg Asn Val
3305                3310                3315

Leu Gly Trp Leu Ser Gln Arg Arg Thr Glu Ile Phe Thr Ile Glu
3320                3325                3330

Gln His Glu Ser Phe Val Asn Leu Leu Pro Ser Ile Ala Glu Phe
3335                3340                3345

Gly Ser Lys Ser Ser Asp Gly Lys Val Val Gly Val Ala Val Asp
3350                3355                3360

Lys Ser Asn Pro Arg Phe Leu Arg Tyr Thr Asp Pro Lys Gly Ser
3365                3370                3375

Ala Lys Asn His Ile Leu Arg Ile Lys Lys Gln Ile Leu Thr Val
3380                3385                3390

Lys Lys Ile Asn Thr Val Glu Phe Glu Ser Asp Pro Lys Leu Val
3395                3400                3405

Trp Ser Lys Ser Gly Val Ser Ile Val Phe Asp Glu Ile Ser Thr
3410                3415                3420

Glu Val Thr Tyr His Glu Arg Ile Gly Leu Ile Lys Gly Leu Leu
3425                3430                3435

Ala Asn Val Ile Glu Asn Lys Thr Leu Pro Ser Leu Tyr Gln Asp
3440                3445                3450

Thr Gln Ile Cys Leu Ser Lys Leu Lys Phe Ser Asn Thr Ile Leu
3455                3460                3465

Met Asn Ser Ile Ala Leu Leu His Ala Tyr Leu Val His Ala Pro
3470                3475                3480

Leu Asp Ala Phe Asn Ser Val Gly Ser Lys Arg Thr Val Leu Lys
3485                3490                3495

Thr Phe Leu Glu Asn Arg Leu Leu Val Gln Ser Glu Gly Gln Thr
3500                3505                3510

Val Lys Gln Thr Phe Gly Ala Ala Asp Leu His Phe His Lys Gln
3515                3520                3525

Thr Pro His Asn Ser Glu Ala Met Thr Leu Leu Thr Ile Ser Lys
3530                3535                3540

Thr Leu Thr Glu Asn Met Leu Pro Phe Asp Ser Trp Pro Glu Val
```

```
Gln Ala Gln Leu Glu Thr Cys Gly Leu Ser Asn Phe Leu Leu Thr
    3560            3565                3570

Phe Lys Ser Glu Pro Ala Lys Gly Tyr Leu Met Trp Asp Leu Gln
    3575            3580                3585

Thr Ser Leu Val Pro Asp Arg Leu Lys Ile Leu Asp Ile Lys Asp
    3590            3595                3600

Val Val Ser Ser Val Asn Ser Gly Val Leu Val Pro Ala Phe Leu
    3605            3610                3615

Pro Phe Leu Phe Glu Pro Ala Leu Leu Lys Glu Leu Thr Asn Thr
    3620            3625                3630

Ser Leu Ala Ala Leu His Thr Leu Ser Ser Leu Ser Ile Thr Asn
    3635            3640                3645

Glu Gln Val Asp Arg Ile Val Ile Ser Thr Ile Tyr Cys Phe Gln
    3650            3655                3660

Thr Glu Thr Lys Glu Arg Ser Ser Leu Lys Phe Arg Pro Ser Ser
    3665            3670                3675

Leu Leu Gly Leu Cys Gln Arg Gln Thr Phe Arg Ile Gly Asn Arg
    3680            3685                3690

Leu Glu Val Ser Ala Val Ala Asp Phe Asp Glu Val Ser Leu Met
    3695            3700                3705

Ile Thr Ile Arg Cys Thr Asp Pro Gln Asp Gln Ser Met Pro Arg
    3710            3715                3720

Asp Lys Lys Gln Leu Arg Ile Ile Lys Asn Phe Asn Ser Ser Val
    3725            3730                3735

Arg Cys Leu Met Ile Asp Gln Ser Val Asp Val Lys Lys Ile Lys
    3740            3745                3750

Glu Ser Phe Asn Asp Leu Thr Met Glu Ser Asp His Lys Gly Thr
    3755            3760                3765

Lys Ile Lys Phe Thr Ala Lys Pro Asn Asp Asn Asn Gln Phe Asp
    3770            3775                3780

Tyr Leu Ala Leu Met Tyr Glu Gly Lys Glu Arg Leu Ala Glu Tyr
    3785            3790                3795

Thr Ser Ile Ala Asn Phe Val Leu Phe Leu Leu Gly Cys Lys His
    3800            3805                3810

Asn Ser Phe Glu Glu Pro Asn Thr Ile Lys Gly Glu Glu Asp Ile
    3815            3820                3825

Ser Ile Asp Ser Ile Ile Asp Val Val Glu Thr Ile Asn Glu Gln
    3830            3835                3840

Val Phe Gln Asp Glu Pro Val Arg Leu Ser Asp Lys Val Tyr Phe
    3845            3850                3855

Ser Asp Asp Glu Tyr
    3860

<210> SEQ ID NO 5
<211> LENGTH: 1296
<212> TYPE: PRT
<213> ORGANISM: Artificial sequence
<220> FEATURE:
<223> OTHER INFORMATION: Synthetic construct

<400> SEQUENCE: 5

Met Val Thr Lys Trp Val Val Ala Ala Val Leu Val Ile Lys Trp Cys
1               5                   10                  15

Leu Leu Met Lys Val Thr Leu Ser Ser Thr Ile Ser Thr Thr Pro Thr
```

-continued

```
                 20                  25                  30
Thr Ser Thr Thr Asn Ser Thr Gln Ser Thr Asn Asn Thr Asn Ala Thr
             35                  40                  45
Ser Ser Ala Pro Asn Ser Thr Gln Pro Asn Thr Thr Ser Ser Pro Gly
         50                  55                  60
Ser Thr Asn Gln Thr Leu Asn Ala Ser Ser Ser Asn Gln Thr Gln
 65                  70                  75                  80
Gln Glu Ile Ala Arg Ser Val Val Asn Tyr Thr Ser Gly Glu Trp Ala
                 85                  90                  95
Pro Thr Leu Glu Ala Leu Tyr Thr Ser Gly Pro Cys Asp Lys Leu
             100                 105                 110
Asn Lys Ser Trp Cys Lys Leu Glu Val Gly Lys Thr His Gly Leu Ser
             115                 120                 125
Pro Tyr Val Lys His Leu Tyr Asn Leu Ser Tyr Asp Gly Tyr Asn Ala
             130                 135                 140
Leu Cys Glu Thr Lys Lys Gly Asn Tyr Gly Phe Val Trp Lys Trp Lys
145                 150                 155                 160
Phe Thr Phe Thr Val Thr Thr Gly Pro Glu Arg Val Leu Leu Arg Asp
                 165                 170                 175
Val Gln Cys Ser Asn Val Val Tyr Asp Gly Ile Thr Lys Asp Gly Tyr
             180                 185                 190
Leu Ile His Phe Leu Phe Gly Gly Arg Val His Phe Thr Asp Cys
             195                 200                 205
Lys Tyr Ala Val Ile Thr Lys Asn Cys Lys Ile Glu Ser Ser Lys Asp
             210                 215                 220
Gly Pro Val Pro Leu Ala Gly Tyr Gly Asn Trp Thr Thr Ala Thr Tyr
225                 230                 235                 240
Ser Leu Phe Leu Gln Asn Lys Tyr Ala Asn Glu Ala Cys Lys Ile Lys
             245                 250                 255
Phe Pro Cys Leu Asn Lys Gly Lys Ala Leu Gly Asn Gly Phe Glu
             260                 265                 270
Leu Lys Gly Tyr Phe Thr Thr Gly Leu Thr Arg Pro Glu Thr Ser Gly
             275                 280                 285
Arg Arg Leu Leu Ser Thr Gly Asp Ser Glu Pro Glu Asp Asp Cys Gly
             290                 295                 300
Thr His Ser His Met Lys Gln Ile Thr Asn His His Leu Ile Thr Asp
305                 310                 315                 320
Phe Lys Asp Gly Pro Gly Asp Val Val Ser Ile Cys Asn Gly Thr His
             325                 330                 335
Phe Phe His Gly Arg Met Pro Asn Asn Leu Gly Cys Tyr Ser Ile Arg
             340                 345                 350
Ser Ile Lys Val Ser His His Cys Gly His His Lys Thr Lys Cys Thr
             355                 360                 365
Ile Glu Pro Glu Leu Lys Gln Cys Ser His Gly Lys Cys Ile Ser Ile
             370                 375                 380
Arg Met Ser Asn Lys Gly Ile Val Arg Leu Ser Arg Gly Ser Ser Thr
385                 390                 395                 400
Glu Thr Ile Lys Cys Gly Thr Cys Leu Ile Pro Pro Leu Asp Gly
             405                 410                 415
Glu Gly Asp Ile Ile Val Asp Cys Pro Gly Gly Thr Gln His Phe Leu
             420                 425                 430
Gln Arg Asn Ile Val Asp Leu Asp Cys Pro Thr Tyr Pro Tyr Phe Gln
             435                 440                 445
```

-continued

```
Glu Phe Met Leu Tyr Ile Cys Arg Ala Ser His Arg Pro Lys Thr Thr
    450                 455                 460
Ile Gly Phe Phe Leu Trp Met Ser Val Gly Tyr Ile Ile Leu Ser Ala
465                 470                 475                 480
Cys Cys Ser Phe Thr Leu Leu Leu Arg Leu Leu Cys Lys Gly Val
                485                 490                 495
Glu Leu Cys Lys Thr Arg Phe Thr Ser Thr Gln Glu Val Cys Glu Val
            500                 505                 510
Cys Lys Gln Gln Ile Ser Gly Asn Leu Ser Lys Gln Leu His Glu Ala
            515                 520                 525
Asn Cys Lys Asn Gly Leu Cys Pro Tyr Cys Ser Asn Arg Leu Pro Glu
530                 535                 540
Ser Ser Leu Tyr Lys His Ala Glu Val Cys Pro Arg Lys Lys Pro Thr
545                 550                 555                 560
Val Glu Ala Ile Arg Glu His Glu Asn Tyr Asn Ser Thr Pro Trp Leu
                565                 570                 575
Phe Val Phe Ile Phe Gly Val Ser Glu Tyr Ser Gly Thr Leu Ile Lys
                580                 585                 590
Arg Ser Val Trp Ile Ile Val Leu Leu Ser Leu Leu Val Ala Leu
            595                 600                 605
Ser Pro Val Tyr Gly Glu Gln Asp Phe Leu Phe Glu Gly Ile Gly Glu
    610                 615                 620
Glu Gln Leu Glu Lys Gly Leu Trp Glu Asp Glu Val Glu Leu Val Glu
625                 630                 635                 640
Gly Cys His Gln Glu Cys Phe Val Val Glu Ala Glu Cys Leu Cys Pro
                645                 650                 655
Ser Phe Gln Ala Gly Arg Gln Leu Leu Phe Tyr His Leu Met Asn Lys
                660                 665                 670
Gln Ile Arg Thr Ser Asn Lys Leu Lys Leu Leu Ser Ser Val Ser Leu
            675                 680                 685
Glu Thr Pro Trp Gly Val Val Lys Ile Glu Lys Gly Phe Lys Pro Thr
            690                 695                 700
Ser Ser Met Ala Asn Leu Gln Leu Ser Trp Ser Ser Glu Glu Val
705                 710                 715                 720
Gly Gly Lys Val Ile Leu Ser Gly Arg Ser Thr Ser Ile Ile Lys Leu
                725                 730                 735
Lys Glu Arg Thr Gly Met Val Trp Glu Leu Ser Ser Ser Arg Ala Ser
            740                 745                 750
Glu Lys Lys Lys Leu Val Val Ser Ile Met Asp Phe Ser Gln Glu Tyr
    755                 760                 765
Lys Thr Gln Phe Gln Tyr Leu Thr Gly Asp Arg Leu Val Ser Glu Trp
    770                 775                 780
Pro Arg Ala Thr Cys Thr Gly Pro Cys Pro Asp Arg Cys Ala Cys His
785                 790                 795                 800
Thr Ser Thr Cys Thr Trp Lys Thr Trp Pro Asn Ser Arg Lys Trp Thr
                805                 810                 815
Cys Asn Pro Thr Trp Cys Trp Gly Val Gly Thr Gly Cys Thr Cys Cys
            820                 825                 830
Gly Met Asp Val Glu Lys Pro Phe Gln Asn Tyr Leu Val Ala Lys Trp
            835                 840                 845
Ser Thr Glu Tyr Ile Lys Thr Asp Val Ile Val Cys Val Glu Val Ser
    850                 855                 860
```

-continued

Glu Glu Glu Arg His Cys Asp Leu Ile Gln Ala Gly Ser Arg Phe His
865                 870                 875                 880

Leu Gly Pro Ile Thr Val Leu Val Ser Asp Pro Gln Ser Val Ala Lys
            885                 890                 895

Lys Leu Pro Ser Glu Val Ile Thr Leu His Lys Val Gln Gly Gly Glu
        900                 905                 910

Val Asp Leu Met His Val Asn Lys Ile Leu Thr Ala Asn Ser Leu Cys
        915                 920                 925

Lys Pro Gln Ser Cys Thr His Gly Ser Pro Gly Asp Ile Gln Ile Phe
930                 935                 940

Lys Pro Asp Tyr Leu Val Lys Tyr Ser Ile Ser Lys Arg Ile Asn Ala
945                 950                 955                 960

Ile Glu Asp His Ser Trp Ala Asn Asp Thr Trp Met Ser Trp Gln Gly
                965                 970                 975

Ser Asp Leu Asp Tyr Tyr Cys Thr Thr Gly Ser Trp Pro Thr Cys Thr
            980                 985                 990

Phe Ser Gly Val Val Lys Gln Asn Ser Asp Ala Phe Lys Asn Leu Glu
        995                 1000                1005

Thr Leu Glu Phe Asn Leu Met Glu Glu Phe Phe Phe His Ser Ser
    1010                1015                1020

Arg Val Glu Val Lys Gly Ser Thr Leu Gly Phe Pro Val Lys Ser
    1025                1030                1035

Arg Pro Lys Glu Gly Gly Glu Leu Ser Val Leu Val Glu Val
    1040                1045                1050

Asn Gly Leu Glu Leu His Ser Lys Leu Ile Asp Pro Leu Gly Leu
    1055                1060                1065

Ser Leu Lys Ile Thr Ser Cys Lys Gly Cys Tyr Ser Cys Ser Ser
    1070                1075                1080

Gly Phe Tyr Cys Asp Val Val Leu Asn Ile Glu Glu Pro Ser Glu
    1085                1090                1095

Met Thr Val His Val Glu Cys Asn Asn Pro Asn Ile Val Leu Thr
    1100                1105                1110

Glu Ser Ser Leu Ile Ala Lys Ser Gly Ala Leu Ser Ala Ser Lys
    1115                1120                1125

Val Lys Gly Phe Ser Ala Leu Arg Glu Thr Arg Leu Cys Leu Ile
    1130                1135                1140

Leu Gln Glu Ser Lys Val Thr Lys Lys Glu Val Lys Asp Cys Ile
    1145                1150                1155

Asp Ile Lys Leu Glu Glu Pro Lys Asp Val Ile Ile Glu Arg Gly
    1160                1165                1170

Ser Thr Leu Leu Ser His Gln Asn Asp Thr Cys Thr Ser Gly Phe
    1175                1180                1185

Gly Cys Trp Leu Gly Asn Ala Lys Ser Phe Ser Leu Gly Leu Gly
    1190                1195                1200

Met Met Phe Gln Asn Tyr Phe Gly Ser Ile Ile Ile Gly Leu Ile
    1205                1210                1215

Ile Phe Val Leu Pro Val Ile Ala Leu Leu Val Phe Phe Cys Leu
    1220                1225                1230

Gly Lys Arg Ile Leu Ile Cys Arg Arg Leu Lys His Cys Phe Arg
    1235                1240                1245

Ser Asn Leu Glu Asp Lys Gln Lys Phe Lys Gln Leu Leu Thr Glu
    1250                1255                1260

Leu Lys His Ser Asn Leu Leu Lys Ile Met Lys Glu Asp Ala Lys

```
                    1265                1270                 1275
Ser Ser Trp Arg Gly Leu Ala Asn Lys Ala Leu Gly Lys Thr Pro
    1280                1285                1290

Lys Met Asp
    1295

<210> SEQ ID NO 6
<211> LENGTH: 630
<212> TYPE: PRT
<213> ORGANISM: Artificial sequence
<220> FEATURE:
<223> OTHER INFORMATION: Synthetic construct

<400> SEQUENCE: 6

Met Glu Asn Leu Ile Asp Phe Ser Gly Arg Asp Gly Leu Asp Arg Trp
1               5                   10                  15

Leu Arg Ala Thr Phe Pro Asp Val Ile Leu Ser Val Gly Leu Thr Asn
            20                  25                  30

Tyr Gly Ser Leu Met Thr Ser Val Pro Asp Leu Ser His Phe Glu Gln
        35                  40                  45

Met Ala Arg Gln Ala Lys Ser Glu Gln Glu Lys Asp Ala Val Tyr Ser
    50                  55                  60

Lys Ala Leu Thr Glu Ala Thr Arg Lys Ala Ala Pro Ile Ala Ala Cys
65                  70                  75                  80

Ala Leu Thr Ser Ser Lys Glu Met Val Lys Lys Gly Leu Gln Trp Phe
                85                  90                  95

Glu Asp Gln Ile Ile Ser Glu Asp Gly Asn Phe Leu Val Trp His Gln
            100                 105                 110

Asn Tyr Glu Gln Leu Lys Lys Ala Pro Pro Ser Phe Glu Gln Leu Met
        115                 120                 125

Gly Tyr Gln Met Ser Ala Leu Asn Trp Arg Gln Ser Val Gly Tyr Gly
    130                 135                 140

Gln Leu Glu Glu Thr Ala Val Leu Val Ser Gln Val Ile Ala Gln Phe
145                 150                 155                 160

Ser Val Pro Gly Thr Leu Val Val Thr Val Gln Glu Met Ile Lys Asp
                165                 170                 175

Met Ile Ala Arg Arg Gly Gly Pro Lys Arg Gly Val Ser Glu Glu
            180                 185                 190

His Val Arg Cys Cys Val Asp Ile Met Asn Gly Asn Leu Ser Ala Leu
        195                 200                 205

Ile Asn Pro Ala Trp Gly Asp Ile Asp Lys Lys Asn Lys Asn Gly Leu
    210                 215                 220

Met Leu Leu Thr Thr Gly Ile Ala Lys Leu Arg Glu Leu Tyr Gly Pro
225                 230                 235                 240

Ala Ala Met Val Lys Val Gln Ala Ala Asp Lys Phe Gly Glu Trp
                245                 250                 255

Gly Lys Ala Gln Asp Val Leu Asp Gln Ser Arg Val Gln Glu Ile His
            260                 265                 270

Gln Val Leu Leu Lys Ser Ile Ala Glu Ser Thr Ser Leu Gly Gly Gly
        275                 280                 285

Ala Ala Val Phe Lys Asn Gln Ile Ala Gln Ile Asp Ser Val Phe Ser
    290                 295                 300

Ser Tyr Tyr Trp Met Trp Arg Ala Gly Ile Thr Pro Glu Ser Phe Pro
305                 310                 315                 320

Leu Leu Ser Asp Phe Leu Phe Glu Leu Gly Gln Asn Ala Arg Gly Ser
```

```
              325                 330                 335
Ala Lys Ile Ile Lys Thr Leu Asp Arg Ile Gly Leu Lys Trp Ser Lys
            340                 345                 350

Pro Leu Val Asn Leu Phe Ala Asp Ser Thr Phe Lys Met Gly Arg Ile
            355                 360                 365

His Met His Pro Ala Ile Leu Thr Thr Gly Arg Leu Asn Glu Met Gly
            370                 375                 380

Leu Cys Phe Gly Ile Ile Pro Ala Ser His Pro Glu Ser Ala Val Asn
385                 390                 395                 400

Gly Ser Gly Phe Ala Lys Asn Ile Leu Asn Val Arg Thr Asp Gly Met
                405                 410                 415

Asn Pro Ser Ala Gln Leu Ile Val Gln Leu Phe Asp Ile Gln Arg Gln
            420                 425                 430

Ser Arg Thr Leu Ser Asp Leu Asp Val Val Ser Glu His Leu Phe
            435                 440                 445

His Gln Ile Leu Val Gly Lys Arg Thr Ala Tyr Gln Asn Ala Phe Gln
            450                 455                 460

Val Lys Gly Asn Ala Thr Asp Thr Lys Ile Val Gly Phe Asp Pro Pro
465                 470                 475                 480

Lys Ile Asp Lys Asn Lys Ala Ile Arg Asp Ala Val Asp Gln His Leu
                485                 490                 495

Met Ala Ser Gly Tyr Ala Val Ala Pro Glu Arg Ser Val Met Asp Leu
            500                 505                 510

Arg Arg Glu Met Glu Glu Arg Glu His Lys Gln Arg Leu Glu Ala Leu
            515                 520                 525

Ala Ala Arg Ala Arg Glu Ala Glu Ala Trp Glu Ala Ser Arg Arg Ala
            530                 535                 540

Glu Met Ile Gln Lys Arg Ser Gly Val Arg Gly Pro Thr Val Gln
545                 550                 555                 560

Thr Gln Thr Leu Thr Val Gln Glu Gln Tyr Thr Ile Pro Lys Pro Met
                565                 570                 575

Gln Ser Pro Gln Val Gln Leu Met Gly Ala Gln Gly Ser Val Gln Tyr
            580                 585                 590

Leu Gly Ala Gly Ala Gln Gln Pro Ser Asp Pro Trp Phe Gln Ser Gln
            595                 600                 605

Ala Ser Ala Thr Ser Ile Pro Gln Gln Leu Pro Thr Glu Asp Tyr Thr
            610                 615                 620

Thr Ile Asn Leu Phe Lys
625                 630

<210> SEQ ID NO 7
<211> LENGTH: 7
<212> TYPE: PRT
<213> ORGANISM: Artificial sequence
<220> FEATURE:
<223> OTHER INFORMATION: Synthetic construct

<400> SEQUENCE: 7

Trp Thr Gln Val Ile Asp Gly
1               5

<210> SEQ ID NO 8
<211> LENGTH: 7
<212> TYPE: PRT
<213> ORGANISM: Artificial sequence
<220> FEATURE:
<223> OTHER INFORMATION: Synthetic construct
```

<400> SEQUENCE: 8

Glu Glu Pro Glu Ala Lys Leu
1               5

<210> SEQ ID NO 9
<211> LENGTH: 7
<212> TYPE: PRT
<213> ORGANISM: Artificial sequence
<220> FEATURE:
<223> OTHER INFORMATION: Synthetic construct

<400> SEQUENCE: 9

Trp Thr Gln Val Ile Asp Ser
1               5

<210> SEQ ID NO 10
<211> LENGTH: 7
<212> TYPE: PRT
<213> ORGANISM: Artificial sequence
<220> FEATURE:
<223> OTHER INFORMATION: Synthetic construct

<400> SEQUENCE: 10

Trp Thr Gln Val Ile Ala Gly
1               5

<210> SEQ ID NO 11
<211> LENGTH: 7
<212> TYPE: PRT
<213> ORGANISM: Artificial sequence
<220> FEATURE:
<223> OTHER INFORMATION: Synthetic construct

<400> SEQUENCE: 11

Trp Thr Gln Val Met Ala Gly
1               5

<210> SEQ ID NO 12
<211> LENGTH: 7
<212> TYPE: PRT
<213> ORGANISM: Artificial sequence
<220> FEATURE:
<223> OTHER INFORMATION: Synthetic construct

<400> SEQUENCE: 12

Trp Thr Gln Val Ile Ala Ser
1               5

<210> SEQ ID NO 13
<211> LENGTH: 7
<212> TYPE: PRT
<213> ORGANISM: Artificial sequence
<220> FEATURE:
<223> OTHER INFORMATION: Synthetic construct

<400> SEQUENCE: 13

Glu Glu Pro Glu Ala Arg Leu
1               5

<210> SEQ ID NO 14
<211> LENGTH: 7
<212> TYPE: PRT
<213> ORGANISM: Artificial sequence
<220> FEATURE:
<223> OTHER INFORMATION: Synthetic construct

```
<400> SEQUENCE: 14

Trp Thr Gln Val Leu Ala Gly
1               5

<210> SEQ ID NO 15
<211> LENGTH: 7
<212> TYPE: PRT
<213> ORGANISM: Artificial sequence
<220> FEATURE:
<223> OTHER INFORMATION: Synthetic construct

<400> SEQUENCE: 15

Asp Glu Pro Glu Ala Lys Leu
1               5

<210> SEQ ID NO 16
<211> LENGTH: 7
<212> TYPE: PRT
<213> ORGANISM: Artificial sequence
<220> FEATURE:
<223> OTHER INFORMATION: Synthetic construct

<400> SEQUENCE: 16

Trp Glu Arg Val Val Asp Glu
1               5

<210> SEQ ID NO 17
<211> LENGTH: 8
<212> TYPE: PRT
<213> ORGANISM: Artificial sequence
<220> FEATURE:
<223> OTHER INFORMATION: Synthetic construct

<400> SEQUENCE: 17

Thr Glu Pro Glu Ala Val Gly Thr
1               5

<210> SEQ ID NO 18
<211> LENGTH: 7
<212> TYPE: PRT
<213> ORGANISM: Artificial sequence
<220> FEATURE:
<223> OTHER INFORMATION: Synthetic construct

<400> SEQUENCE: 18

Trp Thr Gln Val Ile Ala Gly
1               5

<210> SEQ ID NO 19
<211> LENGTH: 8
<212> TYPE: PRT
<213> ORGANISM: Artificial sequence
<220> FEATURE:
<223> OTHER INFORMATION: Synthetic construct

<400> SEQUENCE: 19

Glu Glu Pro Glu Ala Arg Leu Val
1               5

<210> SEQ ID NO 20
<211> LENGTH: 7
<212> TYPE: PRT
<213> ORGANISM: Artificial sequence
<220> FEATURE:
<223> OTHER INFORMATION: Synthetic construct

<400> SEQUENCE: 20
```

Trp Glu Glu Val Val Pro Gly
1               5

<210> SEQ ID NO 21
<211> LENGTH: 8
<212> TYPE: PRT
<213> ORGANISM: Artificial sequence
<220> FEATURE:
<223> OTHER INFORMATION: Synthetic construct

<400> SEQUENCE: 21

Glu Glu Pro Glu Ala Lys Gly Leu
1               5

<210> SEQ ID NO 22
<211> LENGTH: 6
<212> TYPE: PRT
<213> ORGANISM: Artificial sequence
<220> FEATURE:
<223> OTHER INFORMATION: Synthetic construct

<400> SEQUENCE: 22

Trp Glu Asn Ile Glu Gly
1               5

<210> SEQ ID NO 23
<211> LENGTH: 8
<212> TYPE: PRT
<213> ORGANISM: Artificial sequence
<220> FEATURE:
<223> OTHER INFORMATION: Synthetic construct

<400> SEQUENCE: 23

Ile Glu Pro Glu Ala Ile Gly Leu
1               5

<210> SEQ ID NO 24
<211> LENGTH: 7
<212> TYPE: PRT
<213> ORGANISM: Artificial sequence
<220> FEATURE:
<223> OTHER INFORMATION: Synthetic construct

<400> SEQUENCE: 24

Trp Asp Ser Val Ser Asp Ile
1               5

<210> SEQ ID NO 25
<211> LENGTH: 8
<212> TYPE: PRT
<213> ORGANISM: Artificial sequence
<220> FEATURE:
<223> OTHER INFORMATION: Synthetic construct

<400> SEQUENCE: 25

Thr Glu Pro Glu Ala Ala Ala Thr
1               5

<210> SEQ ID NO 26
<211> LENGTH: 5
<212> TYPE: PRT
<213> ORGANISM: Artificial sequence
<220> FEATURE:
<223> OTHER INFORMATION: Synthetic construct
<220> FEATURE:
<221> NAME/KEY: MISC_FEATURE
<222> LOCATION: (1)..(1)

```
<223> OTHER INFORMATION: benzyloxycarbonyl

<400> SEQUENCE: 26

Arg Leu Arg Gly Gly
1               5
```